US012797514B2

United States Patent
(12) United States Patent
Taylor et al.

(10) Patent No.: US 12,797,514 B2
(45) Date of Patent: Nov. 17, 2026

(54) CELL-BASED BRAIN-MACHINE INTERFACE

(71) Applicant: Neuralink Corp., Fremont, CA (US)

(72) Inventors: Madison D. Taylor, Hillsborough, CA (US); Alan R. Mardinly, Oakland, CA (US); Alexandra Borog, Fremont, CA (US); Kevin S. Smith, Fremont, CA (US); Viktor Kharazia, Berkeley, CA (US); Thomas K. Roseberry, Palo Alto, CA (US); Jean-Charles Neel, San Francisco, CA (US); Emilienne M. Repak, Oakland, CA (US); Timothy J. Gardner, Eugene, OR (US); Max J. Hodak, San Francisco, CA (US); Sunny Y. Weber, San Luis Obispo, CA (US); Amir Mazaheripour, Oakland, CA (US)

(73) Assignee: Neuralink Corp., Fremont, CA (US)

( * ) Notice: Subject to any disclaimer, the term of this patent is extended or adjusted under 35 U.S.C. 154(b) by 1163 days.

(21) Appl. No.: 17/545,843

(22) Filed: Dec. 8, 2021

(65) Prior Publication Data

US 2023/0077899 A1 Mar. 16, 2023

Related U.S. Application Data

(60) Provisional application No. 63/242,281, filed on Sep. 9, 2021.

(51) Int. Cl.
*A61L 27/38* (2006.01)
*A61K 35/30* (2015.01)
(Continued)

(52) U.S. Cl.
CPC ............ *A61L 27/383* (2013.01); *A61K 35/30* (2013.01); *A61L 27/3834* (2013.01);
(Continued)

(58) Field of Classification Search
CPC ............... A61L 27/383; A61L 27/3834; A61L 27/3878; A61L 27/3895; A61K 35/30; A61N 1/0531; A61N 1/0551; A61P 25/28
See application file for complete search history.

(56) References Cited

U.S. PATENT DOCUMENTS 9,829,492 B2 11/2017 Deisseroth et al.
2013/0171116 A1 7/2013 Shoham et al.
(Continued)

FOREIGN PATENT DOCUMENTS

WO 2017181068 A1 10/2017
WO 2023038829 A1 3/2023

OTHER PUBLICATIONS

M. Zeitelhofer et al., "High-efficiency transfection of mammalian neurons via nucleofection," Nat. Protoc, vol. 2, No. 7, pp. 1692-1704, 2007. (Year: 2007).*
(Continued)

*Primary Examiner* — Joanne M Rodden
*Assistant Examiner* — Dana Stumpfoll
(74) *Attorney, Agent, or Firm* — Oblon, McClelland, Maier & Neustadt, L.L.P.

(57) ABSTRACT

The disclosure provides a biological brain-computer interface comprising genetically modified cells engrafted onto an adult mammal (e.g., mouse) above cortical layer 1, forming an artificial cortical layer termed layer zero (L0). Following engraftment, L0 goes through a developmental process characterized by synchronous waves of activity that gradually recede to resemble spontaneous cortical activity. Axons and dendrites from L0 nondestructively infiltrated the host cortex and formed synaptic connections necessary for bidirectional communication with the brain.

18 Claims, 25 Drawing Sheets
(17 of 25 Drawing Sheet(s) Filed in Color)

Implant 'tethered' cells: 100% juxtra recording yield

(51) Int. Cl.
*A61N 1/05* (2006.01)
*A61P 25/28* (2006.01)

(52) U.S. Cl.
CPC ....... *A61L 27/3878* (2013.01); *A61L 27/3895* (2013.01); *A61N 1/0531* (2013.01); *A61P 25/28* (2018.01)

(56) References Cited

U.S. PATENT DOCUMENTS

| | | | |
|---|---|---|---|
| 2014/0101785 A1 | 4/2014 | Looger et al. | |
| 2014/0228857 A1 | 8/2014 | Kodandaramaiah et al. | |
| 2015/0369771 A1 | 12/2015 | Richardson-Burns et al. | |
| 2017/0080256 A1 | 3/2017 | Kim et al. | |
| 2017/0276668 A1 | 9/2017 | Curley et al. | |
| 2019/0126043 A1* | 5/2019 | Cullen | A61N 1/05 |
| 2020/0386742 A1 | 12/2020 | Moore et al. | |
| 2020/0393902 A1 | 12/2020 | Mann et al. | |
| 2020/0407577 A1 | 12/2020 | Gatenholm et al. | |
| 2021/0004084 A1 | 1/2021 | Milstein | |
| 2021/0007602 A1 | 1/2021 | Seo et al. | |

OTHER PUBLICATIONS

Q. Chen et al., "Imaging neural activity using Thy1-GCaMP transgenic mice," Neuron, vol. 76, No. 2, pp. 297-308, 2012. (Year: 2012).*

Rochford et al., When Bio Meets Technology: Biohybrid Neural Interfaces, Adv. Mater. 2020, pp. 1-17, vol. 32, 1903182, Wiley-VCH Verlag GmbH & Co. KgaA, Weinheim.

Adewole et al., "Development of Optically Controlled Living Electrodes/ with Long-projecting Axon Tracts for a Synaptic Brain-machine Interface," ScienceAdvances, vol. 7, No. 4, Jan. 22, 2021, 15 pages.

Broussard et al., "In Vivo Measurement of Afferent Activity With Axon-Specific Calcium Imaging," Nature Neuroscience, vol. 21, No. 9, Aug. 20, 2018, pp. 1272-1280.

Liberti et al., "Local Network Coordination Supports Neuroprosthetic Control," IEEE Xplore, Mar. 20-23, 2019, pp. 558-561.

Michelson et al., "Multi-scale, Multi-modal Analysis Uncovers Complex Relationship at the Brain Tissue-implant Neural Interface: New Emphasis on the Biological Interface," Journal of Neural Engineering, vol. 15, No. 3, Apr. 6, 2018, 24 pages.

Application No. PCT/US2022/041997, International Search Report and Written Opinion, mailed on Jan. 10, 2023, 12 pages.

Serruya et al., "Engineered Axonal Tracts as "living Electrodes" for Synaptic-Based Modulation of Neural Circuitry," Available Online at https://onlinelibrary.wiley.com/doi/epdf/10.1002/adfm.201701183, vol. 28, No. 12, Sep. 4, 2017, 18 pages.

Zhang et al., "The Combination of Brain-Computer Interfaces and Artificial Intelligence: Applications and Challenges," Annals of Translational Medicine, vol. 8, No. 11, Jun. 15, 2020, 9 pages.

Aberra et al., Biophysically Realistic Neuron Models for Simulation of Cortical Stimulation, Journal of Neural Engineering, vol. 15, No. 6, Dec. 2018, 28 pages.

Adewole et al., Development of Optically-Controlled Living Electrodes with Long-Projecting Axon Tracts for a Synaptic Brain-Machine Interface, Science Advances, vol. 7, No. 4, Available Online at: https://doi.org/10.1101/333526, Oct. 4, 2020, 29 pages.

Aharoni et al., Circuit Investigations with Open-Source Miniaturized Microscopes: Past, Present and Future, Frontiers in Cellular Neuroscience, vol. 13, Article 141, Apr. 5, 2019, 12 pages.

Anderson et al., The Connection from Cortical Area V1 to V5: A Light and Electron Microscopic Study, The Journal of Neuroscience, vol. 18, No. 24, Dec. 15, 1998, pp. 10525-10540.

Anumanchipalli et al., Speech Synthesis from Neural Decoding of Spoken Sentences, Nature, vol. 568, Apr. 25, 2019, 20 pages.

Azemi et al., Seeding Neural Progenitor Cells on Silicon-Based Neural Probes, Journal of Neurosurgery, vol. 113, Sep. 2010, pp. 673-681.

Azemi et al., The Surface Immobilization of the Neural Adhesion Molecule L1 on Neural Probes and its Effect on Neuronal Density and Gliosis at the Probe/Tissue Interface, Biomaterials, vol. 32, Jan. 2011, pp. 681-692.

Baraban et al., Reduction of Seizures by Transplantation of Cortical GABAergic Interneuron Precursors into Kv1.1 Mutant Mice, Proceedings of the National Academy of Sciences of the United States of America (PNAS), vol. 106, No. 36, Sep. 8, 2009, pp. 15472-15477.

Barrese et al., Failure Mode Analysis of Silicon-Based Intracortical Microelectrode Arrays in Non-Human Primates, Journal of Neural Engineering, vol. 10, No. 6, Nov. 12, 2013, 23 pages.

Bartels et al., Neurotrophic Electrode: Method of Assembly and Implantation into Human Motor Speech Cortex, Journal of Neuroscience Methods, vol. 174, No. 2, Sep. 30, 2008, pp. 168-176.

Bollimunta et al., Head-Mounted Microendoscopic Calcium Imaging in Dorsal Premotor Cortex of Behaving Rhesus Macaque, Cell Reports, vol. 35, Jun. 15, 2021, 21 pages.

Buzsaki et al., The Origin of Extracellular Fields and Currents—EEG, ECOG, LFP and Spikes, Nature Reviews | Neuroscience, vol. 13, Jun. 2012, pp. 407-420.

Byers et al., Direct in Vivo Assessment of Human Stem Cell Graft—Host Neural Circuits, NeuroImage, vol. 114, Jul. 1, 2015, 10 pages.

Chen et al., A Synaptic Ras-GTPase Activating Protein (p135 SynGAP) Inhibited by CaM Kinase II, Neuron, vol. 20, May 1998, pp. 895-904.

Chung et al., High-Density, Long-Lasting, and Multi-Region Electrophysiological Recordings Using Polymer Electrode Arrays, Neuron, vol. 101, Jan. 2, 2019, pp. 1-11.

Clancy et al., Volitional Modulation of Optically Recorded Calcium Signals During Neuroprosthetic Learning, Nature Neuroscience, vol. 17, No. 6, Jun. 2014, 4 pages.

Dana et al., High-Performance Calcium Sensors for Imaging Activity in Neuronal Populations and Microcompartments, Nature Methods, vol. 16, Jul. 2019, pp. 649-657.

Daviaud et al., Vascularization and Engraftment of Transplanted Human Cerebral Organoids in Mouse Cortex, Disorders of the Nervous System, vol. 5, No. 6, Nov.-Dec. 2018, pp. 1-18.

Davis et al., Inhibitory Neuron Transplantation into Adult Visual Cortex Creates a New Critical Period that Rescues Impaired Vision, Neuron, vol. 86, May 20, 2015, pp. 1-12.

Eles et al., Neuroadhesive L1 Coating Attenuates Acute Microglial Attachment to Neural Electrodes as Revealed by Live Two-Photon Microscopy, Biomaterials, vol. 113, Jan. 2017, pp. 279-292.

Esclapez et al., Comparative Localization of Two Forms of Glutamic Acid Decarboxylase and Their mRNAs in Rat Brain Supports the Concept of Functional Differences between the Forms, The Journal of Neuroscience, vol. 14, No. 3, Mar. 1994, pp. 1834-1855.

Falkner et al., Transplanted Embryonic Neurons Integrate into Adult Neocortical Circuits, Nature, vol. 539, Nov. 10, 2016, pp. 248-271.

Fandel et al., Transplanted Human Stem Cell-Derived Interneuron Precursors Mitigate Mouse Bladder Dysfunction and Central Neuropathic Pain after Spinal Cord Injury, Cell Stem Cell, vol. 19, Oct. 6, 2016, pp. 1-14.

Ferreira et al., Neuronal Morphometry Directly from Bitmap Images, Nature Methods, vol. 11, No. 10, Oct. 2014, pp. 982-984.

Gheusi et al., Adult-Born Neurons in the Olfactory Bulb: Integration and Functional Consequences, Current Topics in Behavioral Neurosciences, vol. 15, Jan. 1, 2013, pp. 49-72.

Gomez-Nicola et al., Microglial Dynamics and Role in the Healthy and Diseased Brain: A Paradigm of Functional Plasticity, The Neuroscientist, Apr. 24, 2014, 17 pages.

Goncalves et al., Adult Neurogenesis in the Hippocampus: From Stem Cells to Behavior, Cell, vol. 167, Nov. 3, 2016, pp. 897-914.

Harris et al., Hierarchical Organization of Cortical and Thalamic Connectivity, Nature, vol. 575, No. 7781, Oct. 30, 2019, 30 pages.

Hellwig et al., Synapses on Axon Collaterals of Pyramidal Cells are Spaced at Random Intervals: A Golgi Study in the Mouse Cerebral Cortex, Biological Cybernetics, vol. 71, No. 1, May 1994, pp. 1-12.

Hochberg et al., Reach and Grasp by People with Tetraplegia Using a Neurally Controlled Robotic Arm, Nature, vol. 485, May 17, 2012, pp. 372-375.

(56) References Cited

OTHER PUBLICATIONS

Liddelow et al., Reactive Astrocytes: Production, Function, and Therapeutic Potential, Immunity, vol. 46, Jun. 20, 2017, pp. 957-967.
Longair et al., Simple Neurite Tracer: Open Source Software for Reconstruction, Visualization and Analysis of Neuronal Processes, Bioinformatics, vol. 27, No. 17, Sep. 1, 2011, pp. 2453-2454.
Mansour et al., An In Vivo Model of Functional and Vascularized Human Brain Organoids, Nature Biotechnology, vol. 36, Apr. 16, 2018, 16 pages.
Marblestone et al., Physical Principles for Scalable Neural Recording, Frontiers in Computational Neuroscience, vol. 7, Article 137, Oct. 2013, 34 pages.
Mcalinden et al., Multisite MicroLED Optrode Array for Neural Interfacing, Neurophotonics, vol. 6, No. 3, Jul.-Sep. 2019, pp. 035010-1-035010-9.
Miccoli et al., High-Density Electrical Recording and Impedance Imaging with a Multi-Modal CMOS Multi-Electrode Array Chip, Frontiers in Neuroscience, vol. 13, Article 641, Jun. 2019, 14 pages.
Michelson et al., Calcium Activation of Cortical Neurons by Continuous Electrical Stimulation: Frequency Dependence, Temporal Fidelity, and Activation Density, Journal of Neuroscience Research, vol. 97, Issue 5, Nov. 28, 2018, pp. 1-19.
Mitani et al., Brain-Computer Interface with Inhibitory Neurons Reveals Subtype-Specific Strategies, Current Biology, vol. 28, Jan. 8, 2018, pp. 1-7.
Nolta et al., BBB Leakage, Astrogliosis, and Tissue Loss Correlate with Silicon Microelectrode Array Recording Performance, Biomaterials, vol. 53, Jan. 2015, pp. 753-762.
Pachitariu et al., Suite2p: Beyond 10,000 Neurons with Standard Two-Photon Microscopy, Available Online at: https://doi.org/10.1101/061507, Jul. 20, 2017, 30 pages.
Palma-Tortosa et al., Activity in Grafted Human iPS Cell-Derived Cortical Neurons Integrated in Stroke-Injured Rat Brain Regulates Motor Behavior, Proceedings of the National Academy of Sciences of the United States of America (PNAS), vol. 117, No. 16, Apr. 21, 2020, pp. 1-7.
Pandarinath et al., High Performance Communication by People with Paralysis Using an Intracortical Brain-Computer Interface, Human Biology and Medicine, vol. 6, Feb. 21, 2017, 27 pages.
Polikov et al., Response of Brain Tissue to Chronically Implanted Neural Electrodes, Journal of Neuroscience Methods, vol. 148, Oct. 15, 2005, pp. 1-18.
Prsa et al., Rapid Integration of Artificial Sensory Feedback during Operant Conditioning of Motor Cortex Neurons, Neuron, vol. 93, Feb. 22, 2017, pp. 929-939.
Purcell et al., In Vivo Evaluation of a Neural Stem Cell-Seeded Prosthesis, Journal of Neural Engineering, vol. 6, No. 2, Apr. 2009, 10 pages.
Righi et al., Peptide-Based Coatings for Flexible Implantable Neural Interfaces, Scientific Reports, vol. 8, Article No. 502, Jan. 11, 2018, 14 pages.
Rochefort et al., Sparsification of Neuronal Activity in the Visual Cortex at Eye-Opening, Proceedings of the National Academy of Sciences of the United States of America (PNAS), vol. 106, No. 35, Sep. 1, 2009, pp. 15049-15054.
Saxena et al., The Impact of Chronic Blood-Brain Barrier Breach on Intracortical Electrode Function, Biomaterials, vol. 34, No. 20, Jul. 2013, pp. 4703-4713.
Simon et al., Progenitors in the Adult Cerebral Cortex: Cell Cycle Properties and Regulation by Physiological Stimuli and Injury, GLIA, vol. 59, No. 6, Jun. 2011, pp. 869-881.
Stringer et al., Cellpose: A Generalist Algorithm for Cellular Segmentation, Nature Methods, vol. 18, No. 1, Jan. 2021, 21 pages.
Trautmann et al., Dendritic Calcium Signals in Rhesus Macaque Motor Cortex Drive an Optical Brain-Computer Interface, Nature Communications, vol. 12, No. 1, Article 3689, Jun. 17, 2021, 20 pages.
Viswam et al., Optimal Electrode Size for Multi-Scale Extracellular—Potential Recording from Neuronal Assemblies, Frontiers Neuroscience, Available Online at: https://doi.org/10.3389/fnins.2019.00385, Apr. 26, 2019, 45 pages.
Wang et al., An Electrocorticographic Brain Interface in an Individual with Tetraplegia, PLoS One, vol. 8, Issue 2, Feb. 2013, 8 pages.
Wiedenmann et al., Identification and Localization of Synaptophysin, an Integral Membrane Glycoprote, n of Mr 38,000 Characteristic of Presynaptic Vesicles, Cell, vol. 41, Jul. 1985, pp. 1017-1028.
Willett et al., High-Performance Brain-To-Text Communication via Handwriting, Nature, vol. 593, May 12, 2021, pp. 249-254.
Wolf, Thermal Considerations for the Design of an Implanted Cortical Brain-Machine Interface (BMI), Frontiers in NeuroEngineering, Jan. 2008, 20 pages.
Yang et al., Bioinspired Neuron-Like Electronics, Nature Materials, vol. 18, Feb. 25, 2019, 13 pages.
"International Search Report and Written Opinion," mailed Jan. 10, 2023 in International Application No. PCT/US2022/041997. 12 pages.

* cited by examiner

FIG. 9A
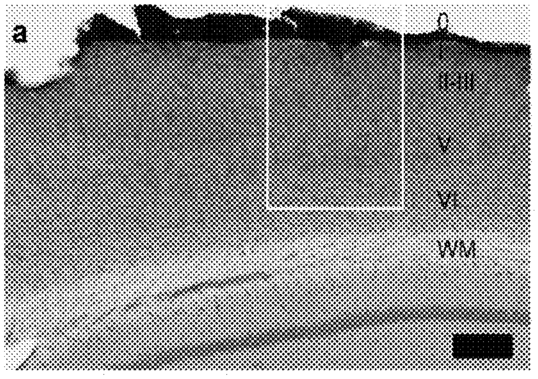
FIG. 9C
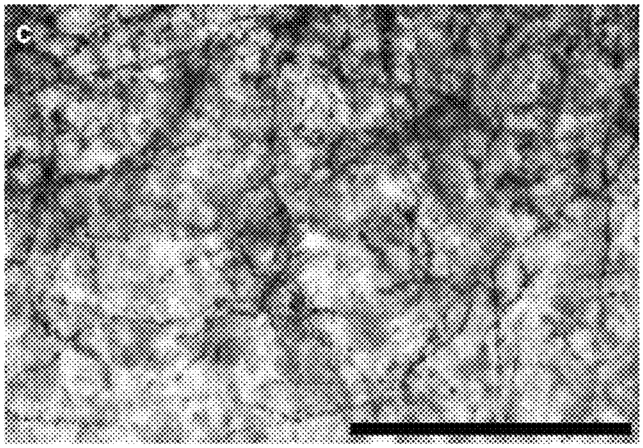
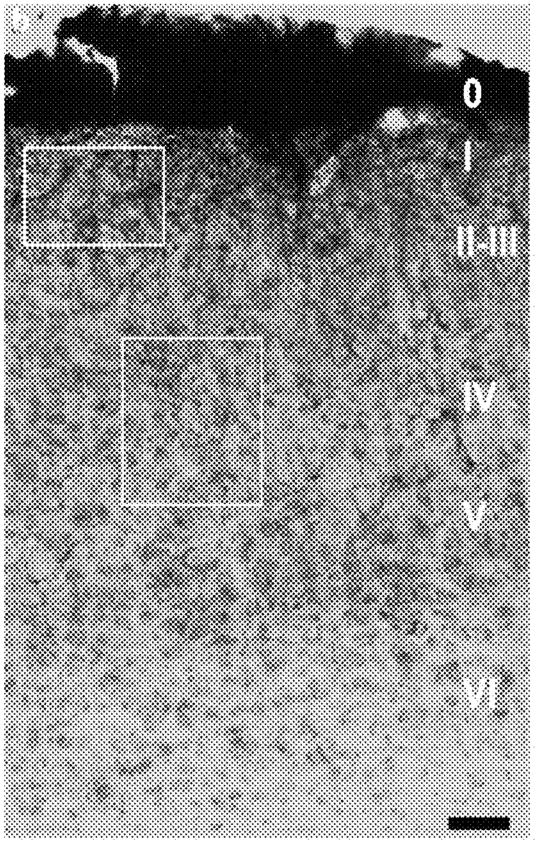
FIG. 9B
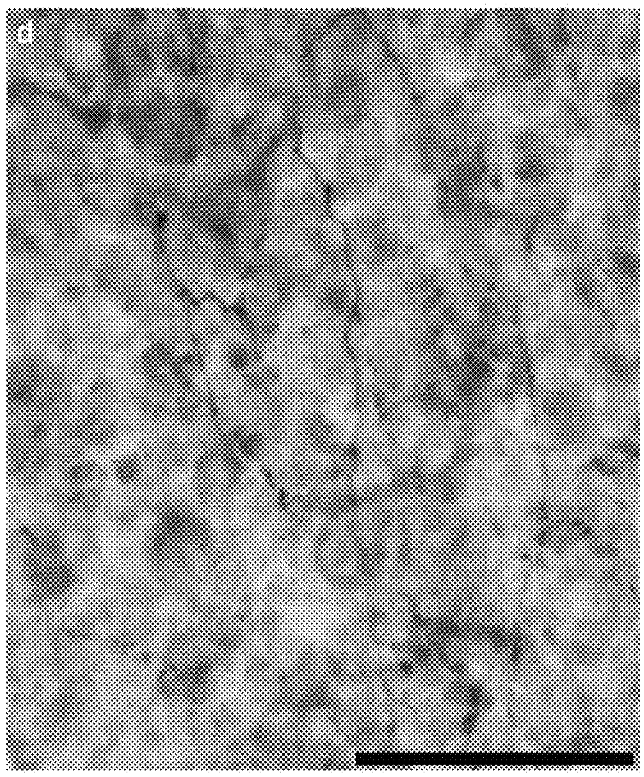
FIG. 9D

CELL-BASED BRAIN-MACHINE INTERFACE

CROSS-REFERENCE TO RELATED APPLICATIONS

The present application claims priority to U.S. Provisional Application No. 63/242,281, filed Sep. 9, 2021, the disclosure of which is hereby incorporated by reference in its entirety for all purposes.

BACKGROUND

There are numerous challenges to scaling brain-machine interfaces (BMIs) to achieve bidirectional communication with the millions of neurons likely needed to seamlessly interface humans with technology. A stable, very high-bandwidth interface between human brains and computers would enable therapies for neurological disorders and reduce the bottleneck of information transfer between the biological and digital domains.

Non-invasive BMIs can extract useful information from bulk optical or electrical signals spatially distributed across the cranium, but these signals represent the summed and convolved activity of millions of neurons, making non-invasive devices poor candidates for high-bandwidth communication. Recording from the brain surface, as in electrocorticography (ECoG) recordings, improves signal quality and allows more impressive demonstrations of neural decoding. However, these recordings still mix signals from thousands of neurons and only rarely record action potentials due to the paucity of neurons in cortical layer 1 (L1). In contrast, penetrating intracortical BMIs communicate with the brain at the level with which it functions i.e., specific action potentials from specific neurons. This enables penetrating BMIs to achieve bit rates that enable useful neurally-controlled typing.

However, stably recording from a large number of channels via penetrating implants is challenging as each penetration of the brain displaces tissue, limiting the scale at which intracortical arrays can be deployed. For traditional stiff arrays, damage from probe penetrations disrupts microvasculature and activates neuroimmune cells, leading to biofouling, formation of a glial scar, and fibrotic encapsulation. Recently, a new generation of fine and flexible electrode arrays have been developed to mitigate the biological response to implantation. Decoupling the stiffness required for insertion from the array allows use of materials better matched to the physical properties of brain tissue. These implants have improved damage profiles that allow for stable recordings with increased channel count relative to previous chronically implanted electrode arrays. While flexible probes cause less cortical damage and disruption of the blood-brain barrier than stiff penetrating electrodes, tissue displacement is likely to become a prohibitive obstacle to scaling them to record from millions of neurons. Additionally, since electrical stimulation of the brain through implanted electrode arrays excites both axons and cell bodies, the activated neurons are spatially distributed and extremely sensitive to small changes in stimulation parameters. Together, these obstacles represent significant challenges to developing stable ultra-high-bandwidth bidirectional BMIs.

Biological approaches have been deployed in conjunction with conventional recording techniques in an attempt to ameliorate these challenges. For instance, electrodes that coax neurons to grow into a glass pipette using neurotrophins showed promise for improving recording longevity. Coating neural probes with cell-surface proteins has reduced the foreign body response and shown promise for improving recording quality. Extending this line of investigation, neural probes seeded with neural progenitor cells were implanted in the hopes of providing trophic support to damaged cells and providing a biocompatible surface to reduce the glial foreign body response. Alternatively, using calcium imaging, BMIs can record from large numbers of neurons without invasive electrodes, an approach that has recently gained traction in large animal models. However, this carries the very significant drawback of requiring viral infection of a large neural population.

There is a need in the art for new brain-machine interfaces (BMI) that use living neuronal cells optionally coupled to electrodes that communicate to an external device. The current disclosure satisfies this need and offers other advantages as well.

BRIEF SUMMARY

In one embodiment, the present disclosure provides a brain-computer interface (BCI) engrafted on a brain of a mammal, the BCI comprising:

- a cortical graft layer comprising a plurality of neuronal cells transplanted on a brain's cerebral cortex, wherein the plurality of cells engraft on the brain and respond to an external stimulus with a detectable signal.

In another embodiment, the present disclosure provides a method for bi-directional communication between a brain-computer interface (BCI) engrafted on a brain of a mammal and a computer, the method comprising:

- providing a cortical graft layer comprising a plurality of neuronal cells transplanted on a brain's cerebral cortex of the mammal; and
- providing an external stimulus to the mammal wherein the plurality of cells engrafted on the brain respond to an external stimulus with a detectable neural signal.

In still another embodiment, the present disclosure provides a method of connecting a biological brain-machine interface with a subject, the method comprising:

- depositing neuronal cells onto a cortical surface of a brain of a subject, the cells being selected to emit light or an electrical signal in response to a neural signal;
- allowing the cells to form an additional cortical layer that grows and integrates into the brain; and
- recording light or an electrical signal emitted from the cells in response to a neural signal in the brain.

In still yet another embodiment, the present disclosure provides a method of stimulating a brain with a biological brain-machine interface, the method comprising:

- depositing neuronal cells onto a cortical surface of a brain of a subject, the cells being selected to convert light or an electrical signal to an electrical signal compatible with neurons in the brain;
- allowing the cells to form an additional cortical layer that grows and integrates into the brain;
- directing light at or an electrical signal to the cells in the additional cortical layer such that the cells convert the light or the electrical signal to a neural signal; and
- measuring a response or a behavior of the subject correlated with the directed light or electrical signal.

These and other objects, aspects and embodiments will become more apparent when read with the detailed description and figures which follow.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9A shows a layer Zero brain section stained with DAB-enhanced anti-GFP against GCaMP-expressing engrafted neurons (black), cresyl violet (blue). Scale bar is 200 μm FIG. 9B shows an inset showing penetration of superficial cortical layers by L0 dendrites. Scale bar is 200 μm.

FIG. 9C shows an inset showing higher magnification image of L0 dendrites in L2. Scale bar is 50 μm FIG. 9D shows an inset showing L0 axons in L4. Scale bar is 50 μm.

DETAILED DESCRIPTION

Figure 1A:
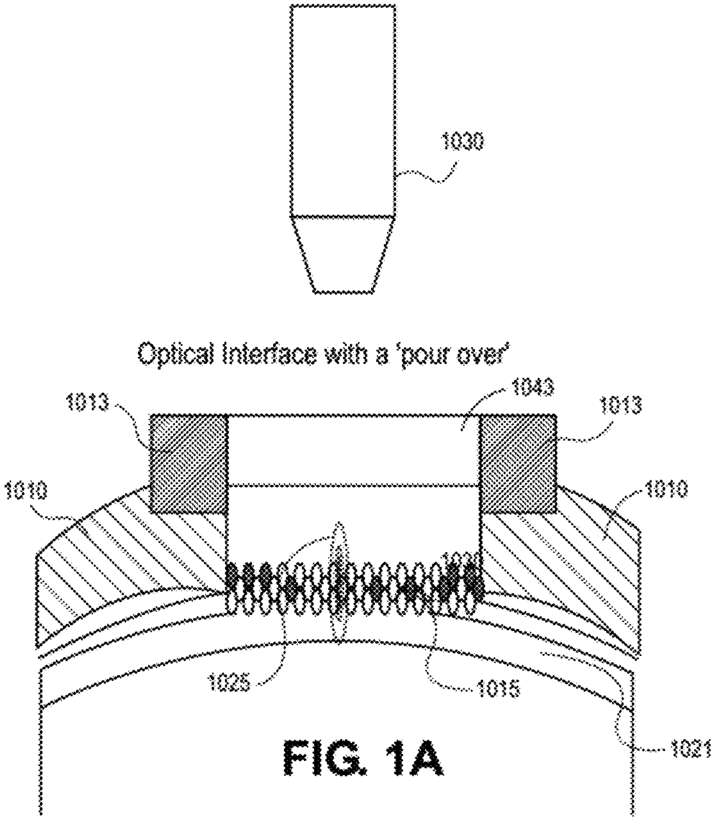
FIG. 1A-FIG. 1D show various embodiments of a Brain Machine Interface (BMI) using an optical approach (FIG. 1A); an approach using a ECoG and pour-over cells (FIG. 1B); an approach using tethered cells (FIG. 1C); and an approach using embedded cells in a polymer (FIG. 1D).

In the present disclosure, an artificial cortical layer or graft (layer zero or "L0") has been generated by depositing GCaMP-expressing neurons onto the cortical surface where they are easily accessed by optical or electronic recording. GCaMP is a genetically encoded calcium indicator (GECI), which in certain instances, is a synthetic fusion of green fluorescent protein, calmodulin, and M13 (a peptide sequence from myosin light-chain kinase). The graft integrates with the brain to form an interface layer capable of transforming information from the brain to its surface, where it can then be read. Thereafter, L0 undergoes a developmental process over several weeks characterized by strong waves of activity that gradually decorrelate to resemble spontaneous cortical activity. After this developmental process, mammals (e.g., mice) were trained to use L0 to perform an optical brain machine interface task. The results indicate that the mammal (e.g. mice) can perform at levels similar to mice expressing viral GCaMP in layer 2 (L2). Histological analysis shows that L0 neurons extend dendrites into the superficial cortical layers and axons that extend throughout the cortical volume. Advantageously, this data provides a demonstration of a biological brain-computer interface capable of bidirectional communication in a mammal.

Definitions

As used herein, the term "brain-machine interface" or "BMI" refers to a layer of neuronal cells engrafted onto and that integrates into a surface or layer of a mammalian brain. A BMI is capable of communicating a neural activation into a response recordable in an external device. Bidirectional brain-machine interfaces (BMIs) establish a two-way direct communication link between the mammalian brain and the external device. The term "brain-computer-interface (BCI) is used interchangeably with BMI herein.

As used herein, the term "cerebral cortex" is the outer most layer of neural tissue of the cerebrum of a brain in a mammal, such as a human.

As used herein, the term "tethered" refers to a cell, such as a neuronal cell that is attached or joined (e.g., chemically) to an electrode or pad.

As used herein, the term "cortical graft layer" refers to a layer of cells that is deposited or poured over a cerebral cortex of a mammal.

As used herein, the term "electrocorticography" refers to the process of recording electrical activity in a brain by placing electrodes in direct contact with the cerebral cortex or surface of the brain. An electrocorticogram (ECOG) is the tracing of a brain wave made by an electrocorticographic apparatus (an ECoG) used for detecting and recording brain waves made with the electrodes in direct contact with the brain.

As used herein, the term "external stimulus" refers to an outside change to the external environment that is detected by a mammalian subject. Changes to light, an electrical impulse, sound and temperature are examples of external stimuli. The external environment can be external to a neuron or external to the mammalian subject.

As used herein, the term "hydrogel" refers to a water-insoluble, optionally cross-linked, three-dimensional network of polymer chains with voids between polymer chains filled with or capable of being filled with water. A hydrogel package is a construct or structure made of one or more hydrogel polymer(s).

As used herein, the term "L1" or "layer 1" refers to the first layer of the cerebral cortex or the sheet of neural tissue that is outermost to the cerebrum.

As used herein, the term "L0" or "layer 0" refers to a layer of exogenous cells placed or poured over the cerebral cortex. The poured over cells can be a transfected cell with exogenous functionalities.

As used herein, the term "transfection" refers to the taking up of exogenous nucleic acid, e.g., an expression vector, by a host cell whether or not any coding sequences are, in fact, expressed. Numerous methods of transfection are known to an ordinarily skilled artisan, for example, by *Agrobacterium*-mediated transformation, protoplast transformation, lipid-mediated delivery, liposomes, electroporation, sonoporation, microinjection, particle bombardment and silicon carbide whisker-mediated transformation and combinations thereof.

As used herein, the term "neural network" refers to a plurality of interconnected neurons (i.e., at least two neurons) whose activation defines a recognizable linear pathway. The interface through which neurons interact with their neighbors usually consists of several axon terminals connected via synapses to dendrites on other neurons. If the sum of the input signals into one neuron surpasses a certain threshold, the neuron sends an action potential (AP) at the axon hillock and transmits this electrical signal along the axon.

As used herein, the term "nervous system" refers to a complex network of nerve cells, or neurons, found centrally in the brain and spinal cord and peripherally in the various nerves of the body. Neurons have a cell body, dendrites and an axon.

As used herein, the term "nerve" refers to a group of neurons that serves a particular part of the body. Nerves can contain several hundred neurons to several hundred thousand neurons. Nerves often contain both afferent neurons (which carry signals back to the central nervous system) and the efferent neurons (which carry signals to the periphery). Electrical signals are conducted via neurons and nerves. Neurons release neurotransmitters at synapses with other nerves to allow continuation and modulation of the electrical signal. A "ganglion" refers to a group of neuronal cell bodies in one location As used herein "subject" or "patient" or "individual" refers to any subject, patient, or individual, and the terms are used interchangeably herein. In this regard, the terms "subject," "patient," and "individual" includes mammals, and, in particular humans.

Embodiments

The present disclosure provides a brain-machine interface (BMI) in the form of a layer of neuronal cells that can be grafted onto the outer layer of the cerebral cortex to provide bidirectional communication between the brain and an external device. An artificial cortical L0 formed from transplanted neurons functions as a BMI or an interface between external recording devices and the brain. This L0 layer survives, develops, and integrates with the brain.

In certain aspects, L0 is utilized as an a BCI by requiring a mammal (e.g., a mouse) to volitionally modulate L0 activity to obtain rewards. These results indicate that L0 is integrated with the brain to a degree sufficient for the animal to control, or modulate, it's activity patterns. Histology supports these results by revealing that L0 extends spiny dendrites that possess synaptic markers into the superficial layers of the cortex.

By grafting neurons to form L0, recordings from the brain at single neuron resolution are obtained without genetic modification of the host organism and with no traumatic penetration of the brain's parenchyma. Instead, the brain is penetrated by naturally in-growing neurites, and bidirectional communication is achieved via chemical synapses, blurring the boundary between implant and host.

In certain aspects, an optical approach is used to complete a BMI task in a mammal. In some instances, neuronal activity is measured using genetically encoded calcium indicators and microscopy. Various fluorescent proteins enhance the detection of neural activity.

The present disclosure provides a brain-computer interface (BCI) engrafted on a brain of a mammal, the BCI comprising:

a cortical graft layer comprising a plurality of neuronal cells transplanted on a brain's cerebral cortex, wherein the plurality of cells engraft on the brain and respond to an external stimulus with a detectable signal.

In certain instances, fluorescently labeled cells derived from established lines such as neural cells or autologous stem cells, are deposited on top of a mammalian cortex, spinal cord, cranial nerve or a combination thereof and a clear window is fixed over the transplantation site. In one instance, the cells are deposited on top of a mammalian cortex.

In certain aspects, the plurality of neuronal cells are transfected, wherein the transfection can be ex vivo with a plasmid such as by electroporation. Alternatively, in certain aspects, transfection is via virus-mediated transfection.

In certain aspects, the plurality of neuronal cells are tissue cultured mammalian stem cells. Other suitable cells include, but are not limited to, a glial cell, an embryonic cell, a mesenchymal stem cell, a cell derived from an induced pluripotent stem cell, a sympathetic neuron, a parasympathetic neuron, a spinal motor neurons, a central nervous system neuron, a peripheral nervous system neuron, an enteric nervous system neurons, a motor neuron, a sensory neuron, a cholinergic neuron, a GABAergic neuron, a glutamatergic neuron, a dopaminergic neuron, a serotonergic neuron, an interneuron, an adrenergic neuron, a trigeminal ganglion, an astrocyte, an oligodendrocyte, a Schwann cell, a microglial cell, an ependymal cell, a radial glial cell, a satellite cell, an enteric glial cell, a pituicyte, an embryonic stem cell, an induced pluripotent stem cell, and combinations thereof. The cells can be autologous cells or allogenic cells.

The cells (e.g., neuronal cells) in the disclosure can be derived from one site and transplanted to another site within the same subject as an autograft. Furthermore, the cells (e.g., neuronal cells) in the disclosure can be derived from a genetically identical donor and transplanted as an isograft. Still further, the cells (e.g., neuronal cells) in the disclosure can be derived from a genetically non-identical member of the same species and transplanted as an allograft. Alternatively, cells (e.g., neuronal cells) can be derived from non-human origin and transplanted as a xenograft. With the development of powerful immunosuppressants, allografts and xenografts of non-human neural precursors, such as neural precursors of porcine origin or other mammals, can be grafted into human subjects. Cell engraftment typically involves the administration or injection of either whole cells or cell extracts that are xenogenic, allogenic (from another human donor), or autologous (wherein the cells are extracted from and transplanted back into the same patient or subject).

In certain aspects, the plurality of neuronal cells are tethered (e.g., chemically such as covalently) to an electrode. For example, in one approach, a ligand on the surface of an electrode is bound through a protein-protein interaction to specific areas of neuronal cells. The functionalize electrode surface is genetically engineered to express a neuroligin-1 protein that forms a nascent presynaptic bouton upon binding to neurexin-1β on the presynaptic membrane of neurons. (See, Jeon J, Yoon et al., S H, "Neuroligin-1-Modified Electrodes for Specific Coupling with a Presynaptic Neuronal Membrane" *ACS Appl Mater Interfaces. May* 2021, 13(18):21944-21953). Other polymers used for tethering are known to those skilled in the art.

In certain aspects, the neuronal response is detected optically. For example, the response can be detected using microscopy, such as by using calcium imaging microscopy. Calcium imaging takes advantage of calcium indicators, fluorescent molecules that respond to the binding of $Ca^{2+}$ ions by fluorescent properties. Two main classes of calcium indicators exist i.e., chemical indicators and genetically encoded calcium indicators (GECI). This technique allows calcium signaling in a wide variety of cell types. In neurons, electrical activity is typically accompanied by an influx of $Ca^{2+}$ ions. When bound to $Ca^{2+}$, GCaMP fluoresces green with a peak excitation wavelength of 480 nm and a peak emission wavelength of 510 nm. In this manner, intracellular $Ca^{2+}$ levels are measured using transfected or transgenic cells.

GCaMP is commonly used to measure increases in intracellular $Ca^{2+}$ in neurons as a proxy for neuronal activity in animal models. Action potentials induce neurotransmitter release at axon terminals by opening voltage-gated $Ca^{2+}$ channels, allowing for $Ca^{2+}$ influx. GCaMP can be used to identify and measure activity patterns in specific regions of a mammalian brain.

In certain aspects, the plasmid contains an exogenous nucleic acid sequence selected from the group consisting of pCAG-H2B-mRuby3-P2A-GCaMP7s, pCAG-ChRimson-tdTomato (SEQ ID NO: 3), pCAG-ChR2-tdTomato, and pCAG-mRuby3 (SEQ ID NO: 4) to facilitate imaging. In certain instances, the exogenous nucleic acid is a calcium indicator such as pCAG-H2B-mRuby3-P2A-GCaMP7s.

As shown in FIG. 1A, an imaging device 1030, for example, a multi-photon microscope or Miniscope is utilized to observe and image in vivo neural activity and complete a BMI task. A clear cranial window 1043 is fixed 1013 on the cranium 1010 over a transplantation site. The device 1030 is configured to excite 1025 and detect fluorescent changes and responses in the genetically modified cells 1015. The genetically modified cells 1015 are deposited on top of the cortex 1021 of a mammal. The combination of genetically encoded calcium ($Ca^{2+}$) indicators (GECIs) and imaging techniques enables recording of neuronal population activity at high speed and single-cell resolution. A biological BCI residing on the cortical surface allows straightforward connection to recording devices, an ECoG, microarrays or thin-film arrays.

For example, using genetically encoded calcium indicators such as pCAG-GCaMP7s-P2A-H2B-mRuby343, it is possible to interrogate L0 and assess whether it survives, integrates, and exhibits spontaneous activity. After neurons electroporated with a GECI were transplanted as L0 in a small mammal, cell counting and visualization of neural activity was assessed. Two days post transplantation, strong H2B-mRuby3 signal was visible in a mammal (e.g., mouse), which appeared as a thin band of cells on the cortical surface. The results indicated that the thickness of L0 doubled over the first two weeks of engraftment before stabilizing and maintaining thickness.

In certain instances, fluorescent images can be obtained using a confocal microscope. Fluorophores are excited using laser lines (e.g., 405, 488, 561 and 639 nm), with corresponding emission bandpass filters (e.g., of 420-480 nm, 495-550 nm, 573-615 nm and 607-750 nm). Widefield images are thereafter collected and processed.

In one aspect, 2 photon calcium imaging is utilized for neuronal imaging. The imaging laser source can be for example, a Mai Tai Ti:Sapphire laser (Spectra-Physics) mode locked at 920 nm for calcium imaging or at 1000 nm for structural imaging. Signals can be collected with a photomultiplier tube. The imaging system is computer controlled. Functional images can be acquired at 920 nm with ~50 mW average power. For developmental structural analysis, volumes can be acquired at 1250×1250 μm field of view covering 300 μm in Z with 2 μm steps. For imaging of spontaneous L0 events, a single 1250×1250 μm field of view was imaged at 30 Hz. For online BMI, a single plane 430×430 μm was imaged at 30 Hz. For neuronal morphology, images can be acquired from a 215×215 μm FOV.

In certain instances, stimulus-evoked fluorescence transients are observed for individual implanted cells and thereafter recorded. The fluorescently modified cells can detect single action potentials and can be imaged over a period of time. Co-expression of a second fluorescent cellular marker aids in detection of the fluorescent expressing calcium cells. Excitation of the transplanted calcium expressing cells modulate (input) and/or record (output) brain activity as a neural interface.

The calcium imaging methods disclosed herein allow tracking of a single neuron's activity of a subject over long time-lapse sequences in response to stimuli.

The engrafted BMI enables functional imaging of a mammal to characterize changes in spontaneous activity of L0. For example, the first calcium signals observed are large, infrequent population events that occur about one week after engraftment. Two weeks after engraftment, population events are more frequent, with localized spatial clustering. By four weeks after engraftment, spontaneous activity in L0 qualitatively resembled typical cortical activity, with generally asynchronous calcium signals that exhibit no apparent spatial structure. The results indicate that L0 survives transplantation onto the cortical surface, extends neuronal arbors, and undergoes developmental changes in spontaneous activity patterns from synchronous waves to decorrelated activity that resembles endogenous cortical activity.

In certain aspects, the cortical graft layer extends axons and dendrites into the cerebral cortex, striatum or completely integrating into the subject's brain. In certain aspects, the cortical graft layer forms synaptic connections to enable bidirectional communication, wherein the subject sends a response to an external device, and the device sends a response to the subject or vice versa.

In certain aspects, the cortical graft layer (L0) is engrafted over a lobe of the cerebral cortex such as the frontal lobe, the parietal lobe, the temporal lobe, the occipital lobe or a combination thereof.

In certain aspects, the cortical graft layer of cells has a thickness of about 50 microns to about 1 mm such as about 50 μm, 75 μm, 100 μm, 125 μm, 150 μm, 175 μm, 200 μm, 225 μm, 250 μm, 275 μm, 300 μm, 325 μm, 350 μm, 375 μm, 400 μm, 425 μm, 450 μm, 475 μm, 500 μm, 525 μm, 550 μm, 575 μm, 600 μm, 625 μm, 650 μm, 675 μm, 700 μm, 725 μm, 750 μm, 775 μm, 800 μm, 825 μm, 850 μm, 875 μm, 900 μm, 925 μm, 950 μm or about 1 mm. The L0 layer can be uneven with different thicknesses over the cortex.

In certain aspects, the BCI can be used to complete bidirectional communication. In one experiment, a neural cursor was defined as the difference between the mean activity of an ensemble of 'go' neurons (E1) and 'no-go' neurons (E2) in a BCI task for reward. Animals could not get rewards by simply increasing the mean activity of all neurons. In one aspect, this neural cursor is transformed into a stimulus (e.g., tone played back to the mammal) to provide information about the cursor value. The mammal must modulate the activity of the cursor to a threshold value within a timeframe (e.g., 30 seconds) to receive a reward; this counts as a 'hit' trial, whereas failure to gain a reward within the timeframe is considered a 'miss' trial, and triggers a timeout.

After receiving a reward, the mammal must modulate the neural cursor back to the baseline value to initiate another trial, such that the animal is required to move the cursor up and back down, and cannot gain rewards by maintaining the cursor in a reward zone.

In these experiments, engrafted mice performed above chance by day three, and maintained performance for the duration of the experiment. The calcium waveforms showed that rewards were associated with a large peak in E1 activity and a chronic suppression of E2.

In sessions where animals performed above criterion, they were able to rapidly achieve rewards at a rate well above chance early in the session and maintained high reward rates before a decrease after around 25 minutes, perhaps due to encroaching satiety. These results demonstrate that mice can volitionally control the activity of L0 neurons to perform a simple BCI task.

In certain aspects, the external stimulus is outside the mammalian brain and is a member selected from the group consisting of a light signal, an audio signal, and an electrical signal. In certain aspects, the external stimulus, which triggers a response, is outside the cell, but within the mammalian brain.

In certain aspects, the light signal has a wavelength of about 300 nm to about 1.5 microns such as about 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, 1050 nm, 1100 nm, 1150 nm, 1200 nm, 1250 nm, 1300 nm, 1350 nm, 1400 nm, 1450 nm, and/or 1500 nm.

In certain aspects, the detectable signal represents neuronal activity.

In certain aspects, the detectable signal connects to an external device such as a recording device and a device having a CPU.

In certain aspects, the mammal is a human.

In certain aspects, the human has an impairment selected from the group of an impairment of a motor skill, a sight function, an auditory function, a taste function and an olfactory function.

In a second aspect, the disclosure provides a method for bi-directional communication between a brain-computer interface (BCI) engrafted on a brain of a mammal and a computer, the method comprising:

providing a cortical graft layer comprising a plurality of neuronal cells transplanted on the brain's cerebral cortex of the mammal; and providing an external stimulus to the mammal wherein the plurality of cells engrafted on the brain respond to an external stimulus with a detectable neural signal.

Figure 1B:
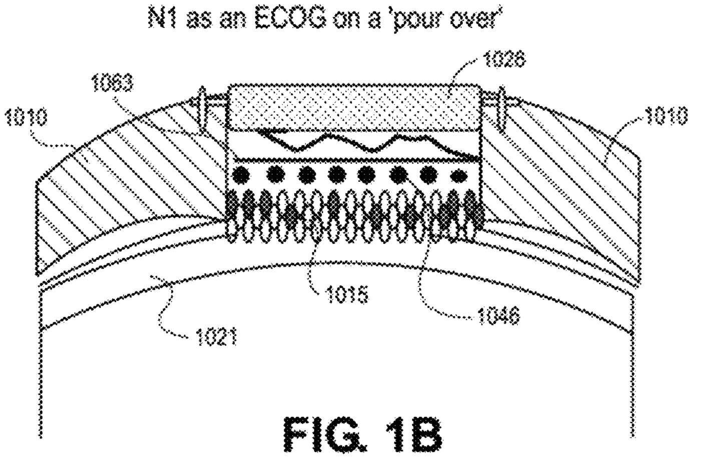

In addition to an optical approach, an electrical approach can be used to complete a BMI task in a mammal. The electrical approach eliminates the need for fluorescently labeled cells and an optical cranial window on the skull (or spinal cord, or cranial nerve). Turning now to FIG. 1B, one approach uses an electrocorticographic (ECoG) array 1028 that is placed flat on the cortex 1021, spinal cord, cranial nerve, or combination thereof on top of the deposited or poured-over 1015 cell layer (L0). This method establishes a direct link for transmitting information between the host brain cortex 1021 and the external ECoG array 1028. The ECoG 1028 measures cortical fields potentials using electrodes 1046 placed on the surface of the cortex 1021. The threads 1063 connect the ECoG 1028 to the electrodes 1063.

Figure 1C:
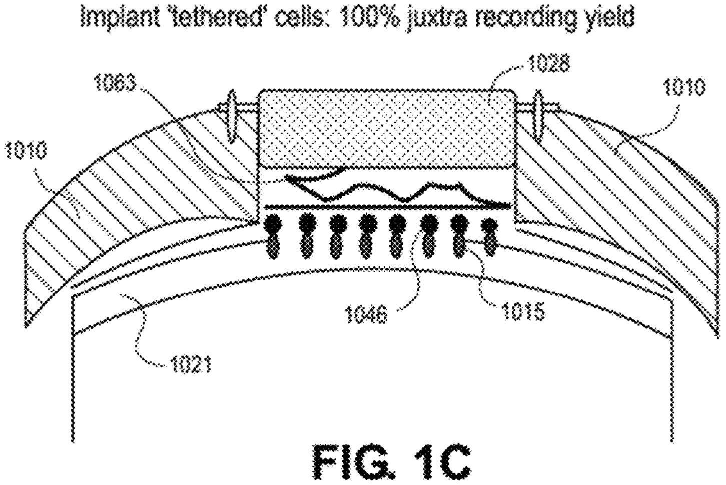

In another approach, as shown in FIG. 1C, an ECoG 1028 is implanted by a craniotomy into the skull 1010. Implanted neuronal cells 1015 are "tethered" to the electrodes 1046 of ECoG 1028 array prior to the implant surgery and placed flat on top of the cortex 1021. Advantageously, this approach leads to 100% juxtacellular recording yield.

Figure 1D:
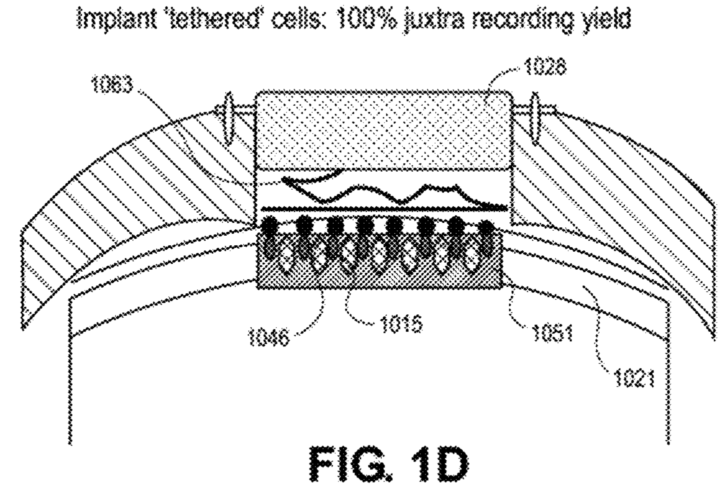

In still yet another approach, as shown in FIG. 1D, the implanted cells are tethered to a ECoG device, and the cells are cultured and deposited in an implantable hydrogel prior to surgery. Implanted neuronal cells 1015 are "tethered" to the electrodes 1046 of ECoG 1028 array prior to the implant surgery. The cells are packaged into hydrogel 1051 and inserted into the cortex 1021. The threads 1063 connect the ECoG 1028 to the electrodes 1063, which are connected to the hydrogel package 1051. This allows L0 cells to be placed and patterned in the optimal formation (with channels for vascularization and optionally with drugs embedded in the hydrogel that would release over time to help prevent inflammation, graft rejection, and scarring) for long term recording capabilities and guarantees a 100% juxtacellular recording yield.

In certain aspects, the hydrogel package is a hyaluronic acid-based hydrogel. The hydrogel package can contain a conductor, such as graphene or a graphene-like based material. Other conductors are known in the art. The package can be porous. The porous package can be formed over an electrode array.

In certain instances, the hydrogel package further comprises a solid substrate onto which the hydrogel package is cross-linked. In some instances, the hydrogel package comprises a cell medium comprising nerve growth factor (NGF) at a concentration from about 5 to about 20 picograms per milliliter.

In still another embodiment, the present disclosure provides a method of connecting a biological brain-machine interface with a subject, the method comprising:

depositing neuronal cells onto a cortical surface of a brain of a subject, the cells being selected to emit light or an electrical signal in response to a neural signal;

allowing the cells to form an additional cortical layer that grows and integrates into the brain; and recording light or an electrical signal emitted from the cells in response to a neural signal in the brain.

In still yet another embodiment, the present disclosure provides a method of stimulating a brain with a biological brain-machine interface, the method comprising:

depositing neuronal cells onto a cortical surface of a brain of a subject, the cells being selected to convert light or an electrical signal to an electrical signal compatible with neurons in the brain;

allowing the cells to form an additional cortical layer that grows and integrates into the brain;

directing light at or an electrical signal to the cells in the additional cortical layer such that the cells convert the light or the electrical signal to a neural signal; and measuring a response or a behavior of the subject correlated with the directed light or electrical signal.

External Device

In certain aspects, the electrocorticographic apparatus (ECoG) is a device that uses an electrode array, microarray or thin-film array placed directly on the exposed surface of a subject's brain to record electrical activity from the cerebral cortex. In certain aspects, the external ECoG device is disclosed in WO 2021/011401 to Seo. The application is drawn generally to a brain electrode implant system that includes one or more cylindrical sensors that fit flushly into burr holes in a subject's skull with wires that lead to a subcutaneous relay/router device behind the subject's ear. The relay communicates inductively with a device worn by the subject, which in turn communicates wirelessly or otherwise with a base station.

Each sensor nestled within its burr hole receives signals from a microfabricated polymer cable embedded with hundreds or thousands of metal electrodes descending into the subject's brain. The electrodes are implanted using a specialized surgical robot that pulls each electrode with a rigid needle into the brain during surgery before pulling out and pulling in another electrode. The received electrical signals, analog voltages and currents, are converted onboard the sensor to digital and then assessed. If an electrical signal denotes a neural spike or other interesting event, then it is multiplexed with other events and fed through a serial cable to the relay. The relay then transmits it off-board to the base station.

The implants are located in different lobes, or areas of the brain, to capture or stimulate targeted sections. The thin film electrodes merge into ribbon cable 204 at one end, which in turn is preconnected to the implant. Each implant is carefully set on top of the ribbon cable to cover the burr hole.

Physically, the sensor is a silicone- or other polymer-casted package that is molded into a cylindrical puck with a thin film of electrodes emerging from one end, and the wires to connect to the implanted router from the other. Inside the puck is a hermetic glass or other biocompatible material package containing electronics and thin film attached through vias or otherwise to a custom system on a chip (SoC).

In the exemplary embodiment, each sensor pill has 1,024 channels. Each array has 64 threads of 16 electrodes each. Every channel supports both stimulation and recording. The sensor's physical package is an 8 mm cylindrical "puck" that fits into an 8 mm drilled burr hole to sit flush with the surface of the skull.

In the exemplary system, there are no radios and batteries in the implant. If a patient takes off the pod device, then the implant loses power and he or she disconnects his or her implant from the outside. In an alternative embodiment, a small battery can be included in the implant.

Within each implant is circuitry, including integrated circuit (IC) chips, capacitors, and other components. The ICs receive from, and/or transmit to, the thin film electrodes that are surgically implanted within the subject's cranium. The ICs can include analog-to-digital converters (ADC) and/or digital-to-analog converters (DAC) in order to convert analog signals in the brain to or from digital signals of a computer.

The IC chips that include the ADCs can also include multiplexers/demultiplexers that multiplex digital signals together to put on the serial cable, or demultiplex serial signals from the serial cable apart for output to the DACs. The former is for reading out from the brain, while the latter is for stimulating the brain. Sitting in the burr hole, within the biocompatible housing, are a tight pack of electrical components. The components are carefully positioned to interface with the thin film ribbon cable of what may be thousands of individual, electrically isolated electrodes.

The leads and electrodes are manufactured using microelectromechanical systems (MEMS) technologies. The leads are manufactured monolithically with the hermetic package substrate and connect with electrodes. Each electrode site is oval and has a geometric surface area of ~370 $\mu m^2$ that is coated with a high surface area material.

Those of skill in the art will know of other ECoG devices useful in the present disclosure.

Methods of Use

The present disclosure can be practiced in various methods of use and treatment. The present methods comprise a step of administering a cellular composition for engraftment to a subject (e.g., a patient) to generate a L0 layer. Cellular engraftment generally encompasses transplantation of human or animal cells to a subject to generate a L0 layer or used to repair spinal cord injuries or aid patients with neurological disorders such as Alzheimer's disease, Parkinson's disease, paralysis, neurodegenerative conditions or epilepsy.

The present disclosure can be used in applications where it is useful to grow cells for a period of time for use in later cell engraftment for L0 generation or therapies. This can include for example, growing a patient's own cells for later transplantation, as well as for use in research or therapies. The disclosure includes the use of engrafted cells (e.g., neuronal cells) to ameliorate a neurodegenerative condition.

The present disclosure also provides methods for transplanting cells (e.g., neuronal cells) into a subject using cultured cells (e.g., neuronal cells) for transplantation. In some aspects, the transplanted cells (e.g., neuronal cells) are xenogenic to the non-human animal. In some aspects, the transplanted cells (e.g., neuronal cells) are human cells. Disclosed herein are methods for treating neurodegenerative disease including, but not limited to, Alzheimer's disease, Parkinson's disease, Huntington's disease or paralysis by transplantation of cells (e.g., neural cells).

The cells of the disclosure include cells that, upon transplantation or engraftment, generate an amount of neurons sufficient to integrate within the neuronal infrastructure of the brain, mammalian cortex, spinal cord, cranial nerve or a combination thereof, to ameliorate a disease state or condition or generate a L0 layer. Disclosed herein are methods including treating neurodegenerative diseases or conditions by transplanting cells (e.g., neuronal cells) isolated from a mammal such as the central nervous system of a mammal and that have been expanded in vitro. For example, transplantation of the neuronal cells can be used to improve ambulatory function in a subject suffering from spasticity, rigidity, seizures, or paralysis by generating a L0 layer.

A method of use and/or treatment can include supplying to an injured neural area, via transplantation, a suitable number of neuronal cells to attenuate defective neural circuits, including hyperactive neural circuits.

In one aspect, the disclosed method includes restoring motor function in a motor neuron disease. A suitable number or a therapeutically effective amount of cells (e.g., neuronal cells) can be provided to at least one area of neurodegeneration, such as a degenerative spinal cord, to restore motor function. The neuronal cells exert their therapeutic effect by replacing degenerated neuronal cells. In some aspects, the neuronal cells exert, their therapeutic effect by expressing and releasing trophic molecules which protect the neurons of the degenerating tissue so that more of them survive for longer period of time. Neuronal cells can be prompted to project into ventral roots and innervate muscle where they engage in extensive reciprocal connections with host motor neurons in subjects with degenerative motor neuron disease. Neuronal cells can be grafted into the lumbar cord where these cells can form synaptic contacts with host neurons and express and release motor neuron growth factors.

The disclosure includes providing neuronal cells that integrate with the host tissue and provide one or more growth factors to the host neurons thereby protecting them from degenerative influences present in the tissue. The methods include introducing a sufficient number of neuronal cells to an area of a spinal cord such that an effective amount of at least one growth factor is secreted by the neuronal cells.

The disclosure includes providing a method for using animal models in the preclinical evaluation of stem cells for cell replacement in neurodegenerative conditions.

The cells can be either undifferentiated, pre-differentiated or fully differentiated in vitro at the time of transplantation. In one aspect, the cells are induced to differentiate into neural lineage. The cells of the disclosure can undergo neuronal differentiation in situ in the presence of pro-inflammatory cytokines and other environmental factors existing in an injured tissue.

Using the disclosure, neural circuits can be treated by transplanting or introducing the cells into appropriate regions for amelioration of the disease, disorder, or condition. Generally, transplantation occurs into nervous tissue or non-neural tissues that support survival of the grafted cells. Neuronal cell grafts employed in the disclosure survive well in a neurodegenerative environment where the neuronal cells can exert powerful clinical effects in the form of delaying the onset and progression of neurodegenerative conditions or disease.

In some instances, transplantation can occur into remote areas of the body and the cells can migrate to their intended target. Accordingly, the disclosure can also include partial grafting of human neuronal cells. As used herein, the term "partial grafting" can refer to the implantation of expanded neuronal cells in only a portion of an area or less than an entire area of neurodegeneration. For example, partial grafting of human neuronal cells into the lumbar segments of spinal cord. At least a portion of the effects of neuronal cells on degenerating motor neurons include delivery of neurotrophies and trophic cytokines to degenerating host motor neurons via classical cellular mechanisms.

As used herein, a neurodegenerative condition can include any disease or disorder or symptoms or causes or effects thereof involving the damage or deterioration of neurons or the nervous system. The conditions which may be treated as disclosed herein may derive from traumatic spinal cord injury, ischemic spinal cord injury, traumatic brain injury, stroke, multiple sclerosis, cerebral palsy, epilepsy, Huntington's disease, amyotropic lateral sclerosis (ALS), chronic ischemia, hereditary conditions, or any combination thereof.

As disclosed herein, introducing a L0 layer or a therapeutically effective amount of the neuronal cell population may include transplanting or injecting at least a portion of the therapeutically effective amount into a plurality of areas of the recipient spinal cord. In one aspect, the method comprises treatment of neuropathic pain (e.g., neuropathic chronic pain).

The cell density for administration can vary from about 1,000 cells per microliter to about 1,000,000, cells per microliter such as 100,000, 200,000, 300,000, 400,000, 500,000, 600,000, 700,000, 800,000 900,000, or 1,000,000 cells/mL depending upon factors such as the site of the injection, the neurodegenerative status of the injection site, the minimum dose necessary for a beneficial effect, and toxicity side-effect considerations. In an aspect, the disclosure include injecting cells at a cell density of about 5,000 to about 50,000 cells per microliter.

The volume of media in which the expanded cells are suspended for delivery a treatment area can be referred to herein as the injection volume. The injection volume depends upon the injection site and the degenerative state of the tissue. More specifically, the lower limit of the injection volume can be determined by practical liquid handling of viscous suspensions of high cell density as well as the tendency of the cells to cluster. The upper limit of the injection volume can be determined by limits of compression force exerted by the injection volume that are necessary to avoid injuring the host tissue, as well as the practical surgery time.

EXAMPLES

Example 1—Preparation of BCI in Mice

Figure 1E:
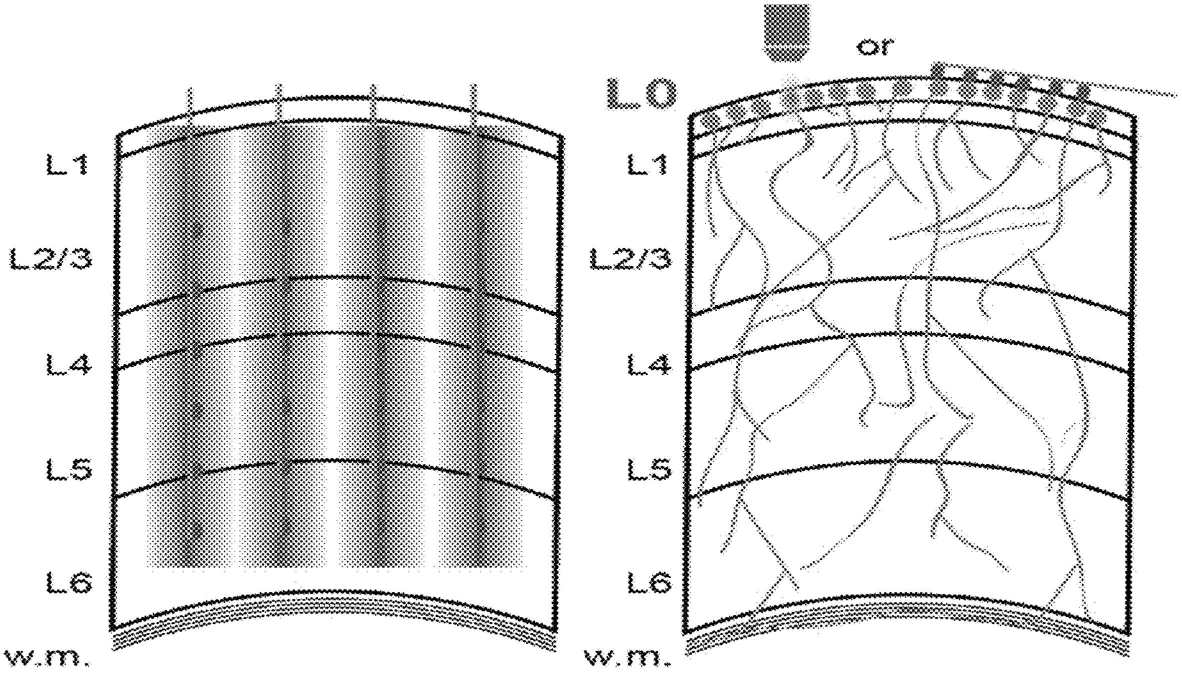
FIG. 1E is a schematic illustrating damage to the cortex done by penetrating electrodes (left) and an alternative scheme to transplant an artificial cortical L0 that is easily accessible to recording devices and non-traumatically penetrates the brain (right).

To test the possible usefulness of a BCI based on a biological interface, we attempted to train mice to perform BCI tasks using transplanted neurons. We reasoned that a biological BCI should reside on the cortical surface, allowing straightforward connection to recording devices (FIG. 1E). We therefore developed an experimental preparation to create an artificial cortical L0 above layer 1 (L1) by combining techniques for primary neural cell culture and cranial windows for 2P imaging in mice. To achieve this, mouse primary cortical neurons (E14-17) were isolated and electroporated with plasmid DNA, then deposited onto the cortical surface of adult mice. After waiting for cells to adhere to the cortex, we applied a glass coverslip to allow optical access to L0 to study its development, maturation, and function.

To determine electroporation efficiency, a subset of neurons were electroporated with DNA encoding a red fluorescent protein under a ubiquitous promoter and then cultured in an incubator instead of being transplanted. By image analysis, we estimate transfection efficiency to be ~11%. Non-electroporated plasmid DNA is digested by DNase before transplantation, eliminating the possibility of off-target expression and ensuring that we are recording only from engrafted cells.

Example 2—Microscopic Imaging of Neuron Growth and Activity

Figure 1F:
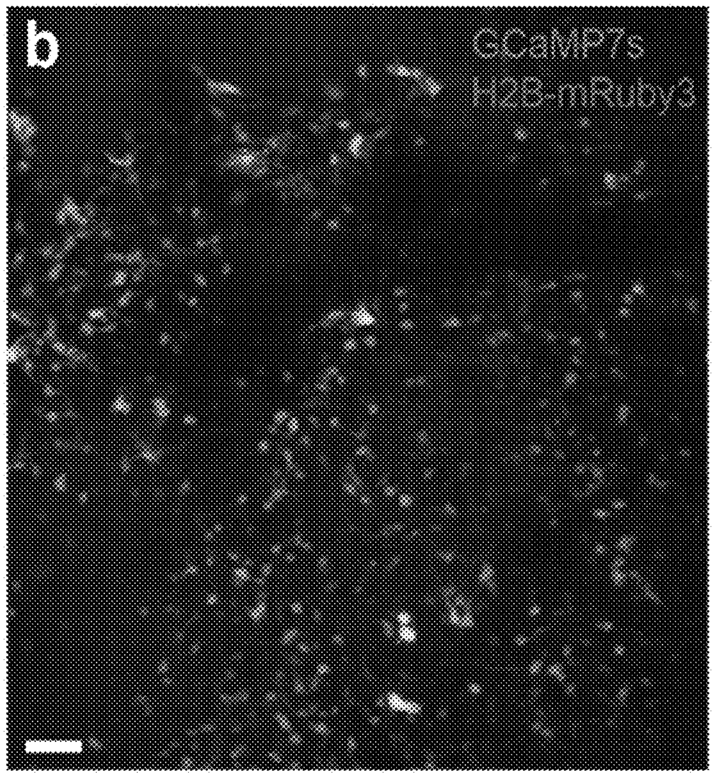
FIG. 1F is an example 2P image of L0 3 days after engrafting. Cells are electroporated with pCAG-GCaMP7s-P2A-H2B-mRuby3. Scale bar is 100 μm.
Figure 1G:
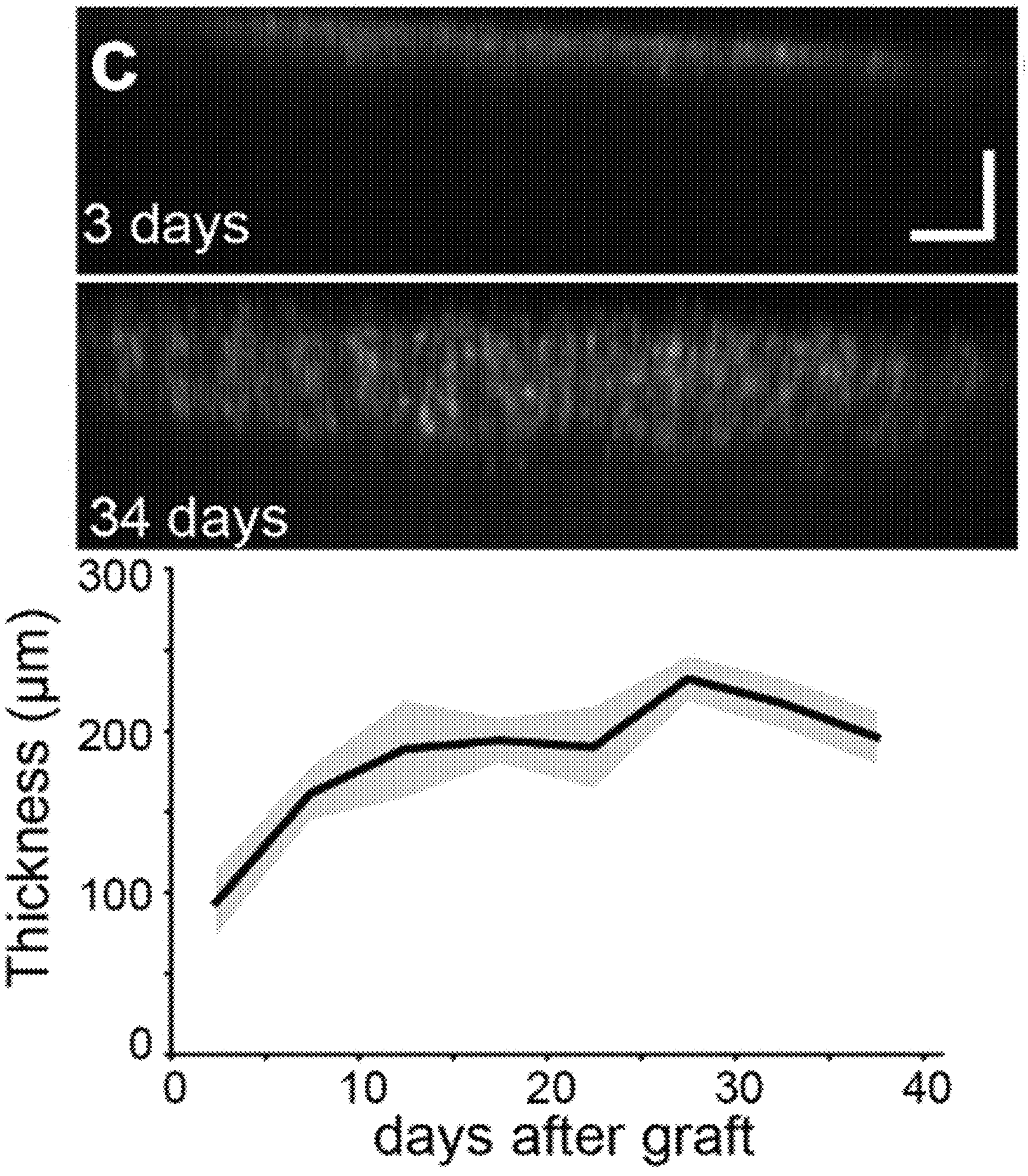
FIG. 1G is an example XZ projections of L0 3 (top) and 34 (middle) days after engraftment (red: H2B-mRuby3, green: GCaMP7s). Bottom, graph showing thickness of L0 versus days after engraftment (n=11 mice). X and Z scale bars are both 100 μm. Data are the mean±s.e.m. of all observations from n=11 mice in a five day sliding window.

We first asked if L0 survives, integrates, and exhibits spontaneous activity. We therefore transplanted neurons electroporated with pCAG-GCaMP7s-P2A-H2B-mRuby3 to allow for cell counting and visualization of neural activity. We periodically imaged the awake, head-fixed mice on a circular treadmill under a 2P microscope. Strong H2B-mRuby3 signal was visible ~2 days after transplantation, allowing us to identify a thin band of cells on the cortical surface (FIG. 1F). The thickness of L0 doubled over the first two weeks of engraftment before stabilizing and maintaining thickness throughout our experiments (FIG. 1G, day 3: 94±20 μm, day 18: 194±14 μm, $p=0.001$, Kruskal-Wallis Test). We next looked for evidence of cell death by quantifying the number of red nuclei per field of view over time. We did not observe any evidence of decreasing cell numbers, but instead found a nonsignificant trend for an increased number of labelled neurons over time. This apparent increase in the number of labelled cells could be explained by a constitutively active promoter driving an increase in average red fluorescence values, since weakly expressing neurons may emerge from the noise floor. However, we cannot eliminate the possibility that a small progenitor population was electroporated and divided post-engraftment.

Example 3—Calcium Imaging

Figure 1H:
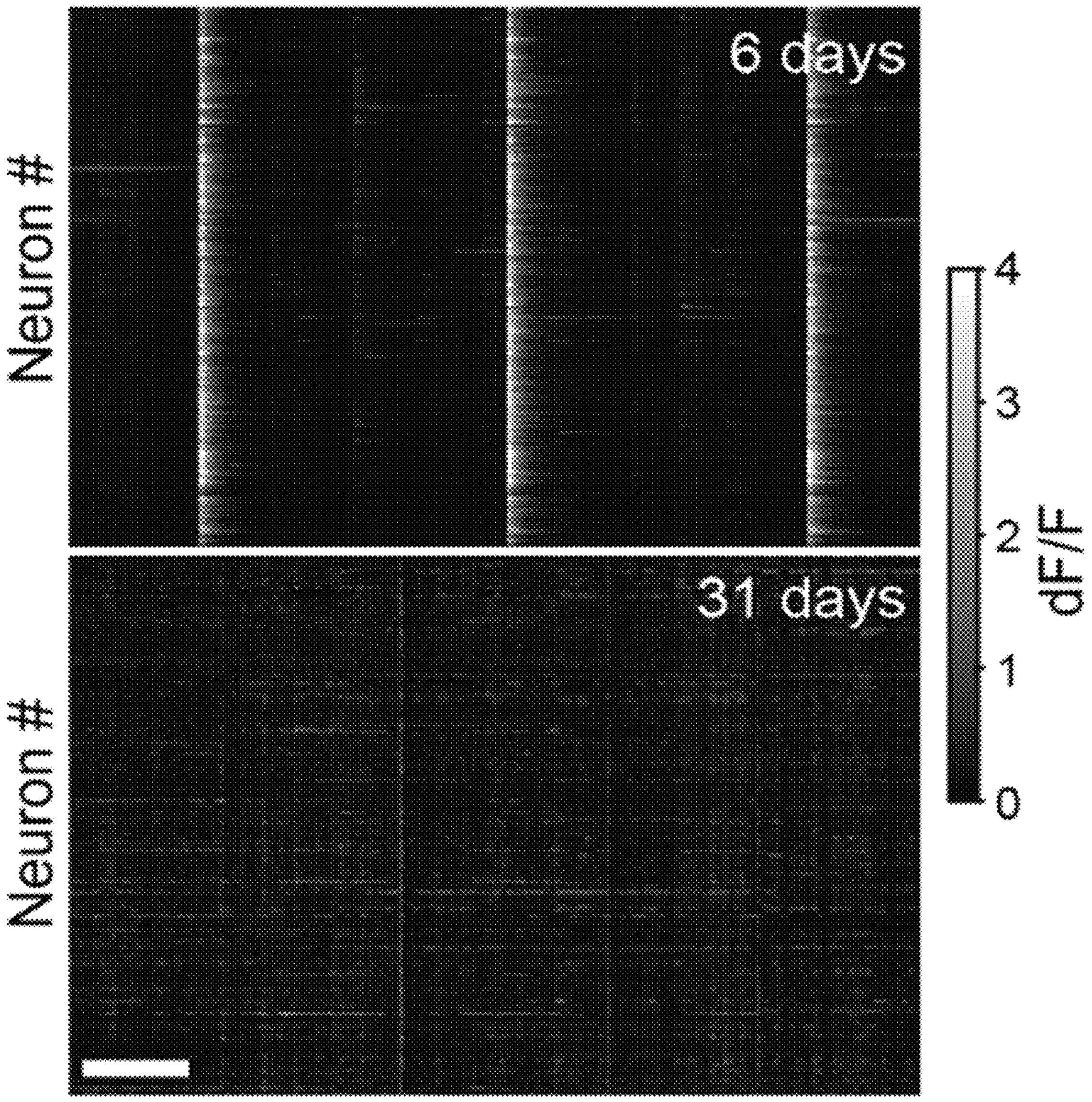
FIG. 1H is a representative raster plots of spontaneous activity from L0 neurons 6 (top) or 31 (bottom) days after engraftment. Graphs show dF/F for neurons (y-axis) vs time (x-axis). Scale bar is 1 minute.
Figure 1I:
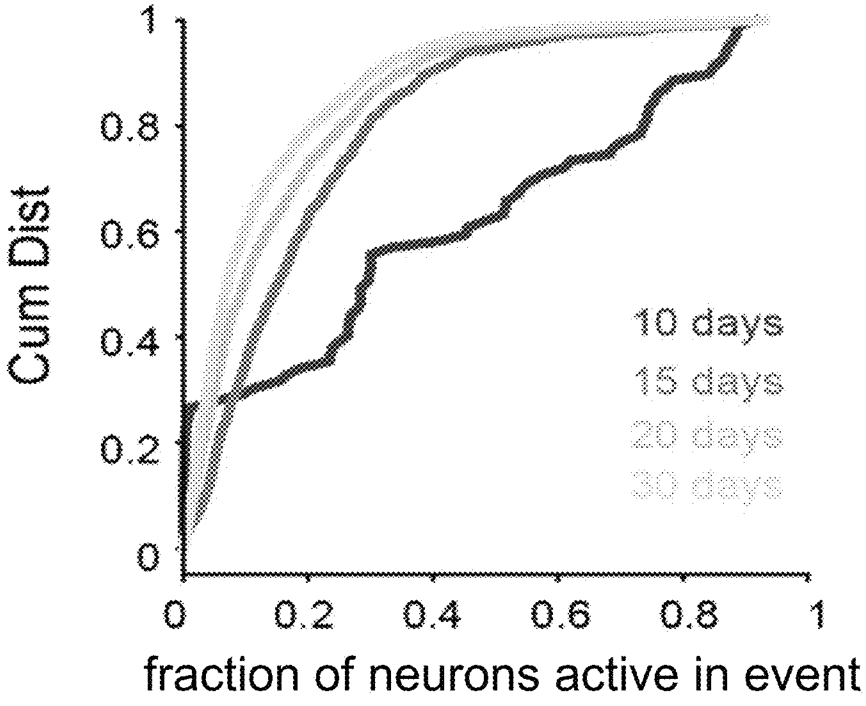
FIG. 1I is a cumulative distribution showing the fraction of neurons active in each population event. Shaded bars denote events from different time periods after analysis. Data represent events from n=11 mice.
Figure 1J:
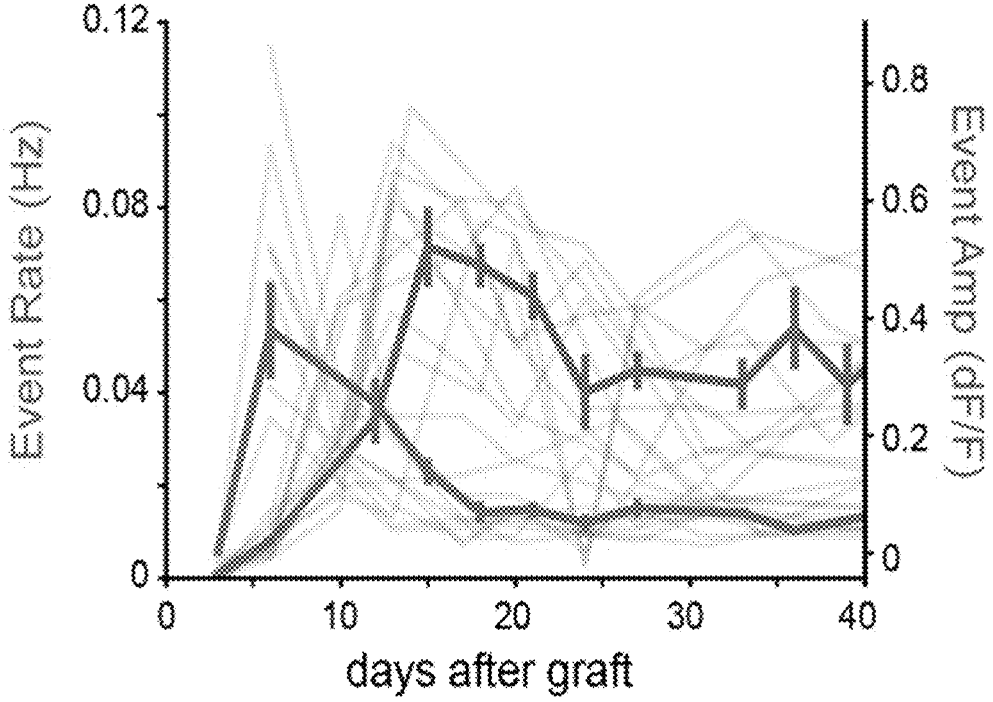
FIG. 1J is a graph showing the L0 population event rate (Hz, green) versus event amplitude (purple, dF/F) over time. Thick lines indicate mean±s.e.m. of all observations from n=11 mice in a five day sliding window.
Figure 1K:
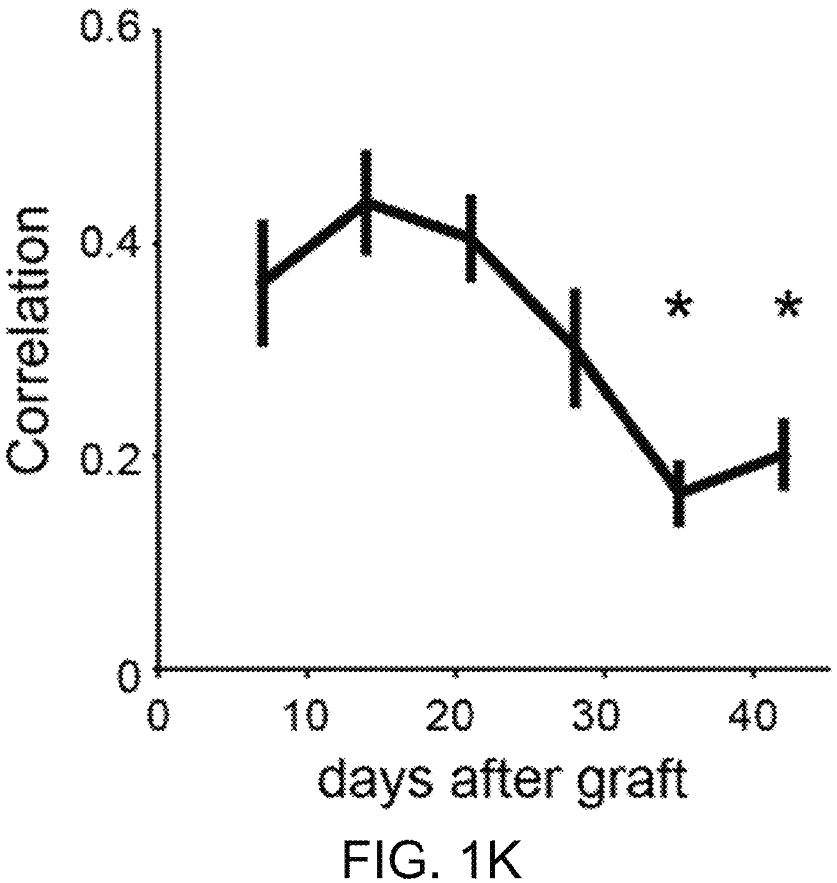
FIG. 1K is a graph showing the mean pairwise correlation of L0 neurons over time. Data are the mean±s.e.m. of n=11 mice (* indicates p<0.05, Kruskal-Wallis with Dunn's post-hoc test).
Figure 1L:
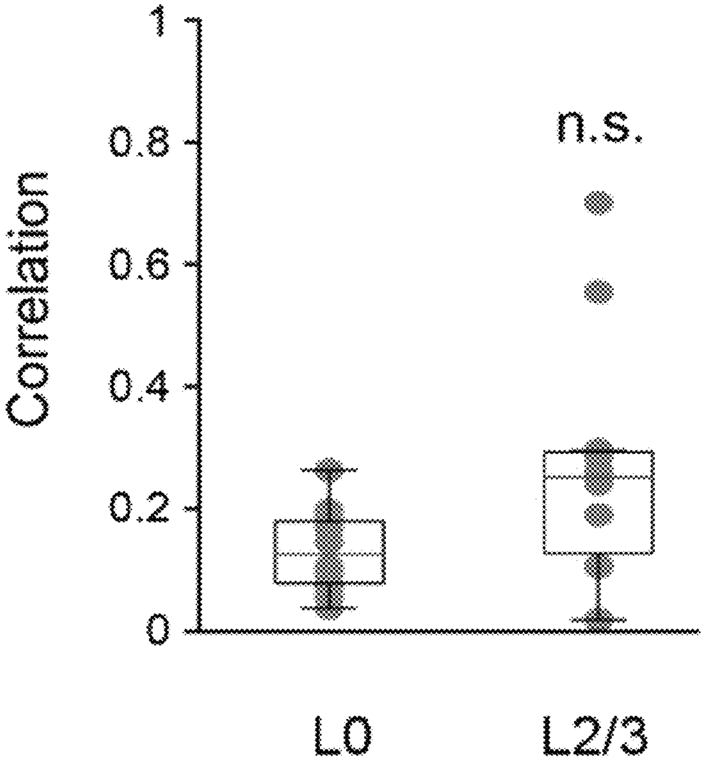
FIG. 1L is a boxplot of the mean pairwise correlation of neurons in L0 (left—electroporated GCaMP7s, n=11 mice) or L2/3 (viral GCaMP6s, n=9 mice) before the first behavioral training session (p=0.053, two-sided t-test).

We also performed functional imaging to characterize changes in spontaneous activity of L0 after engraftment. The first calcium signals we observed were large, infrequent population events that began around one week after engraftment (FIG. 1H). Two weeks after engraftment, population events were more frequent, but the entire layer no longer fired synchronously. Instead activity exhibited more localized spatial clustering. By four weeks after engraftment, spontaneous activity in L0 qualitatively resembled typical cortical activity, with generally asynchronous calcium signals that exhibited no apparent spatial structure (FIG. 1H). To quantify the evolution of spontaneous activity over the development of L0, we identified population events using the rise of the calcium transients on the full-field fluorescence. Population events in the first 10 days after engraftment tended to involve a large fraction of cells (30±31% of all cells active per event, med±s.d.). These events significantly sparsened 10 days later (7±15% of all neurons active per event, med±s.d, $p<1\times10\text{-}15$ KS-test, FIG. 1I). Conversely, early in the graft, individual neurons participated in the majority of population events (active in 66±29% of events, med±s.d), but 10 days later they were active during significantly fewer events (27±34% med±s.d., $p<1\times10\text{-}16$ KS-test). Quantifying the mean frequency and amplitude of population events revealed a switchover from large, infrequent events to small and rapid events in L0 that occurred 12-14 days after engraftment, matching reports of similar changes in visual cortex around the same time after onset of sensory experience (FIG. 1J). This sparsification of population events in L0 occurred concomitantly with a significant decrease in the mean pairwise correlation of L0 neurons by one month of engraftment ($p=0.0013$, Kruskal-Wallis with Dunn's post-hoc test, FIG. 1K). Mean pairwise correlation of mature grafts during spontaneous activity was similar to or slightly below correlations found in spontaneous activity in layer 2 (FIG. 1L, $p=0.053$, two-sided t-test).

Example 4—BCI Morphology

To assess the morphology of engrafted L0 neurons during this period, we sparsely labeled neurons with mRuby3, allowing visualization of neurites during development using 2P imaging (FIGS. 6A-6E). These images revealed that neurons extended processes as soon as three days after engraftment. Sholl analysis on traced neurites revealed that the complexity of dendritic and axonal arbors increased over time and stabilized by 2 weeks, in advance of the maturation of firing patterns (FIGS. 6A-6E). Together, this data shows that L0 survives transplantation onto the cortical surface, extends neuronal arbors, and undergoes developmental changes in spontaneous activity patterns from synchronous waves to decorrelated activity that resembles endogenous cortical activity.

Example 5—BCI Integration, Function, and Sensitivity

Figure 6A:
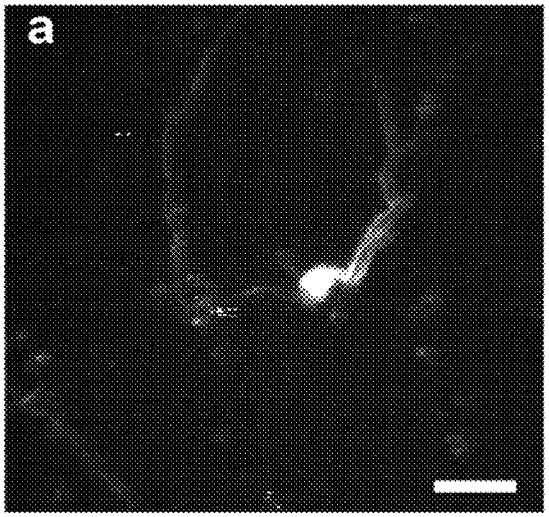
FIGS. 6A-6C show maximal intensity projections of example neurons labeled with mRuby3 1 (Supp. 4a), 2 (Supp. 4b), or 4 (Supp. 4c) weeks after engraftment. Scalebars in each image are 10 μm.
Figure 6B:
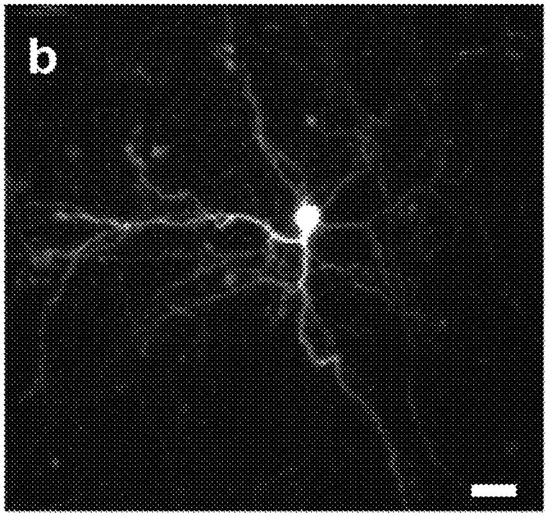
Figure 6C:
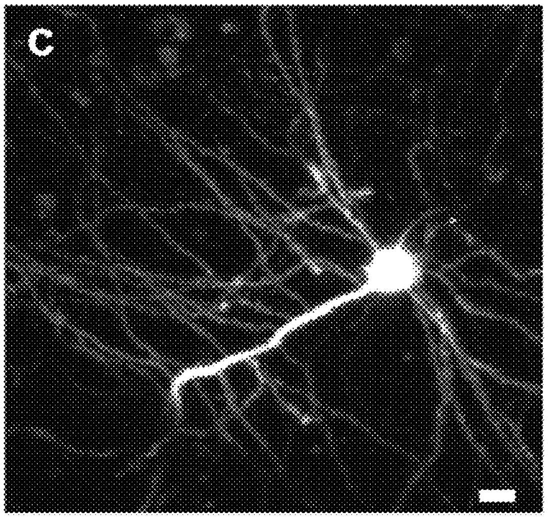
Figure 6D:
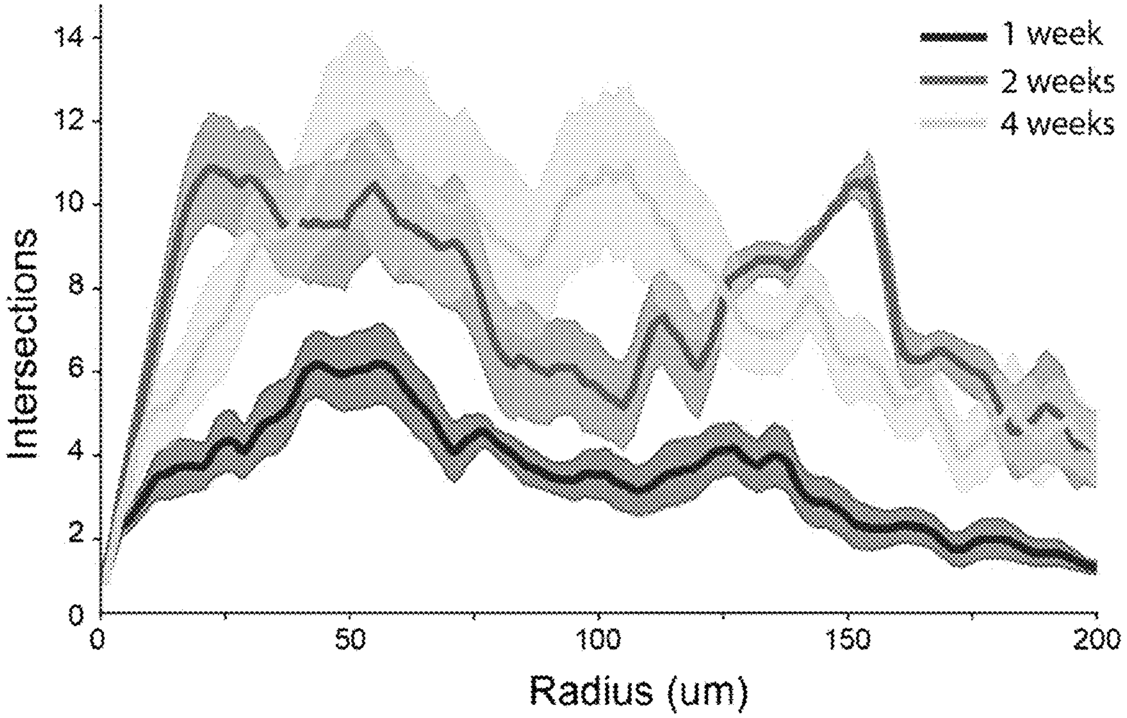
FIG. 6D shows a Sholl analysis of traced dendritic arbors from engrafted neurons, 1, 2 or 4 weeks after engraftment. Data represent the mean and s.e.m. from n=8, 9, and 7 neurons (1, 2, 4 weeks) from N=2 mice.
Figure 6E:
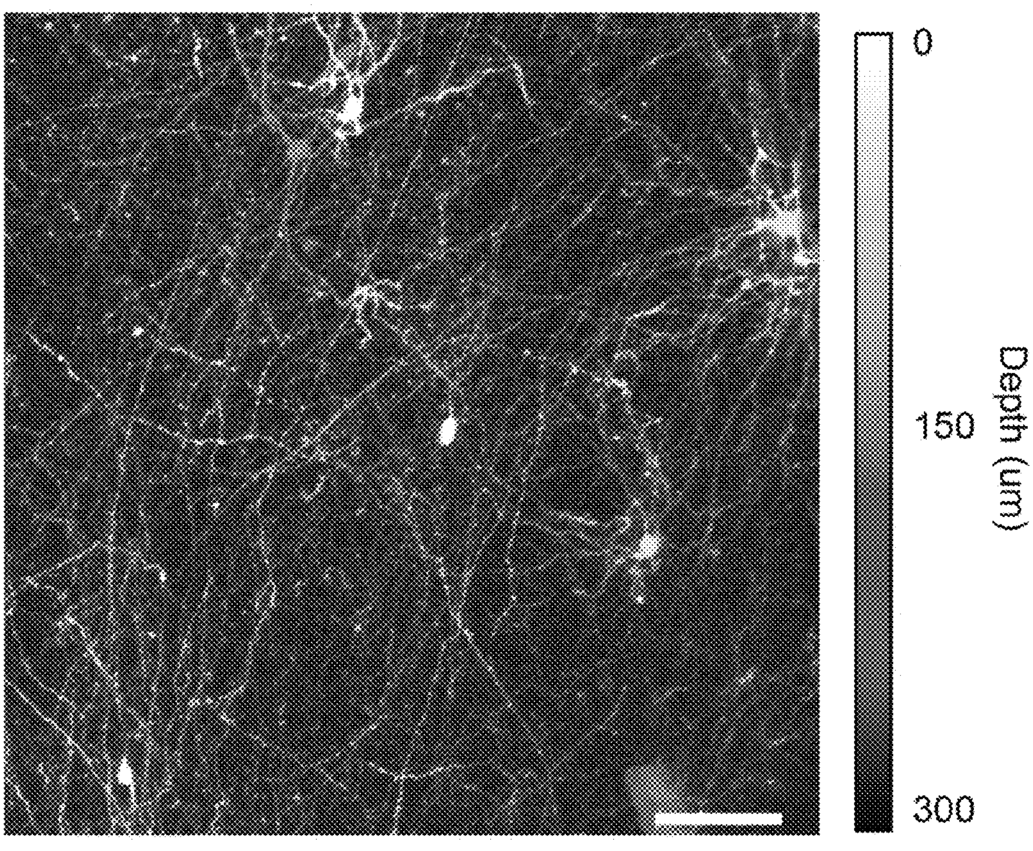
FIG. 6E shows a depth-coded maximal intensity projection of a zoomed out field of view from an example mouse 4 weeks after engraftment. Scale bar is 100 μm.

Having established the viability of the graft, we sought to test the degree to which L0 integrated into the host cortex. Structural 2P imaging revealed neurites descending from the cell body, hinting at functional integration of L0 with the host cortex (FIG. 6E). We reasoned that the best way to tell if the graft integrated enough to allow for a useful BCI was to directly attempt to use it for that purpose. We therefore leveraged previous demonstrations of a rodent BCI task using 2P imaging where the animal is operantly conditioned to modulate neural activity for water rewards, and asked if the mice could use the engrafted cortical layer to complete this task.

Figure 7A:
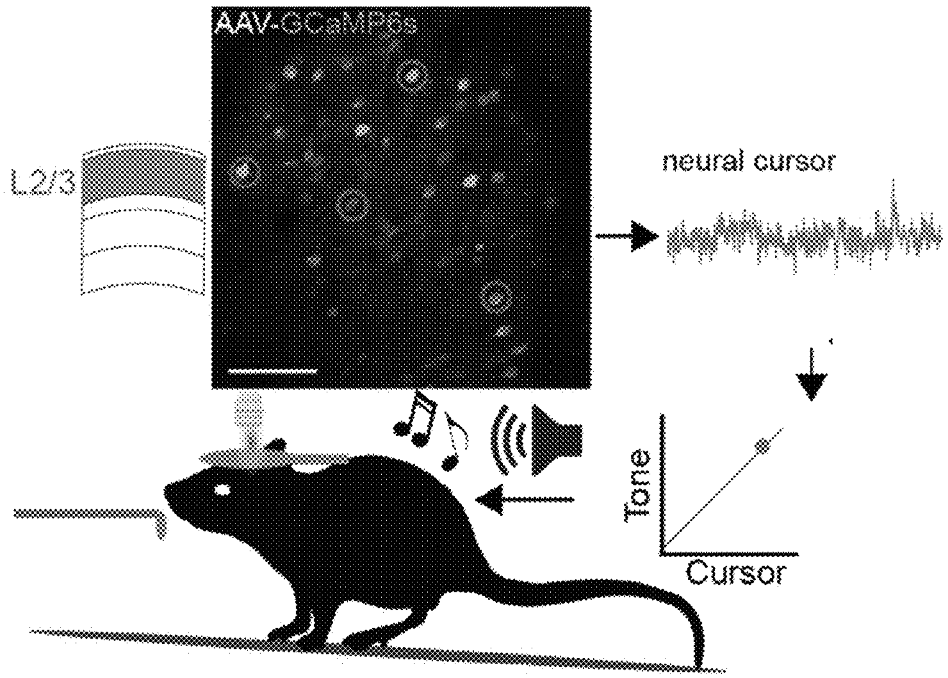
FIG. 7A is a schematic illustrating an optical BMI task where calcium signals from L2/3 are transformed into a neural cursor corresponding to a tone which is played back to the animal. A water reward is administered when the cursor hits a threshold level. Image is the field of view used for the representative experiment in FIG. 7D. Green is AAV-GCaMP6s. The magenta circles indicate E1 ensemble neurons and the green circles indicate E2 ensemble neurons. Scale bar is 100 μm.

To validate the behavior in our hands, we first performed control experiments using wild type mice virally expressing GCaMP6 in layer 2 (depth: 136±26 μm, FIG. 7A). As in previous reports, we defined a neural cursor as the difference between the mean activity of an ensemble of 'go' neurons (E1) and 'no-go' neurons (E2) so that animals could not get rewards by simply increasing the mean activity of all neurons. This cursor is transformed into a tone played back to the mouse to provide information about the cursor value. The mouse must modulate the activity of the cursor to a threshold value within 30 seconds to receive a water reward; this counts as a 'hit' trial, whereas failure to gain a reward within 30 seconds is considered a 'miss' trial, and triggers a timeout. After receiving a reward, we required that the animal modulate the neural cursor back to the baseline value to initiate another trial, such that the animal must move the cursor up and back down, and cannot gain rewards by maintaining the cursor in a reward zone.

Figure 7B:
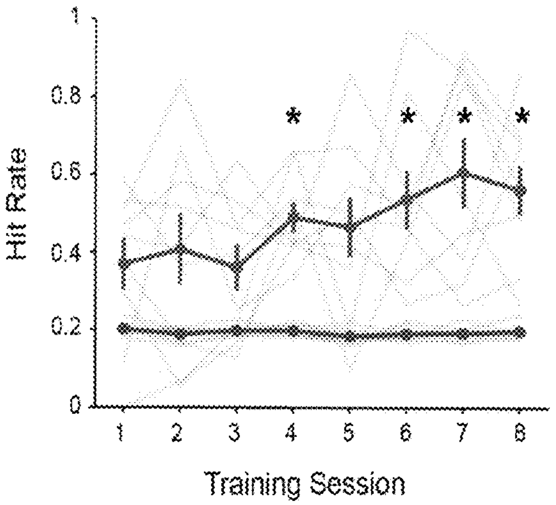
FIG. 7B shows behavior performance of wt mice over 8 sessions (x-axis). Hit rate (green) versus chance (purple) is plotted for n=9 mice. Solid lines indicate mean±s.e.m., * indicates $p<0.05$ (Wilcoxon signed-rank test with Bonferroni post-hoc correction).
Figure 7C:
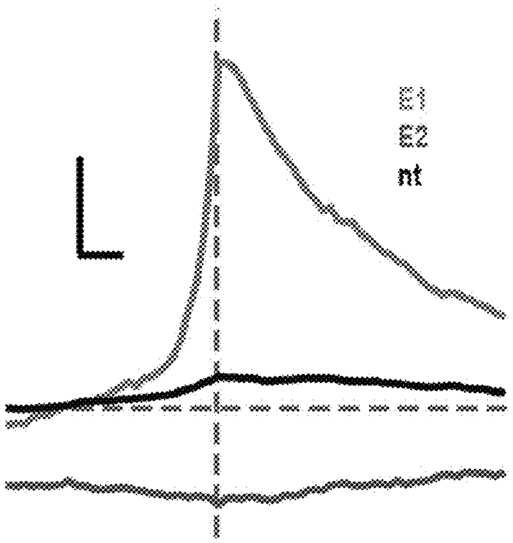
FIG. 7C shows a reward-triggered grand average of neurons in E1 (magenta), E2 (green), or non-target neurons (black). Scale bar are 0.2 dF/F and 200 ms. Dashed red lines indicate reward time (vertical) and 0 dF/F (horizontal).
Figure 7D:
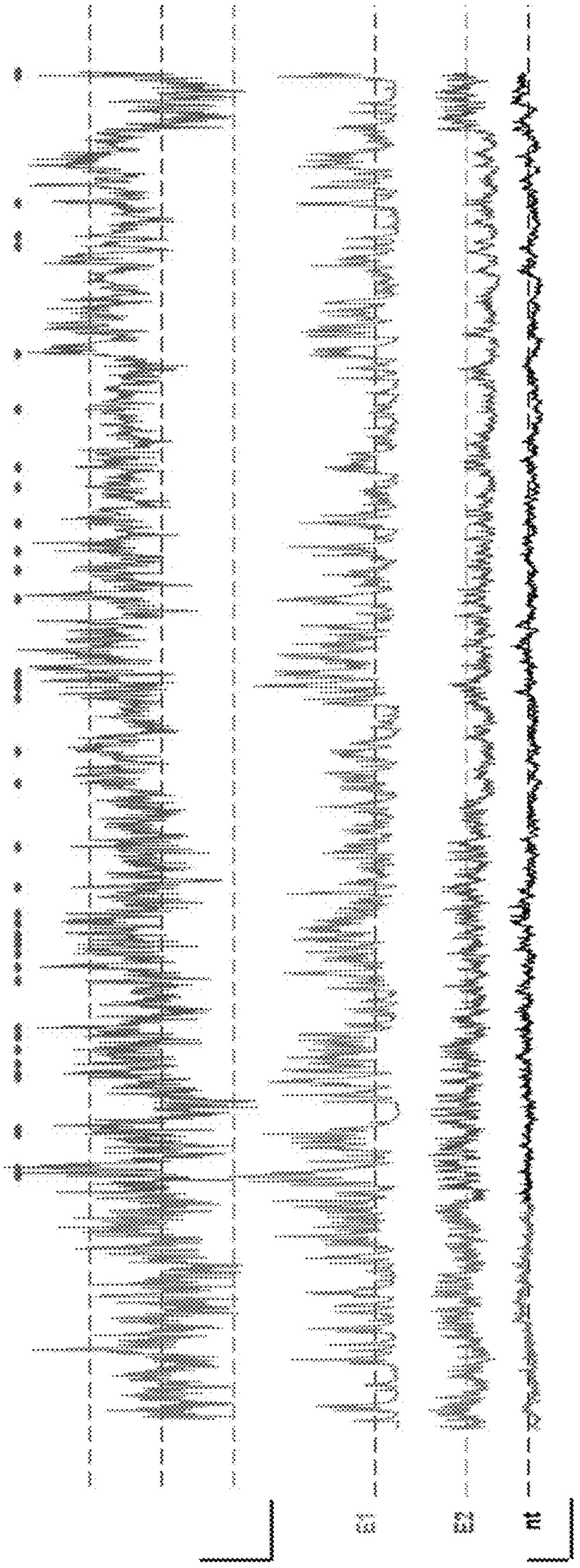
FIG. 7D shows calcium signals from an example behavior session from neural cursor (top, blue), E1 (magenta), E2 (green), and non-target neurons (bottom, black). Baseline period is colored gray. For the neural cursor, dashed black line indicates mean value and dashed red lines indicate positive and negative reward thresholds. Red dots indicate when rewards were administered. For ensembles, dashed black line indicates dF/F=0. Scalebars are 5 mins and 100% dF/F.

In our hands, mice using L2 neurons to control a neural cursor performed above chance on their fourth day of training, and after a regression on the fifth day performed above chance for the remainder of the training sessions (FIG. 7B, $p<0.05$ hit-rate versus chance, Wilcoxon signed-rank test with Bonferroni post-hoc correction). As in previous reports, a reward-triggered average of ensemble activity showed that rewards were achieved by a large increase in E1 activity that began one second before reward, coupled with long-term suppression of E2 that occurred gradually over the session and was not time-locked to rewards (FIGS. 7C and 7D).

Figure 2A:
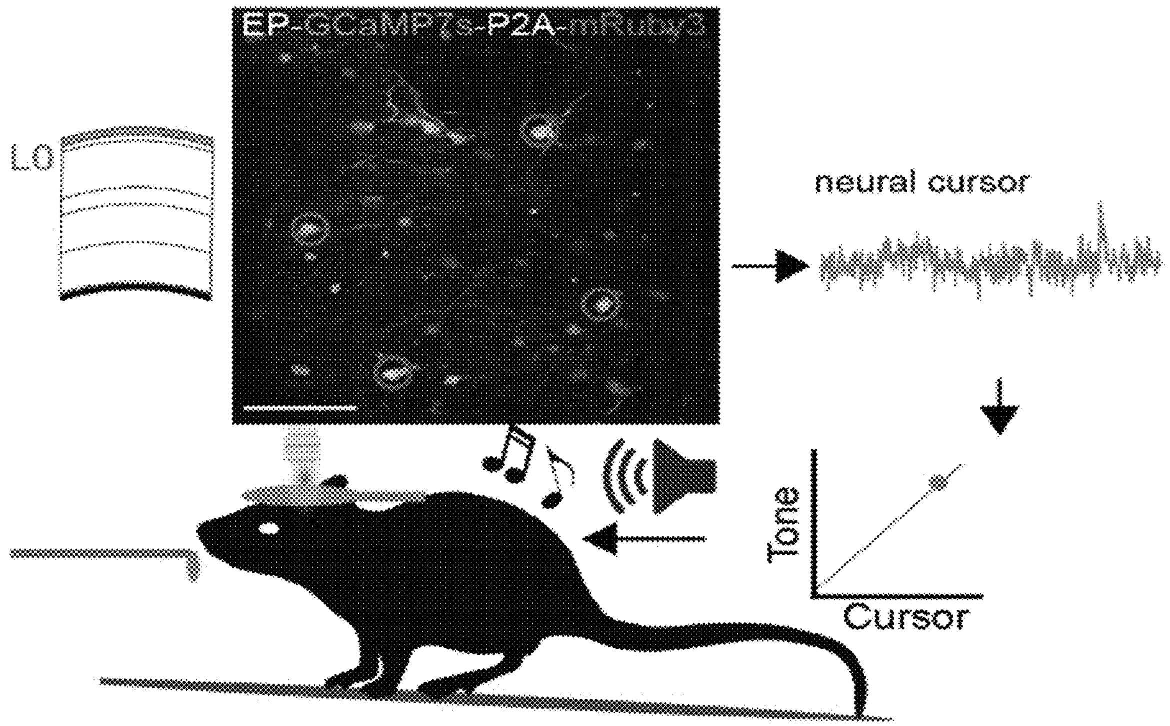
FIG. 2A is a schematic illustrating optical BMI task where calcium signals from L0 are transformed into a neural cursor corresponding to a tone which is played back to the animal. A water reward is administered when the cursor hits a threshold level. Image is the field of view used for the representative experiment in FIG. 2D. Green in GCaMP7s and red is H2B-mRuby3. The magenta circles indicate E1 ensemble neurons and the green circles indicate E2 ensemble neurons. Scale bar is 100 μm.
Figure 2B:
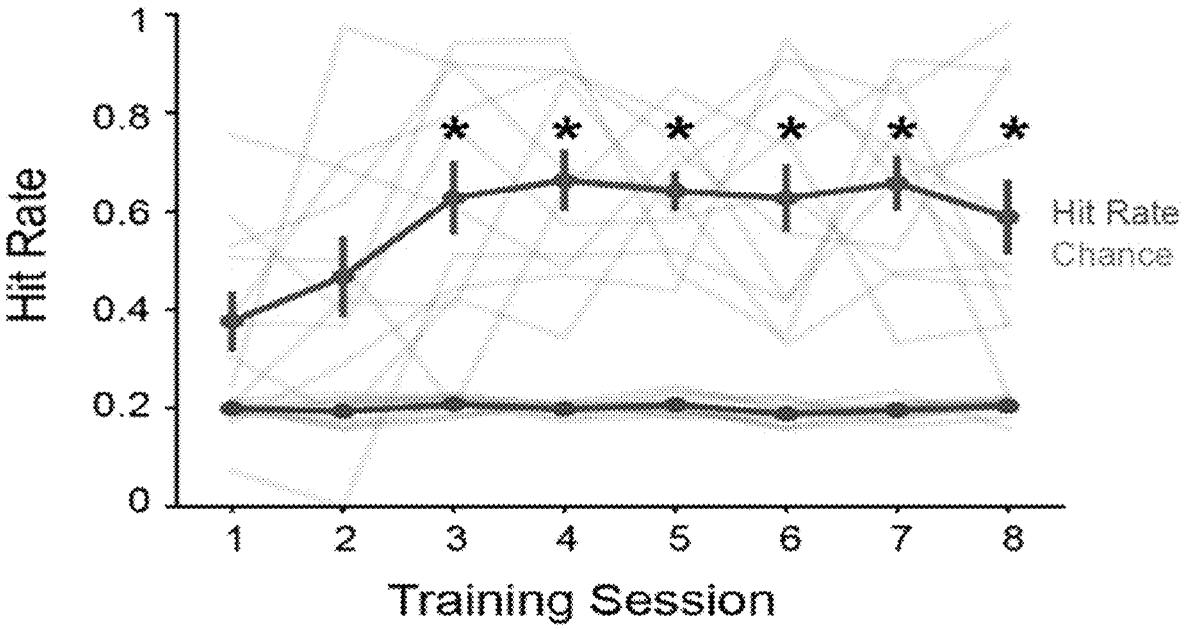
FIG. 2B is a behavior performance of L0 engrafted mice over 8 sessions (x-axis). Hit rate (green) versus chance (purple) is plotted for n=11 mice. Solid lines indicate mean±s.e.m., * indicates p<0.05 (Wilcoxon signed-rank test with Bonferroni post-hoc correction).
Figure 2C:
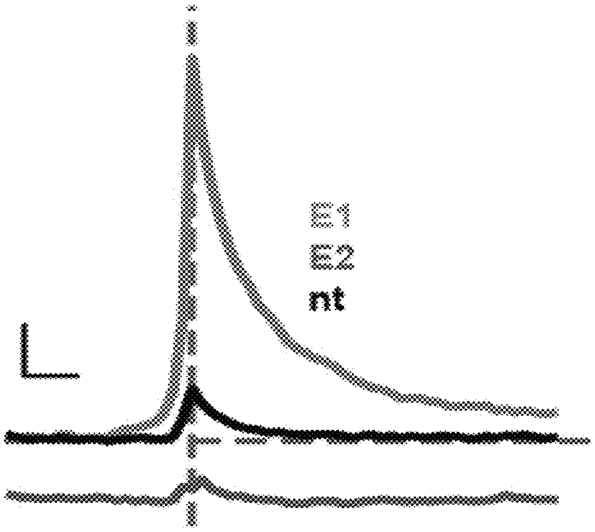
FIG. 2C is a reward-triggered grand average of neurons in E1 (magenta), E2 (green), or non-target neurons (black). Scalebars are 0.2 dF/F and 200 ms. Dashed red lines indicate reward time (vertical) and 0 dF/F (horizontal).
Figure 2D:
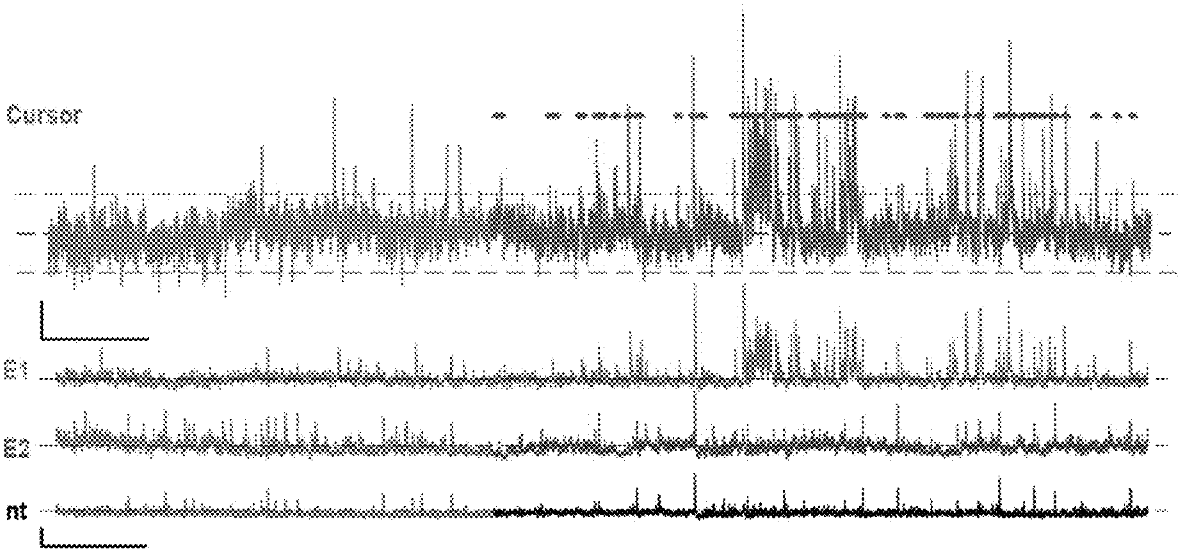
FIG. 2D charts calcium signals from an example behavior session from neural cursor (top, blue), E1 (magenta), E2 (green), and non-target neurons (bottom, black). Baseline period is colored gray. For the neural cursor, dashed black line indicates mean value and dashed red lines indicate positive and negative reward thresholds. Red dots indicate when rewards were administered. For ensembles, dashed black line indicates dF/F=0. Scale bars are 5 mins and 100% dF/F.

Having validated the calcium-imaging BCI task in wild-type mice, we asked if engrafted mice could volitionally control the activity of L0 neurons for rewards (FIG. 2A). Engrafted mice performed above chance by day three, and maintained performance for the duration of the experiment (FIG. 2B, $p<0.05$ hit-rate versus chance, Wilcoxon signed-rank test with Bonferroni post-hoc correction). As with control mice, a reward-triggered average of calcium waveforms showed that rewards were associated with a large peak in E1 activity and a chronic suppression of E2. Unlike control mice, in L0 mice, both E2 and non-target neurons exhibited a small peak in fluorescence time-locked with the reward (FIGS. 2C and 2D). This effect may result from contamination of calcium sources with fluorescence from axons and dendrites, which were much more prominent in L0 than L2. This is likely due to the sparse transfection of L0 and the increased signal-to-noise due to lack of scattering and improved GCaMP variant (FIGS. 2C and 2D).

Figure 2E:
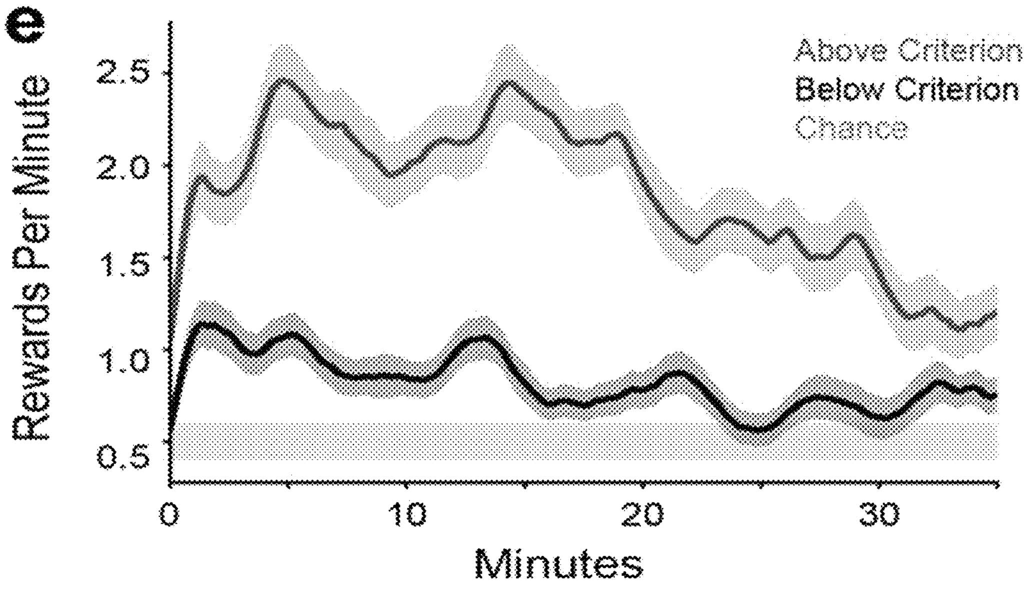
FIG. 2E charts a running average of rewards per minutes for trials in which animals hit criterion (green) or failed to hit criterion (black). Rewards per minute at chance performance is highlighted in magenta. Data represent the mean±s.e.m. of 40 sessions (above criterion) and 46 (below criterion) sessions from n=11 mice.
Figure 2F:
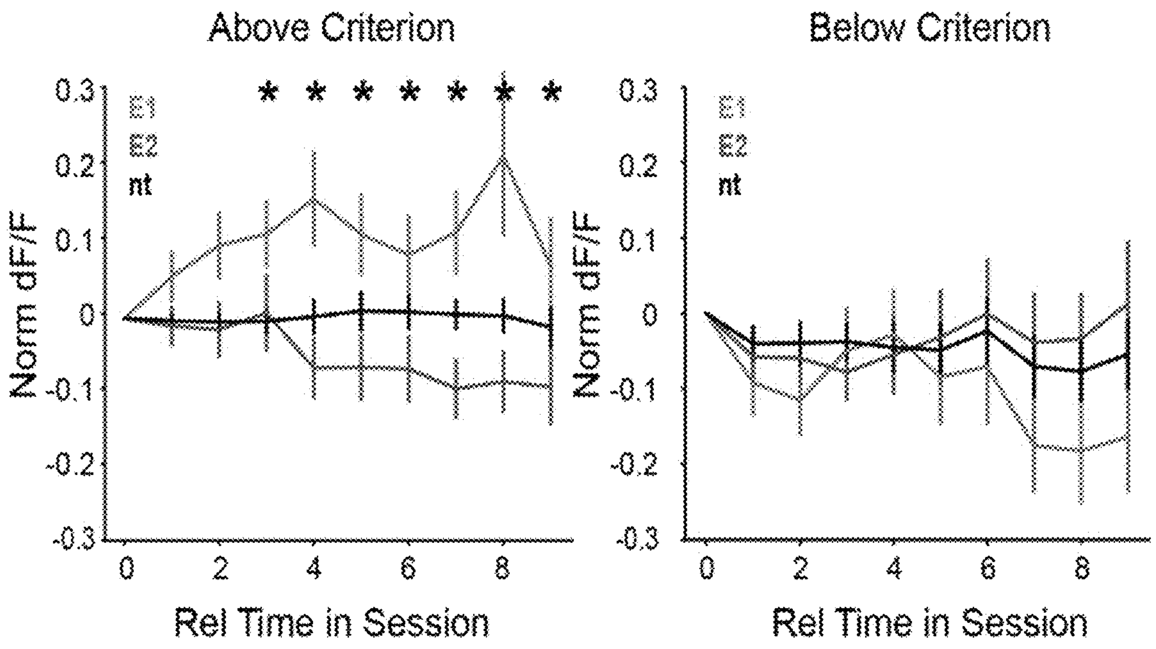
FIG. 2F is a graph showing dF/F normalized to trial start for trials where the animal performed above criterion (left) and where it did not (right) over relative time in the trial. Data represent the mean±s.e.m. of 40 above criterion (left), and 46 sessions below criterion (right) from n=11 mice for E1 (magenta), E2 (green), and non-target neurons (black). * indicates p<0.05 (two-way RM-ANOVA).
Figure 7E:
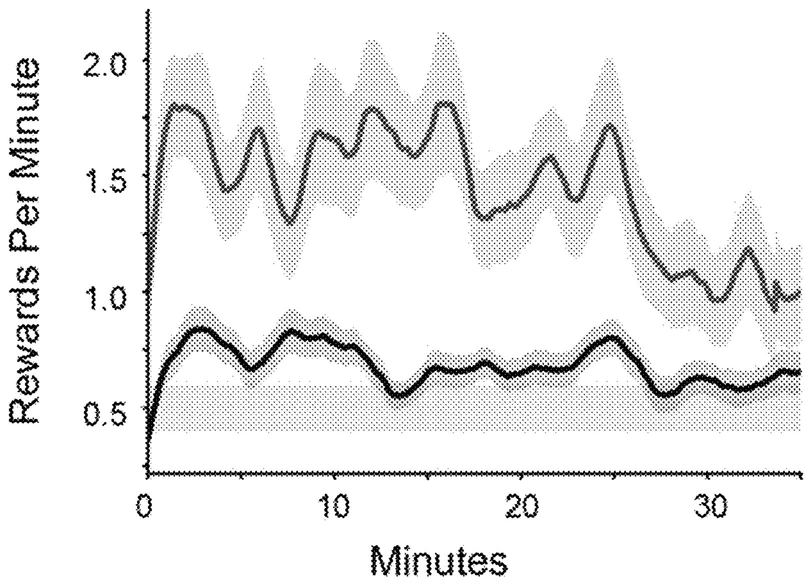
FIG. 7E shows a running average of rewards per minutes for trials in which animals hit criterion (green) or failed to hit criterion (black). Rewards per minute at chance performance is highlighted in magenta. Data represent the mean±s.e.m. of sessions from n=9 mice.

In sessions where animals performed above criterion, they were able to rapidly achieve rewards at a rate well above chance early in the session and maintained high reward rates before a decrease after around 25 minutes, perhaps due to encroaching satiety (FIG. 2E). In contrast, for sessions where animals failed to hit criterion, average reward rates showed a modest increase and were maintained slightly above chance for the duration of the session. This suggests that overall success depended upon the animal's ability to rapidly learn the mapping between neural activity and cursor value early in a session (FIG. 2E). Similar results were observed with control mice (FIG. 7E), suggesting that our task design, rather than the use of L0, encouraged dependence on rapid formation of associations. We next asked if the change in fluorescence of the target ensembles over the course of a session reflected the mouse's behavior. Non-target neurons on average did not change brightness, whereas E1 neurons began increasing early, and were significantly above the E2 neurons for the last 70% of the session ($p<0.05$ repeated measures ANOVA with Tukey's test). This rise in E1 fluorescence preceded the persistent suppression of E2 neurons, which began 40% through the session (FIG. 2F). These changes were only apparent in trials where the animal learned; in sessions where the animal failed to achieve criterion, there was no significant difference between ensemble fluorescence (FIG. 2F).

Figures 2G, 2H:
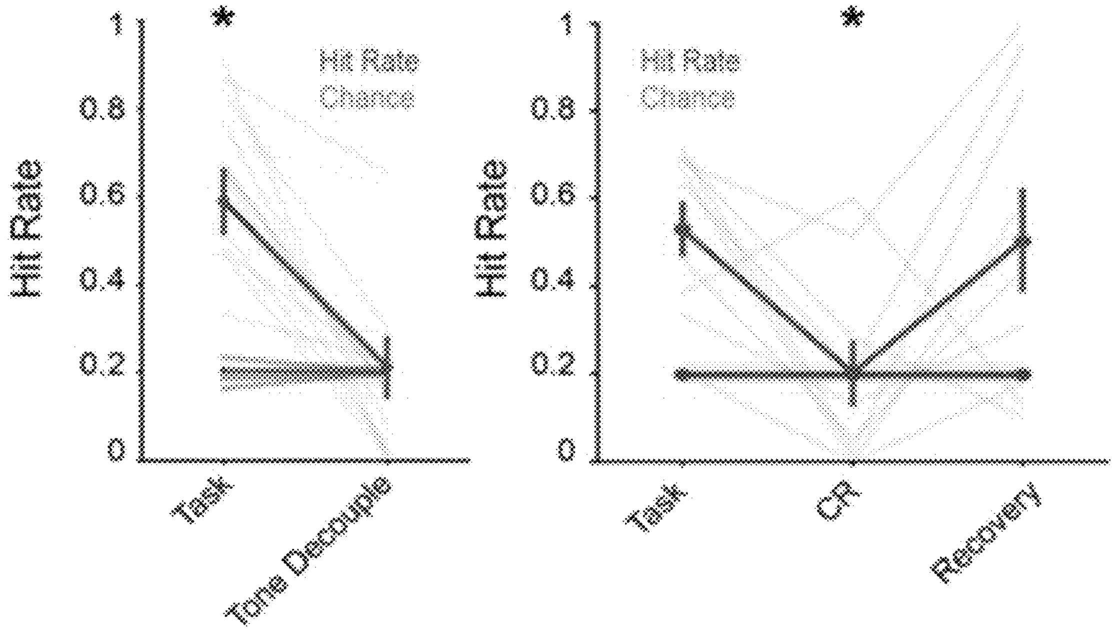
FIG. 2G is a graph showing hit rate (green) and chance (magenta) for training day 7 (left, 'Task') or a tone-decouple (right), where the auditory tone no longer contained information about the neural cursor. Thick lines indicate the mean±s.e.m. of n=11 mice (* indicates p<0.05, Wilcoxon signed-rank test).
FIG. 2H is a graph showing hit rate (green) and chance (magenta) for a contingency reversal experiment. Mice performed the task normally for 40 trials ('task'), then the reward contingency was reversed ('CR') such that the lowest, instead of highest possible cursor value triggered rewards. After 40 trials, the original task rules were restored ('recovery'). * indicates p<0.05, Kruskal-Wallis Test with Dunn's post-hoc test.
Figure 7F:
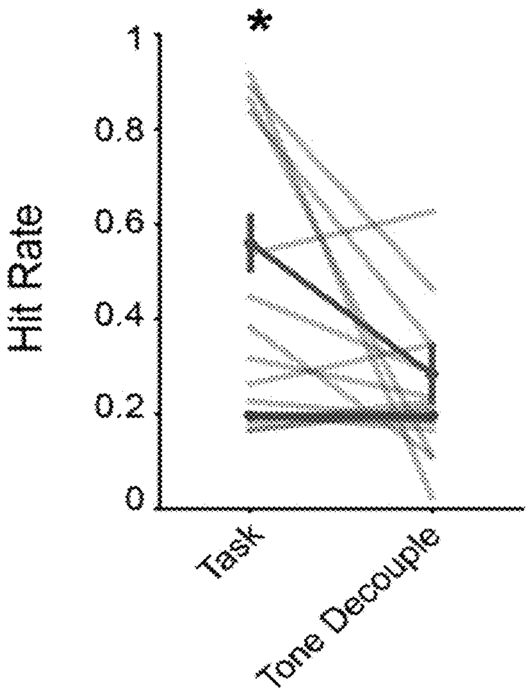
FIG. 7F is a graph showing hit rate (green) and chance (magenta) for training day 7 (left, 'Task') or a tone-decouple (right), where the auditory tone no longer contained information about the neural cursor. Thick lines indicate the mean±s.e.m. of n=9 mice (* indicates $p<0.05$, Wilcoxon signed-rank test).
Figure 8A:
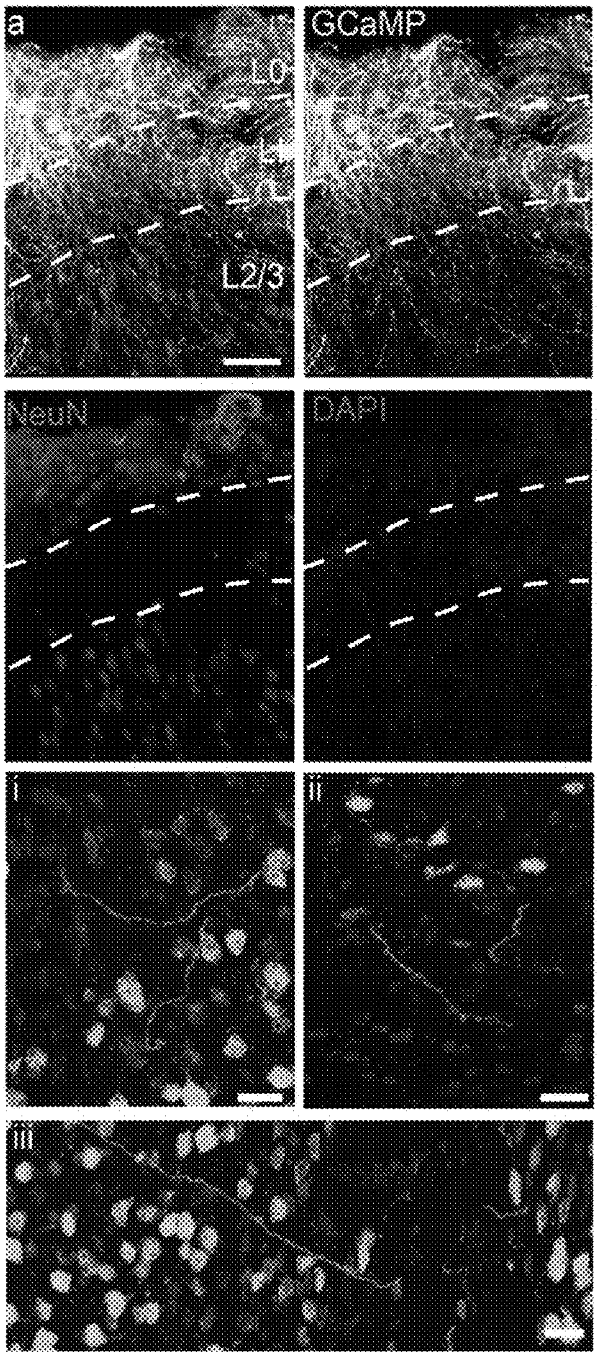
FIG. 8A is a representative confocal image of a mouse implanted with L0 neurons electroporated with GCaMP (yellow) and stained with NeuN (magenta) and DAPI (blue). Scale bar is 100 μm.
Figure 8B:
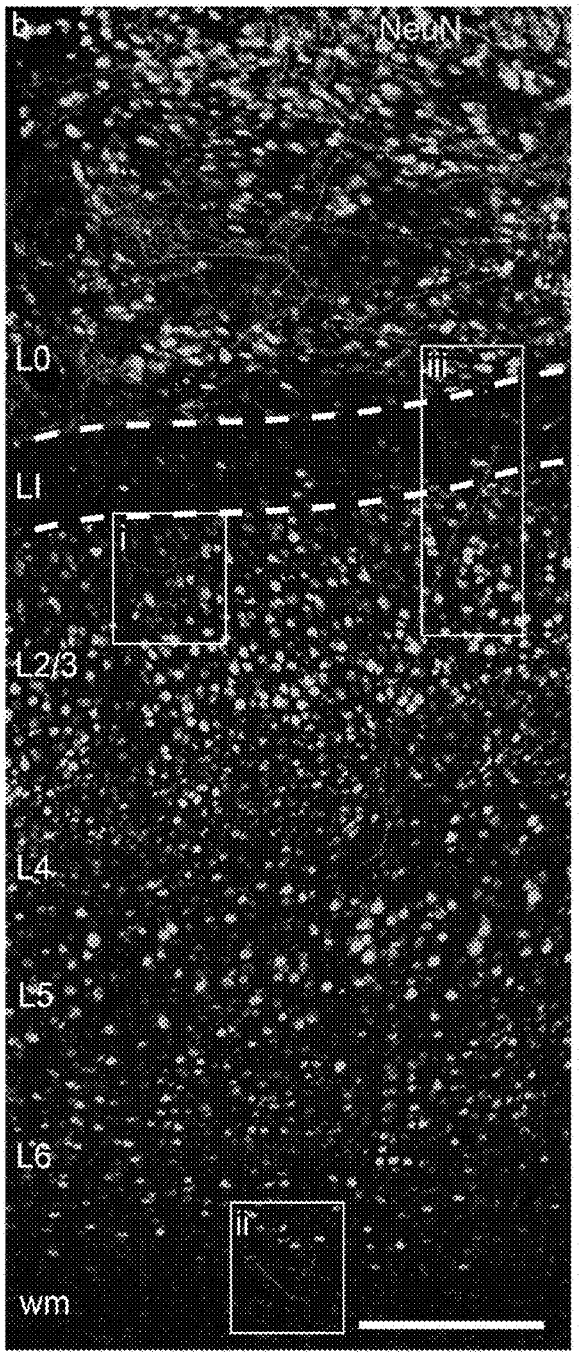
FIG. 8B is a representative confocal image of a mouse implanted with L0 neurons sparsely electroporated with mRuby3 (magenta, 1:50 typical labeling density) and stained with NeuN (yellow) and DAPI (blue). Scale bar is 100 μm. Insets i-iii show example axons extending horizontally (i), descending vertically from L0 (ii) or entering white matter (iii). Scale bars are 10 μm.
Figure 10A:
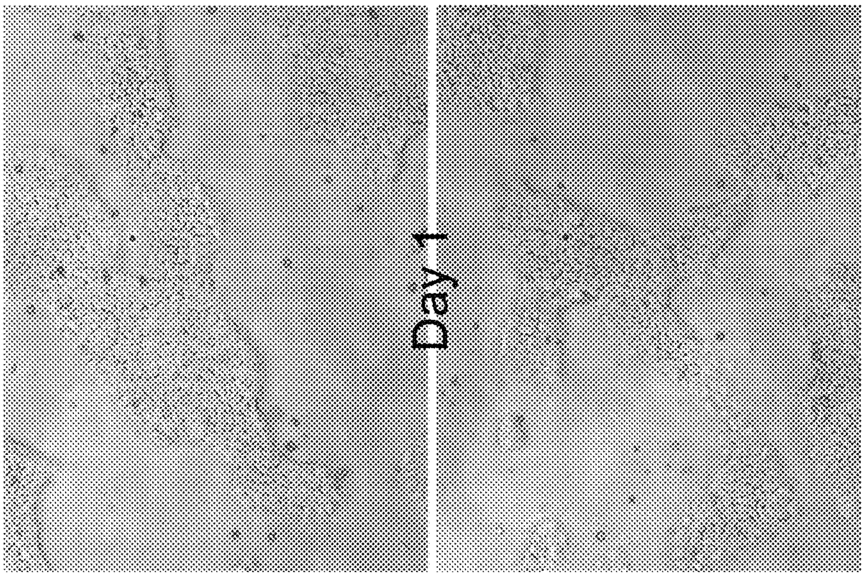
FIG. 10A-10G show stem cell to human neuron differentiation from Day 1 to Day 7.
Figure 10B:
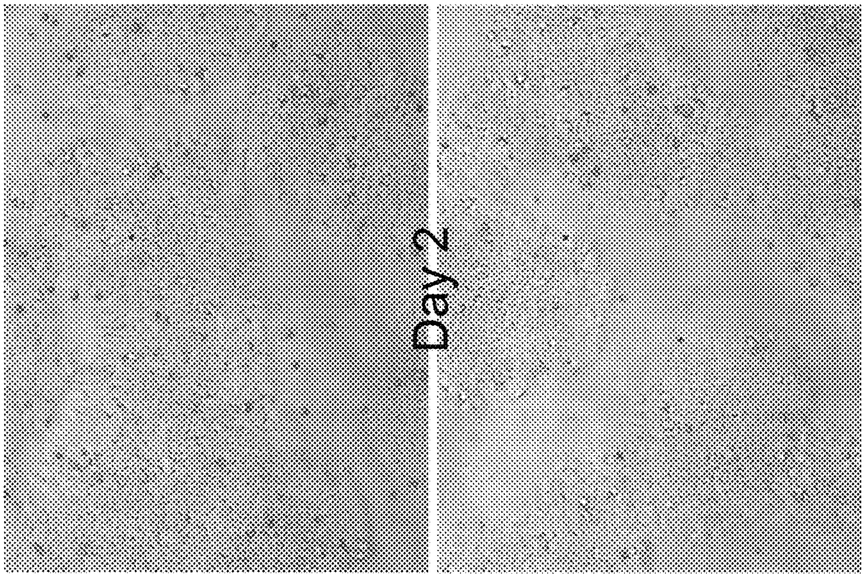
Figure 10C:
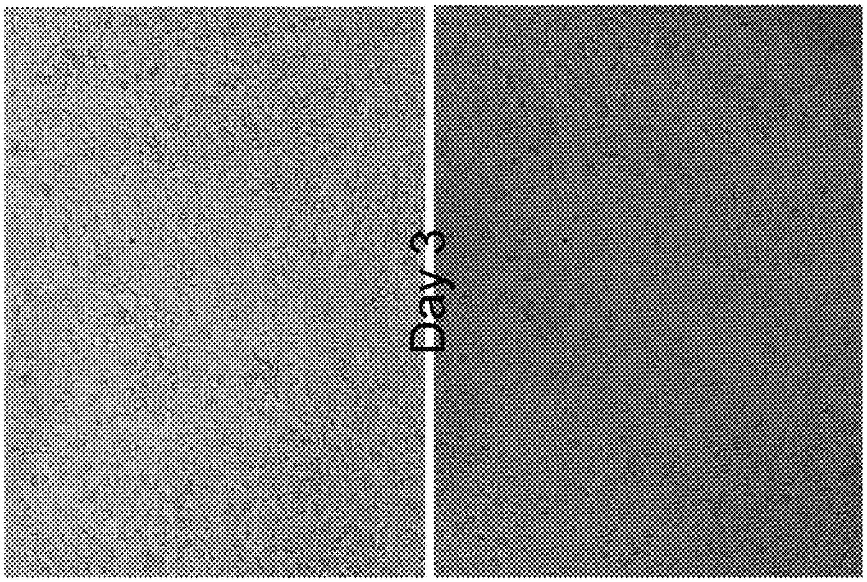
Figure 10D:
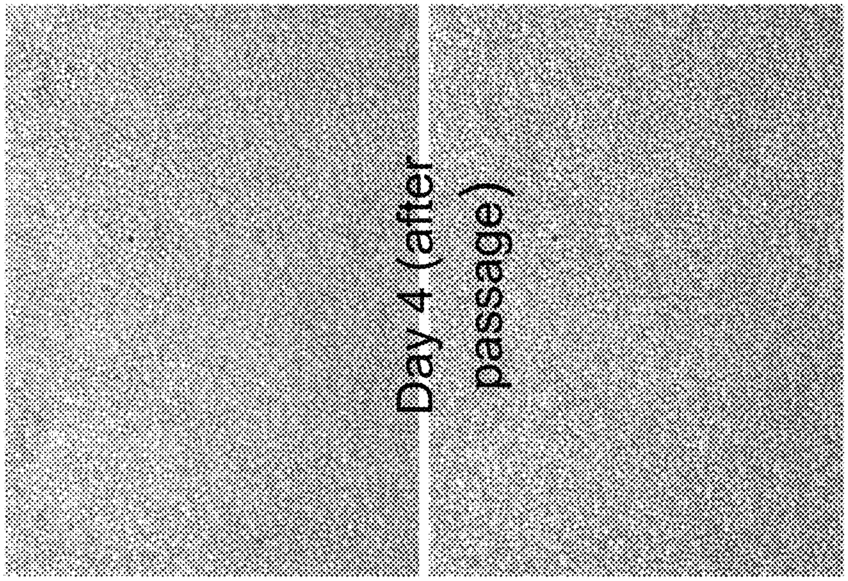
Figure 10E:
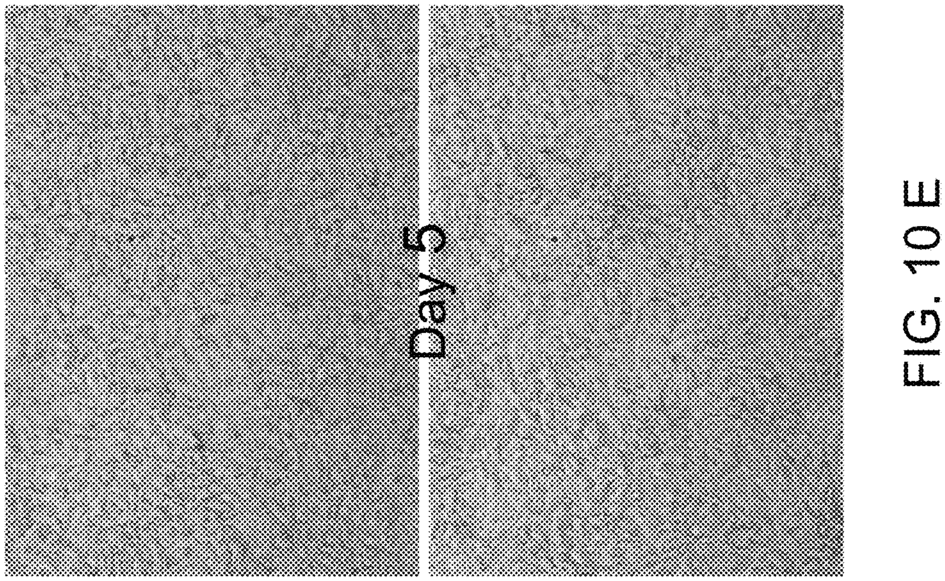
Figure 10F:
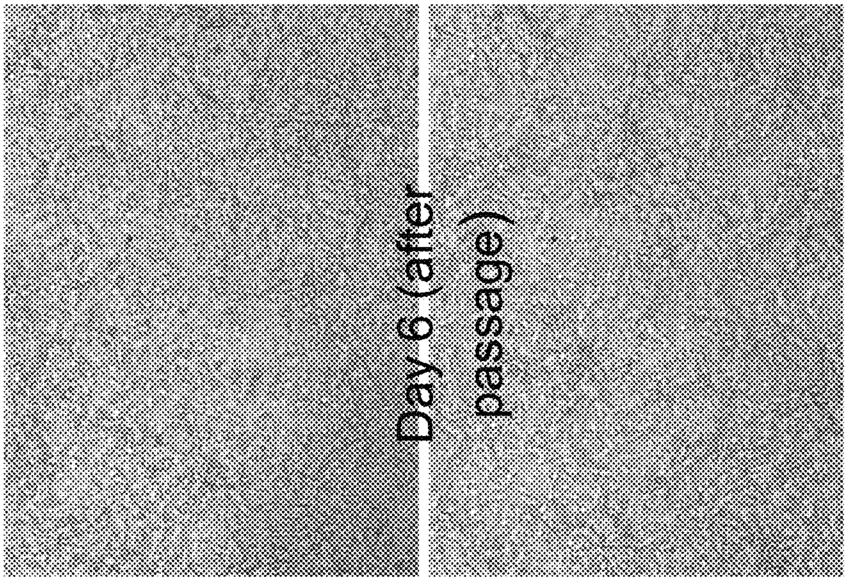
Figure 10G:
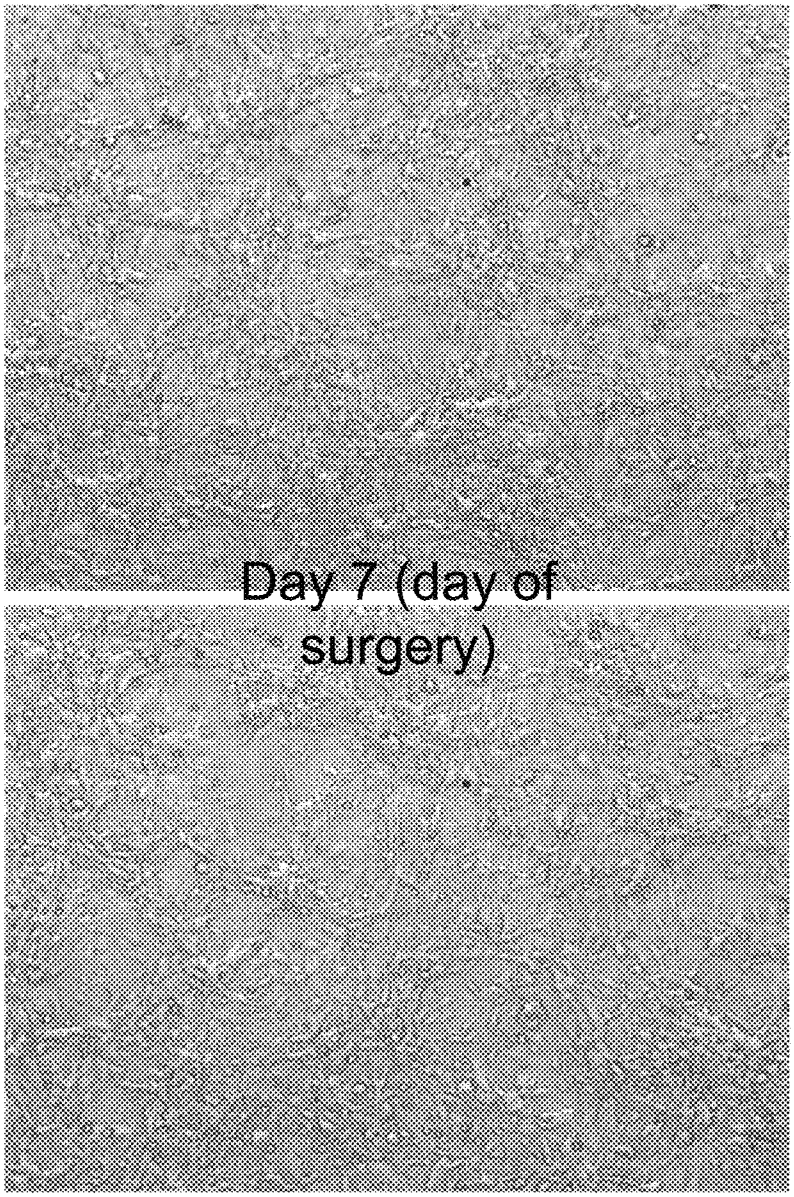

We performed two control experiments to ensure that the mice were using auditory feedback to solve the task. We first asked if the mere onset of auditory stimuli, which would also signal the availability of rewards to trained mice, could by itself trigger a brain-state change that altered neural activity such that the mouse gained a large number of rewards without really learning the mapping from neural activity to cursor. To test this, after the final training session, we performed an auditory decoupling experiment. Mice still controlled a neural cursor that would trigger a reward at a given threshold, but the tone was played back from a previous session, and therefore contained no information about the cursor's state. Under these conditions, mean population performance degraded to chance levels for both L0 and L2 mice (FIG. 2G, FIG. 7F, task: $p<0.002$, tone decoupling: $p=0.7$, Wilcoxon signed-rank, hit-rate versus chance). Many mice performed well below chance, perhaps giving up in frustration when the tone previously associated with reward delivery failed to yield water. Interestingly, two mice were able to achieve high levels of performance without auditory information. While we observed these sessions with an infrared camera, we could not associate any overt motor actions with performance in these or any other mice. Although we cannot rule out that mice solved this task by initiating a motor program, if they did, this would still represent a valid solution to the task, and would demonstrate that L0 neurons have access to motor signals.

We next tested if L0 neurons were sensitive to the contingency of the reward by transiently reversing reward contingency mid-session. We trained mice for 40 trials using the standard tone-mapping that they had previously learned to allow them to learn the brain-tone mapping, which we changed daily. After 40 trials, we reversed the mapping such that rewards were given at 'negative' threshold, requiring the mouse to modulate E2 over E1 instead of vice versa. This also required the mouse to associate the lowest, rather than the highest, tone with rewards. Task performance dropped precipitously for 40 trials when this change was implemented. We then restored the original mapping for another 40 trials and observed recovery of behavioral performance (FIG. 2H, $p=0.023$, Kruskal-Wallis with Dunn's post-hoc test). These data indicate that modulation of L0 neurons is sensitive to reward contingency. Together these results demonstrate that mice can volitionally control the activity of L0 neurons to perform a simple BCI task.

Example 5—Histological Analysis of BCI

Figure 3:
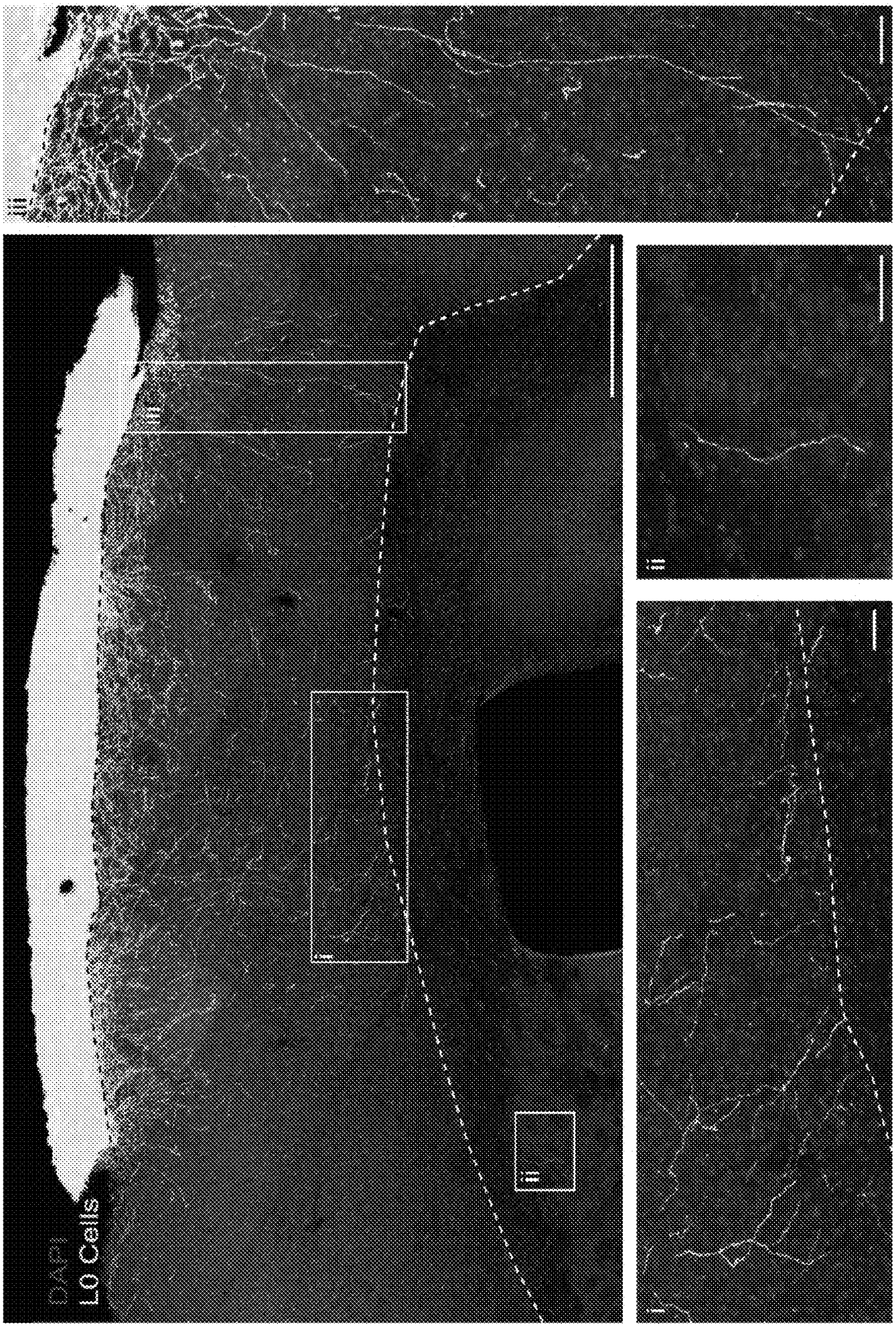
FIG. 3 is a representative confocal image from cortical section of a mouse implanted with cortical L0 and electroporated with pCAG-ChR2-tdTomato (yellow) and stained with DAPI (blue). L0-L1 border is marked by the dashed black line, and the L6-white matter border is marked by the dashed white line. Image is overexposed in L0 to reveal neurites integrating into the cortex. Scale bar is 500 μm, 50 μm for insets. Insets i) axons deep in L6 entering white matter. ii) L0 axon present in striatum. iii) axon descending directly down from L0 to white matter.

Next, we performed a histological evaluation of engrafted animals to assess how L0 connects with the brain. We found that L0 consists of neurons located in a 50-500 μm band of cells located above L1 (FIGS. 3 and 5A-5C, FIGS. 8A, 8B, and 9A-9C). To see where L0 neurons project, we imaged brain sections from perfused mice with confocal fluorescence microscopy or light microscopy. These images show that L0 neurons extend dense processes both laterally within L0 and downward across the L0-L1 border, into the brain (FIGS. 3 and 5A-5C, FIGS. 8A, 8B, and 9A-9C). Thicker process resembling dendrites extended from L0 into L1 and the top of L2 (FIGS. 4A-4C, FIGS. 8A and 8B), but axons originating from L0 were not restricted to the superficial layers of the cortex. Instead, axons infiltrated the entire cortical volume beneath the L0 graft (FIG. 3, FIGS. 8A, 8B, and 9A-9C). The density of processes decreased laterally away from the graft, and in some instances could be observed projecting to subcortical structures (FIG. 3).

Figures 4A, 4B, 4C:
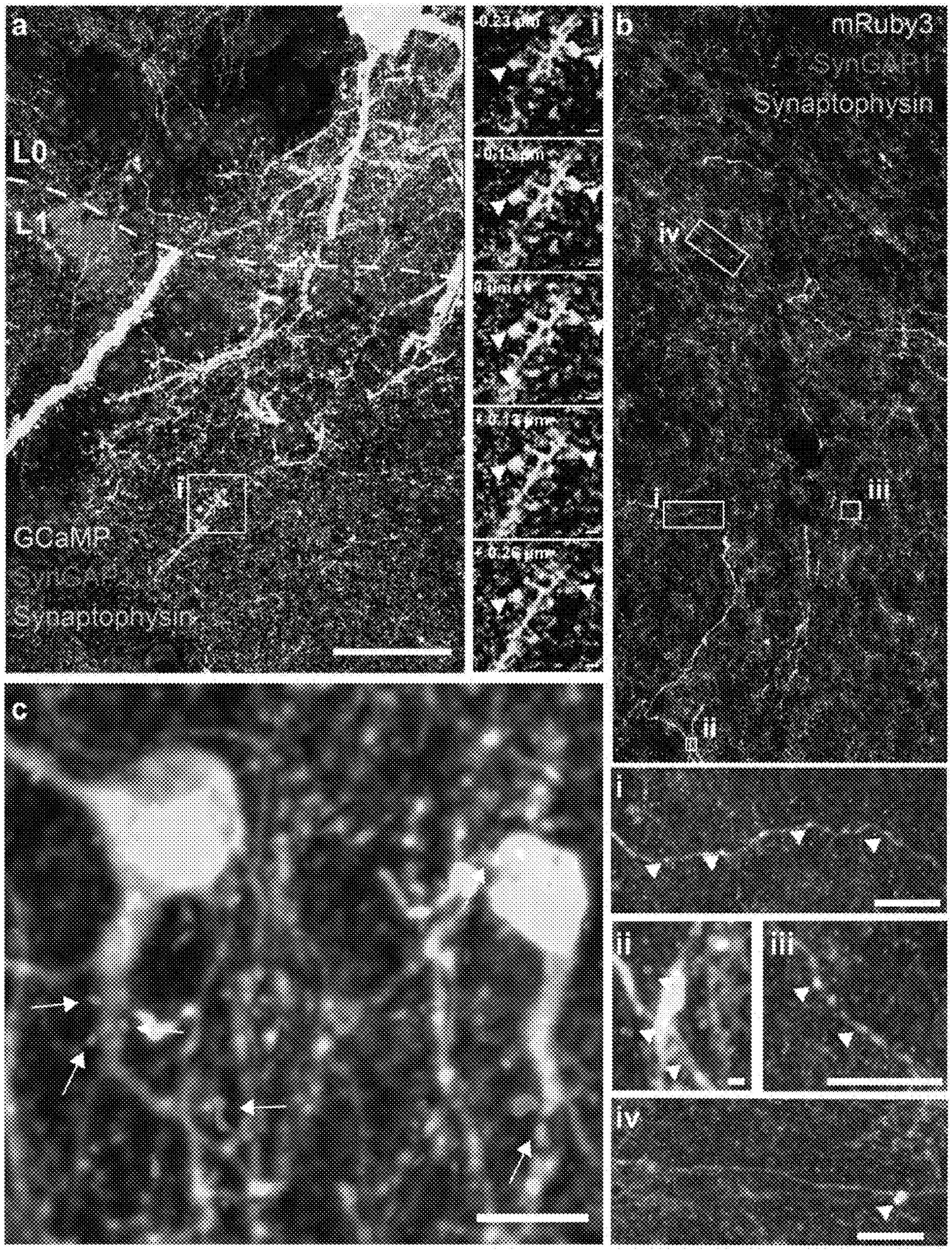
FIG. 4A is a representative confocal image from a cortical section of a mouse implanted with L0 neurons electroporated with GCaMP (yellow) and stained for pre- and post-synaptic markers (Synaptophysin: cyan, SynGAP1: magenta) showing spiny dendrites crossing from L0-L1 (Scale bar 20 μm). Dashed line indicates the L0-L1 border. Inset i shows serial sections of a z-stack through a section of spiny dendrites showing colocalization of the dendrite with synGAP1 (white) and closely opposed by synaptophysin. Scale Bar on the inset is 1 μm.
FIG. 4B is a representative confocal image from a cortical section of a mouse implanted with L0 sparsely electroporated with mRuby3 (1:50 normal cell concentration) and stained with synaptic markers as in (a). Scale bar is 100 μm. Insets i-iv: blow ups of examples of axons originating in L0 colocalizing with synaptophysin (white) and closely opposed to synGAP1 puncta. Scale bars in i, iii, iv are 10 μm and 1 μm in ii.
FIG. 4C is a representative confocal image from a cortical section of a mouse implanted with L0 neurons electroporated with GCaMP (yellow) stained with GAD65 (magenta) and DAPI (blue). Scale bar is 10 μm.

High resolution confocal imaging with sparsely labeled L0 neurons confirmed that dendrites originating in L0 and extending into L1 featured mature spines (FIGS. 4A-4C). Optical sectioning of tissue stained with synaptic markers showed that the postsynaptic marker SynGAP1 was present in spines from L0 dendrites, and was closely opposed to the presynaptic marker synaptophysin in L1, showing that the molecular machinery of excitatory synaptic input is present in the superficial layers (FIGS. 4A-4C). This suggests that the host brain forms excitatory chemical synapses with the graft, providing a possible mechanism for the graft's ability to modulate activity to perform a BCI task. Axons from L0 feature numerous putative boutons (FIGS. 3 and 4A-4C, FIGS. 8A, 8B, and 9A-9C), suggesting that L0 can release neurotransmitters onto host neurons. Indeed, staining with synaptic markers showed colocalization of synaptophysin with L0 axons deep in the cortex in close proximity to SynGAP1 puncta (FIGS. 4A-4C). Staining with GAD65 puncta indicated that L0 neurons receive apparent GABAergic input on their soma and proximal dendrites, although we could not determine if this input originates from the cortex or from inhibitory neurons present within the graft (FIGS.

4A-4C). Together, this data showed extensive integration between the graft and the cortex.

Example 6—Glial Response to BCI

Figures 5A, 5B, 5C:
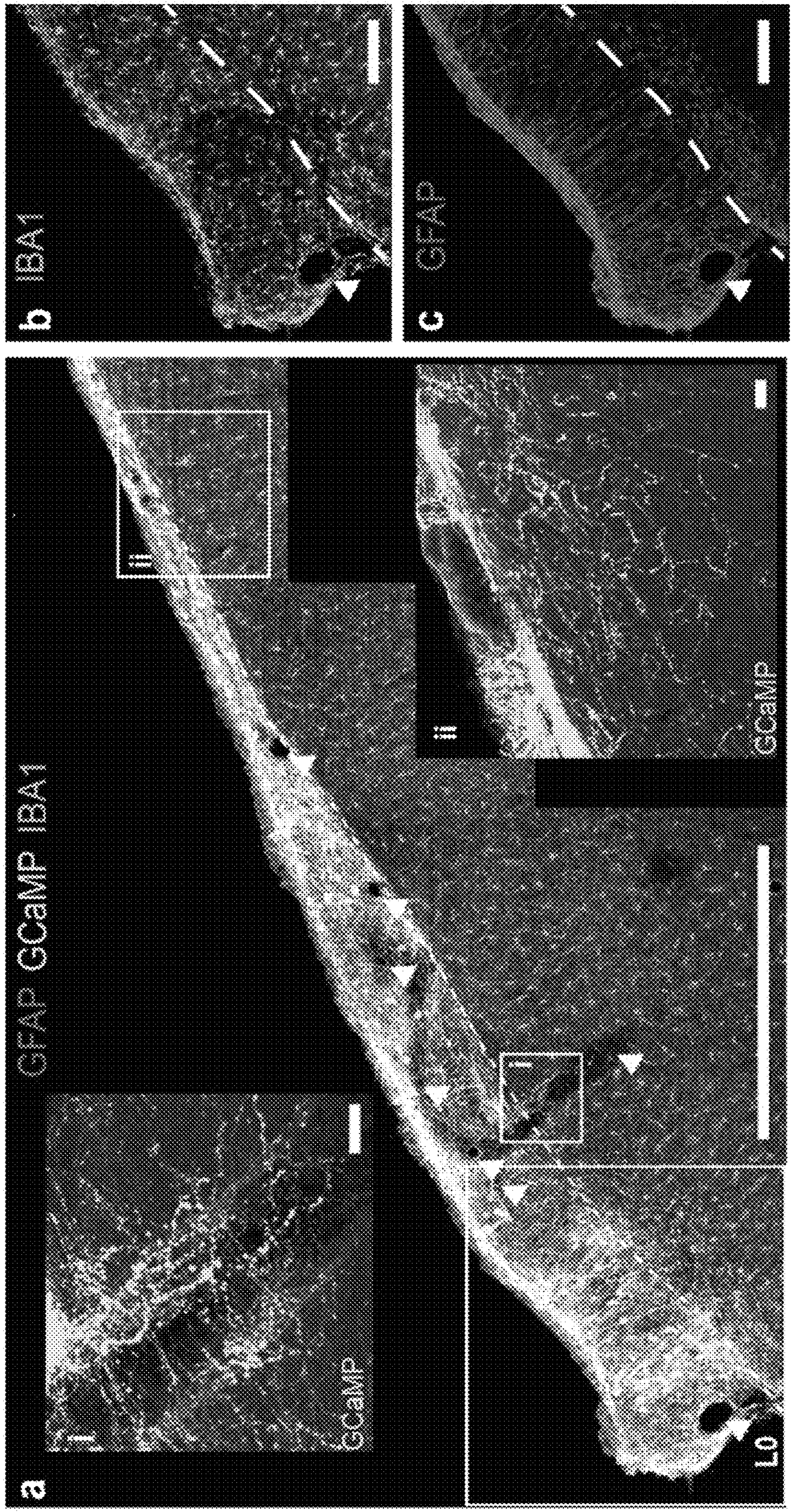
FIG. 5A shows tiled high resolution confocal images of a coronal brain section from a representative engrafted mouse. Yellow: antibody-enhanced GCaMP, Cyan: Iba1, Magenta: GFAP. Arrowheads indicate blood vessels that appear to be infiltrating L0. Scale bar is 500 μm. Insets i-ii) overexposed GCaMP to show robust L0 neurite infiltration into the cortex in the presence (i) or absence (ii) of blood vessel penetration. Scalebars are 20 μm.
FIG. 5B shows the Iba1 channel from inset iii in (a) showing non-phagocytic microglia tiling L0. Scale bar is 100 μm.
FIG. 5C shows the GFAP channel from inset iii in (a) showing vertically oriented astrocytes sealing L0 from the glass coverslip and supporting vascularization (arrowhead). Scale bar is 100 μm.

We next evaluated the glial response to the graft. Since the graft and host cells shared a uniform genetic background, we did not anticipate a generalized immune response. Staining for astrocytes and microglia with GFAP and Iba1, respectively, revealed that both were present throughout L0 (FIGS. 5A-5C). Glia did not exhibit 'activated' or phagocytotic morphologies on the L0-L1 border, or deeper in the brain. This indicates that implantation of L0 did not cause an immune rejection or extensive glial scarring (FIGS. 5A-5C). Although we observed both astrocytes and microglia in L0, we did not observe colocalization of these markers with electroporated graft cells (FIGS. 5A-5C), suggesting that these cells originated in the brain. The elevated GFAP expression and lack of 'activated' morphology suggests these cells may be in a proliferative state, as would be expected if they were infiltrating L0 to provide metabolic and structural support. Indeed GFAP positive cells were predominantly oriented parallel to the cortical surface, apparently creating a seal between the glass cranial window and the graft. Astrocytes in L0 also appeared to engulf blood vessels that appeared to vasculatrize L0 (FIGS. 5A-5C). This suggests that glia in the graft may be actively remodelling the tissue, but are not neurotoxic. Together, this data shows that grafting an artificial cortical layer above L1 can be achieved without a foreign body response or immune reaction and results in extensive infiltration of the brain by axons and dendrites that form and receive synaptic connections allowing bidirectional interfacing with the brain.

Example 7—Discussion

In this study, we demonstrated an approach to BCI using an artificial cortical L0 formed from transplanted neurons that functions as an interface between recording devices and the brain. We show that this layer survives, develops, and integrates with the brain. We used L0 for BCI by requiring the mouse to volitionally modulate L0 activity to obtain rewards. This implies that L0 is integrated with the brain to a degree sufficient for the animal to control, or at least modulate, it's activity patterns. Histology supports this idea, revealing that L0 extends spiny dendrites that possess synaptic markers into the superficial layers of the cortex. L1 is a hub of long-range and higher order inputs, potentially allowing L0 to tap into multimodal contextual information. Dense axonal arborizations from L0 in the cortex implies that ongoing L0 activity is monitored by the cortex, providing a mechanism whereby the brain could sense L0's activity state, although in our task this feedback was provided by auditory information. The dense axonal fibers from L0 imply that electrical or optogenetic stimulation of L0—potentially with single cell resolution—could be used to write information to the brain. By grafting neurons to form L0, recordings from the brain at single neuron resolution are obtained without genetic modification of the host organism and with no traumatic penetration of the brain's parenchyma. Instead, the brain is penetrated by naturally in-growing neurites, and bidirectional communication is achieved via chemical synapses, blurring the boundary between implant and host.

The fundamental challenge for any BCI is to collect signals distributed throughout the three dimensional volume of the brain and route it to silicon-based electronics, and conversely to route electronic input signals to appropriate sites in the brain. This must be accomplished with high resolution and low damage to the brain, two requirements which are fundamentally at odds. Functional imaging techniques break this relationship at the expense of viral infection of the brain and over-expression of fluorescent calcium reporters. L0 decouples the relationship between channel count and cell damage by using neurons to non-destructively integrate with the brain and project cortical signals onto a flat structure on top of the cortex that can be safely accessed. By using electroporation ex vivo, our approach leveraged modern activity sensors while avoiding modifying the host organism's genome and the use of viruses. This approach does not elicit a foreign body response; indeed, astrocytes and microglia from the brain appear to colonize the graft to provide support or surveillance. In contrast, injecting neurons or destructively penetrating the brain with a living graft or organoid forfeits many of the advantages of a cell-based probe. In this study, we recorded L0 activity using 2P calcium imaging because of the ease with which this method facilitated studying the growth, development, and integration of the graft. Because of the superficial location of the graft, clear signals could also be observed using 1-photon miniature head-mounted microscope (Sup Video 4), providing a path to translation of an optical interface that does not rely on expensive and cumbersome multiphoton optics. However, there is no requirement for future versions of this interface to be optical in nature: future iterations of a L0 implant could use electrical instead of optical recording by engineering the tissue-electronics interface in vitro before engraftment.

Using an engineered bioelectronic bridge layer between electronics and biology has the potential to address key challenges for implanted BCIs. Penetration of the brain by neurites avoids cell death, damage, disruption of vasculature and gliosis. Since neurons intrinsically share the material properties of the brain, the biological 'leads' are unaffected by micromotions and are in no danger of experiencing encapsulation failure, trace breakage, or leaching materials over time. By tethering transplanted neurons to electrode pads, future versions of a L0 interface could record high-amplitude spikes on all channels. This would substantially decrease the need for signal amplification, thereby decreasing the heat generated per channel, allowing implants with significantly increased channel count compared to existing fully implanted devices.

Biological electrodes could also allow optical or electrical stimulation that is more precise and multimodal than conventional ICMS. Since neurons are accessible at the top of the brain, they could be addressed for stimulation individually; this could be accomplished either by direct current stimulation using very low powers due to proximity between the living probe and electrode or via optogenetics using a microLED array. With stimulation featuring both single-cell resolution and functioning via chemical synapses, input from the implant could in theory be indistinguishable from input from host neurons. Furthermore, by engineering the neurotransmitter phenotype of engrafted cells, stimulation of L0 could potentially manifest as inhibition or neuromodulation instead of just excitation. This could open the door to novel applications of stimulation from a living graft.

Example 8—Methods

Cell Engraftment

Pregnant C57/Bl6 mice were $CO_2$ euthanized at approximately day 15 of embryonic development (E14-17). The embryos were removed from the uterus and placed in Hank's Balanced Salt Solution (HBSS) and transferred to a laminar flow hood on ice. Embryos were removed from the uterus and placed in ice-cold dissection medium (DM) (HBSS+10 mM $MgCl_2$*6 $H_2O$, 10 mM HEPES, 1.5 mM kynurenic acid, pH 7.2). The embryos were decapitated, the brains isolated, and the meninges removed from the cortex using sharp forceps under sterile conditions. Cortices were separated from the hippocampal formation and midbrain and stored in ice-cold DM until the dissection of all embryos was complete.

Isolated cortices were placed in a 1.5 mL tube and allowed to sediment. The supernatant was removed and 1-2 mL of pre-warmed Papain-solution (1:50 Papain, Sigma 76216 and 2.5 mM L-Cysteine in DM). The cortices were placed in a standard cell culture incubator for 6-15 minutes. After the tissue began to clump together, the tube was returned to the flow-hood. The Papain was carefully removed so as not to disturb the tissue, and the clumped tissue was washed three times with 1 mL of warm Light Trypsin Inhibitor (1 mg/mL Trypsin inhibitor Sigma T9003 and 1 mg/mL Bovine Serum Albumin, Sigma 05470 in DM), followed by three washes with 1 mL of Heavy Inhibitor (10 mg/mL Trypsin inhibitor Sigma T9003 and 10 mg/mL Bovine Serum Albumin, Sigma 05470 in DM). The tissue is then washed once with 1 mL of sterile PBS, and then removed. 0.5-1 mL of Resuspension Buffer R (Invitrogen™ Neon™ Transfection System, Thermo Fisher Scientific MPK10096) was then added to the preparation at room temperature, and the tissue was triturated 20-30 times to form a single-cell suspension. The concentration of this cell suspension was determined using a BioRad TC20 automated cell counter. The cell suspension was diluted to 1×107 cells/mL in Resuspension Buffer R.

To electroporate the cell suspension, 3 mL of Electrolytic buffer "E" was added to the electroporation chamber containing the cell suspension. Plasmid DNA (pCAG-H2B-mRuby3-P2A-GCaMP7s, pCAG-ChRimson-tdTomato, pCAG-ChR2-tdTomato, or pCAG-mRuby3) was added to cell suspension at a final concentration of 0.01 μg/μL. Cells were electroporated using the Invitrogen Neon Transfection System. Using the electroporation syringe and tips provided by the manufacturer, 100 μL of cell suspension at a time was electroporated using the following conditions: 1500 V, 20 ms, 1 pulse. The cells were then pelleted (400 RCF, 5 min, 6 °C) using a microcentrifuge and the supernatant was discarded. A mixture of L-15 (L-15 Medium, Sigma L5520) with 10% DNase I (RNase-free, New England BioLabs Inc. M0303L) was then added to the electroporated cells and the pellet of cells was gently resuspended with a pipette to a concentration of 300K cells per microliter. The cells were then kept on ice until transplantation (0-3 hours).

While cells were being electroporated, wild-type adult C57/Bl6 mice (Jackson Labs or Charles River Laboratory) were anesthetized under isoflurane on a heated pad, head fixed in a stereotactic apparatus (Kopf), and administered buprenorphine (0.05 mg/kg) and dexamethasone (2 mg/kg). Hair was removed and the surgical site was sterilized. The scalp was removed, the fascia retracted, and the skull lightly etched. The skull was cleaned and sealed with a thin layer of vetbond (3M) and a 3 mm circular craniotomy was drilled over the primary somatosensory cortex using a dental drill, and the dura was removed. Bleeding was stopped using gelfoam (Pfizer) and room-temperature sterile artificial cerebrospinal fluid (aCSF). A thin well was created around the craniotomy using UV-cure acrylic (Flow-It Accelerated Light Cure, Pentron N11WA). 10 μL of the ice-cold cell suspension was applied to the craniotomy while the mouse was maintained under anesthesia. The cells were allowed to settle on the cortical surface while the supernatant evaporated (~15-30 minutes per application, 2-4 applications of 10 μL). At least 10 minutes after the final cell application, the craniotomy was washed with sterile aCSF, and the craniotomy covered with a sterile glass plug, a 5 mm coverslip adhered to two 3 mm coverslips (Small Diameter Coverslips #1 thickness, Harvard Apparatus 1217H19/1217N66) with optical adhesive (Norland 71). The glass coverslip was secured to the well using metabond (C&B Metabond® Quick Adhesive Cement System, Parkell S380). The rest of the exposed skull was then covered by metabond, and a metal headbar was adhered to the skull. The animal was allowed to recover in a heated recovery cage before returning to their home cage.

For animals engrafted over primary motor cortex for use with a miniscope, this approach was slightly altered. For these surgeries, the entire skull, except for the region to be drilled away, was covered with a thin layer metabond before drilling. The craniotomy was exposed, and the height differential between the brain and the metabond was sufficient to form a well that could hold 2-5 μL of the cell suspension. A single glass coverslip covered the craniotomy and was sealed with additional metabond, and no headbar was attached. A UCLA V4 miniscope baseplate was attached to the cranial window using dental acrylic under anesthesia more than a week after engraftment.

Stereotactic Injection

Wild-type C57/Bl6 mice were anesthetized under isoflurane on a heated pad, head fixed in a stereotactic apparatus (Kopf), and administered buprenorphine (0.05 mg/kg) and dexamethasone (2 mg/kg). After sterilizing the incision site, the skin was opened, and a small burr hole was drilled over S1 using a 0.24 mm drill bit (Busch) (3.5 mm lateral, 1.4 mm posterior to bregma). The glass micropipette was lowered into the burr hole, and we waited five minutes before beginning the injection. 300-400 nL of AAV9 pSYN-GCaMP6s (Vigene) virus was injected using a micro syringe pump (Micro4) and a wiretrol II glass pipette (Drummond) at a rate of 25-50 nL/second at a depth of 150-300 μm below the pia surface. After the injection was complete, we waited five minutes before retracting the needle and closing the scalp using sutures. Mice were used 2-6 weeks post injection.

Cranial Window and Headbar

Mice that were previously injected with virus (1-3 weeks post injection) were anesthetized under isoflurane and administered buprenorphine (0.05 mg/kg) and dexamethasone (2 mg/kg). Hair was removed and the surgical site was sterilized. The scalp was removed, the fascia retracted, and the skull lightly etched. The skull was cleaned and sealed with a thin layer of vetbond (3M) and a 3 mm circular craniotomy was drilled over primary somatosensory cortex using a dental drill, and any bleeding was stopped using gelfoam (Pfizer) and sterile artificial cerebrospinal fluid (aCSF). The craniotomy was covered with a sterile glass plug, a 5 mm coverslip adhered to two 3 mm coverslips with optical adhesive (Norland 71). The glass coverslip was secured to the well using metabond. The rest of the exposed skull was then covered by metabond, and a metal headbar was adhered to the skull. The animal was allowed to recover in a heated recovery cage before returning to their home cage.

Two-Photon Imaging

For calcium imaging, mice were head-fixed on a freely spinning running wheel under a Nikon water immersion objective (16×, 0.8 NA Nikon) and imaged with a Sutter moveable objective (MOM) two-photon resonant scanning microscope within a darkened box. The imaging laser source was a Mai Tai Ti: Sapphire laser (Spectra-Physics) mode locked at 920 nm for calcium imaging or at 1000 nm for structural imaging. Signal was collected with a Hamamatsu photomultiplier tube (H10770PA-40). The imaging system was controlled by Scanimage 2018 (Vidrio) running on Matlab (v2019b, Mathworks). Functional images were acquired at 920 nm with ~50 mW average power. For developmental structural analysis, volumes were acquired at 1250×1250 μm field of view covering 300 μm in Z with 2 μm steps. For imaging of spontaneous L0 events, a single 1250×1250 μm field of view was imaged at 30 Hz. For online BMI, a single plane 430×430 μm was imaged at 30 Hz with online 3D motion correction enabled (Scanimage 2018, vidrio). For neuronal morphology, images were acquired from a 215×215 μm FOV.

Analysis of Graft Development

For analysis of graft thickness, z-stacks were acquired from a 1250×1250 μm field of view with 300 μm thickness and 2 μm spacing (920 nm). Cell nuclei (H2B-mRuby3) were segmented using Cellpose and nuclei assigned to a given z-level based on the location of their centroids. The thickness of L0 was calculated by identifying the range in z that contained 90% of the segmented cell nuclei.

To characterize spontaneous activity during graft development, 5-10 minutes of spontaneous activity was recorded (1250×1250 μm FOV, 30 Hz, 920 nm, 50 mW average power). Calcium imaging analysis packages typically identify calcium sources by finding spatially isolated groups of locally co-varying pixels. However, the massive population events we observed early in graft development (Sup Movie 1) and the numerous silent neurons we observed later in development were significantly different from the typical use case of these packages, and produced poor results in our hands. Instead, we used Suite2P's registration function to motion correct movies using the red nuclear signal as a reference, and then used Cellpose to segment nuclei, choosing a model that dilated the nuclear mask to capture surrounding cytoplasm, only several pixels on the low zoom were used. We did not correct for neuropil contamination, since the sparse labelling of L0 achieved using electroporation resulted in clear separation between neurons. This strategy allowed us to sample all transfected L0 cells, regardless of whether they exhibited any spontaneous activity.

We extracted average fluorescence for each mask and for the full frame. dF/F was calculated using Fo=30th percentile of the recorded fluorescence values. To identify population events, we convolved the full-field dF/F signal with a linear function to identify event rise times. Population events were defined as frames where the signal was 3.5 standard deviations above baseline signal. Neurons were considered to participate in a given population event if their convolved dF/F signal was above threshold during frames assigned to population events. Pairwise correlation was calculated using the dF/F signal from the full duration of the recording. For comparison of L0 and L2 spontaneous pairwise correlation, the L2 correlations were computed using online data from the baseline period of the first day of BMI training, before the animals had been exposed to the task.

For analysis of dendritic complexity, sparse labeling was achieved by mixing a population of cells electroporated with pCAG-mRuby3 1:50 with a population of non-electroporated cells, thereby maintaining the density of cells in the graft while reducing the number of labelled cells. Z-stacks of 300 μm with 2 μm steps were obtained at several timepoints after development. Sholl analysis was performed on traced dendritic arbors from maximal intensity projections using ImageJ and depth-coded Z-stacks were obtained using the Z-stack Depth Color Code package for ImageJ.

Optical Brain-Computer Interface Task

Mice were placed on a high-fat diet (PicoLab Mouse Diet 21) 5-7 days before water restriction. Upon beginning water restriction, mice were fed water from a syringe for two days, and for the next two days they received their water for free in the 2P experimental rig. Mice performed the BCI task for 8 sessions, and then performed two control experiments, contingency reversal and tone decoupling, described below.

The BCI task required the mouse to volitionally modulate the calcium dynamics of target neurons to achieve a reward, and was conducted largely as described. To perform BMI experiments, mice were placed on the experimental apparatus, and an imaging field was chosen with bright, active neurons. We did not attempt to find the same region or same neurons from day to day. To select ensembles, we imaged a 430 by 430 μm field of view for several seconds, and calcium sources were segmented using custom Matlab software using the GCaMP6s signal from control mice or the H2B-mRuby3 (nuclear) signal from engrafted mice. We used laser power ~50 mW, and depths of 144±37 μm for control mice and 136±26 μm for engrafted mice (these depths are relative to the first observed signal, and do not necessarily correspond to cortical depth). We then acquired a reference z-stack to allow online 3D motion correction to compensate for any slow drift over the course of the experiment (Scanimage, Vidrio). To establish baseline activity, we imaged the field of view for 10-20 minutes while tracking the activity of all segmented cells. During this period the experimenter selected appropriate calcium sources for BCI. Appropriate calcium sources met the following criteria: 1) they were not over-filled cells, which might indicate poor cell health, 2) they were well-isolated from other nearby neurons, ensuring that the signal was not contaminated by a nearby cell, 3) they exhibited well-defined spontaneous calcium transients and did not exhibit plateau, or step-function behavior, 4) their signals were unaffected by small motions associated with movement, and 5) they had a sufficiently bright baseline intensity so that photobleaching would not be a concern. The raw fluorescent values from calcium sources were calculated on-line and were smoothed over 200 ms (rolling average of 6 frames at 30 Hz). No auditory stimuli was played during the baseline period.

At the end of the baseline period, we selected four neurons to compose the output population. The output of the BCI task was a cursor value that was defined as the difference between the average z-scored fluorescence values of the activation ensemble (E1) minus the average z-scored fluorescence values of the control ensemble (E2).

$$\mathrm{Cursor}(t)=\Sigma F_{e1}(t)/n_{e1}-\Sigma F_{e2}(t)/n_{e2}$$

To select neurons to compose these ensembles, at the conclusion of the baseline period, we randomly assigned valid neurons to these populations, and put the neural activity recorded during the baseline period through a virtual behavior session using the trial structure defined below. We chose thresholds for the cursor value that would have resulted in a hit-rate between 15-25% during the baseline period. During the task, the cursor value was computed on-line from neural activity using Scanimage's integration function, and auditory feedback indicating the cursor value was delivered to the mouse with an ultrasonic speaker (Tucker-Davis Technologies, EC1). The online cursor value was linearly mapped to auditory feedback so that 24 kHz indicated the threshold cursor value to trigger a reward, whereas 1 kHz indicated 'negative' threshold. To measure the performance of mice on this task, we imposed a trial structure as follows. Trial start was indicated by beginning auditory playback of the neural cursor. Trials were 30 seconds long; failure to move neural activity past the target threshold constituted a 'miss' trial, and movement of the neural cursor past the threshold in less than 30 seconds after trial start defined a 'hit' trial. After a 'miss' trial, auditory feedback stopped for several seconds during a variable inter-trial interval, and the start of the next trial was cued by resumption of auditory feedback. For a 'hit' trial, moving neural activity to the target zone triggered the immediate delivery of a water reward. In order to conclude a 'hit' trial, we required the neural cursor to return to below the middle of the cursor range. This ensured that mice could not solve this task by entering a state where activity was constantly maintained above threshold; instead, they had to actively modulate the neural cursor from rewarded value back to a neutral value to start another trial. After successfully moving the cursor from a rewarded to a neutral value after a hit trial, auditory feedback stopped during a randomized inter-trial-interval before the next trial began. Training sessions lasted 108±28 minutes for engrafted mice and 109±28 minutes for controls (engrafted: 86±15 trials, controls 97±21 trials).

After mice performed 8 BCI sessions, we performed two control experiments. The first, contingency-reversal (CR), mice performed a standard BCI session for the first 40 trials. We then altered how the cursor was computed on-line so that the cursor was given by E2−E1 instead of E1−E2. All else remained constant, so that the effect was that the mapping of neural activity to gain a reward was reversed. After 40 more trials we restored the map to the original values that the mouse learned in-session, and allowed the mouse to perform 40 more trials.

On a separate day we tested whether the simple presence of auditory stimuli itself was sufficient to modulate neural activity in a manner consistent with solving this task. We therefore set up a normal BCI experiment, but instead of playing auditory feedback that reflected the value of the neural cursor, we replayed the cursor values from a previous experiment. In this way the animal still had the ability to get water rewards by modulating neural activity, but the feedback was unrelated to current brain state.

Histology

Tissue Processing

Mice were deeply anesthetized and transcardially perfused with heparinized saline (25 ku/mL) followed by 10% Neutral Buffered Formalin (NBF, VWR); brains were extracted and postfixed in NBF for 24 hours, then placed in 30% sucrose for 24-48 hr at 4 °C, frozen and sectioned using a Leica CM2050S Cryostat into 50 μm thick coronal sections. Sections were collected into 48-well dishes filled with a cryoprotective solution (30% glycerol, 30% ethylene glycol and 40% PBS) and kept at −20 °C.

Free-floating sections were rinsed 3× in PBS and incubated in a blocking solution containing 10% Normal Donkey Serum (NDS, Sigma, D9663), 0.3% TritonX-100 (Sigma, T8787), 0.1M glycine (Sigma, 410225) and a drop of IT-FX Signal Enhancer (Invitrogen, 136933) for 1 hr at room temperature. Then, sections were incubated in a mixture of primary antibodies (Table) diluted in PBS containing 1% NDS for 24-48 hours on a rocker platform at 4° C. Sections were then washed 3× in PBS containing 0.05% TritonX-100 (PBS-T), followed by incubation with fluorophore-conjugated secondary antibodies (Table 2) in PBS with 1% NDS 1-2 hours at room temperature, and if applicable, sections were counterstained with DAPI. Finally, sections were washed 3× with PBS-T, then rinsed in PBS and mounted on microscope slides using ProLong™ Gold antifade mounting media (Invitrogen).

Alternatively, sections were processed for GFP immunoperoxidase in which sections were first pretreated with 3% hydrogen peroxide to inactivate endogenous peroxidase, rinsed in PBS and then processed as described above. Following incubation with anti-GFP primary antibody, sections were rinsed in PBS and incubated in biotinylated secondary antibodies (Jackson Immunoresearch, 711-065-152) diluted in PBS-T. Sections were then incubated in ExtrAvidin (1:2,000, Sigma) and followed by Diaminobenzidine DAB (Sigma) enzymatic detection. Sections were rinsed in PBS, mounted on gelatinated slides, air dried and coverslipped with Neo-Mount mounting media (Sigma, 109016) counterstained with 0.1% Cresyl Violet (Sigma C5042-10G OR FD NeuroTechnologies, PS102-2).

Imaging

Fluorescent images were obtained using the ZEISS LSM 900/980 confocal microscope with the Airyscan 2.0 detector, utilising 5×/0.25 air, 10×/0.45 air, 20×/0.8 air, and 63×/1.4 oil immersion objectives (Carl Zeiss Microscopy, Jena, Germany). Fluorophores were excited using laser lines 405, 488, 561 and 639 nm, with corresponding emission band-pass filters of 420-480 nm, 495-550 nm, 573-615 nm and 607-750 nm. Widefield images were collected on an Axiocam 705. Large scale images (10× or 20×) were taken using z-stacks together with a tilescan overlap of 10%, with pixel size of 0.487 μm (x)×0.487 μm (y)×2 μm (z). Super resolution images (63×) were taken using z-stacks and/or tilescans with 0-10% overlap with pixel sizes of 35 nm (x)×35 nm (y)×0.13-0.5 μm (z). Airyscan processing was done in ZEN Blue 3.3 software using the auto-filter setting with standard strength. Stitching of tilescans and max intensity projection processing of z-stacks was done in ZEN Blue.

TABLE 1

| Target | Species | Dilution | Product Number |
|---|---|---|---|
| GFP | Ch | 1:1000 | Invitrogen, A10262 |
| GFP | Rb | 1:10,000 | Abcam, ab290 |
| SynGAP1 | Rb | 1:1000 | Abcam, 77235 |
| Synaptophysin | Mo | 1:1000 | CST, 7H12 |
| NeuN | Rb | 1:1000 | Abcam, 177487 |
| IBA1 | Gt | 1:1000 | Abcam, 5076 |
| GFAP | Ch | 1:2000 | Abcam, 4674 |
| GAD65 | Mo | 1:500 | Synaptic Systems, 198111 |

TABLE 2

| Target | Fluorophore | Dilution | Product Number |
|---|---|---|---|
| Donkey anti Ch | 488 | 1:1000 | Biotium, 20166 |
| Donkey anti Ch | 633 | 1:500 | Biotium, 20168 |
| Donkey anti Rb | 488 | 1:500-1000 | Invitrogen, A21206 |
| Donkey anti Rb | 555 | 1:500-1000 | Abcam, 150062 |
| Donkey anti Gt | 555 | 1:500 | Abcam, 150130 |
| Donkey anti Gt | 405 | 1:500 | Abcam, 175664 |
| Donkey anti Gt | 488 | 1:500 | Abcam, 150129 |
| Donkey anti Mo | 647 | 1:500 | Abcam, 150107 |
| Donkey anti Rb | Biotin | 1:1000 | Jackson Labs, 711-065-152 |

Stimulation

The BCI experiment showed that L0 can be used to read out information from the brain. We next asked if stimulating L0 can input information into the brain. To test this, we leveraged an optical microstimulation task wherein mice are trained to report optogenetic activation of a population of neurons. In this task, mice with a cranial window and a ferrule for an optical fiber are placed into a custom behavior box with three ports. Trials are initiated by a nose-poke to the middle port, which triggers a masking LED located in the middle port on every trial. Mice then have 10 seconds to select left or right by poking their nose in the respective port. On some trials, optogenetic stimulation is provided via a fiber-coupled LED (470 nm, 10× pulses at 20 Hz). On trials where stimulation is provided, animals are rewarded for a left selection, and they are rewarded on the right port on trials with no stimulation. There is no punishment for an incorrect selection.

We first validated this task by training positive control mice injected in S1 with AAV-CAG-ChR2-tdTomato and negative control mice with no opsins. We trained mice for three weeks or until they exceeded criterion (D'=1). Since these mice were implanted with optic fiber ferrules, we could not screen them for expression before behavior, so after their behavioral experiments were completed we perfused, sectioned, and imaged their brains. Images were blinded and scored for expression, and mice were marked for inclusion in the dataset based solely on their expression levels, without reference to their behavior. Positive control mice all learned the task in 10.83±6.1 days (n=6). Negative control mice failed to learn the task after three weeks of training (0 of 5 mice met criteria after 3 weeks). We then trained mice engrafted with layer zero neurons electroporated with pCAG-ChR2-tdTomato three to five weeks after engraftment. Similarly to the positive controls, we screened the mice post-hoc blind to behavioral performance and included mice that had a healthy L0 graft without knowledge of behavioral outcome. Mice implanted with L0 were able to hit criterion 21±4 days (n=3 of 7 total) after beginning training. Given that 4 of the implanted mice did not hit criterion in time, we believe this outcome is due to the diminished transfection efficiency of electroporation of our transplanted cells. Stimulation may require a greater transfection efficiency of transplanted L0 cells in order to input salient information more reliably. Nevertheless, this data shows that stimulation of L0 can be used to transmit information to host brains on which it is engrafted, demonstrating that layer zero can be used as a bidirectional interface layer with the brain.

Optical Microstimulation Detection Task

Mice that had been engrafted with electroporated L0 neurons expressing pCAG-ChR2-tdTomato for 3-5 weeks were enrolled in behavior. Positive control mice expressing viral AAV9-CAG2-hChR2(H134R)-TdTomato (Vector BioLabs VB2896) and negative controls that underwent craniotomies, durotomies, and windowing (no viral injection) were entered into the task 3-5 weeks post-surgery. Mice were placed on a high-fat diet (PicoLab Mouse Diet 21) 5-7 days before water restriction. Upon beginning water restriction, mice were fed water from a syringe for two days, after which they began the first stage of training for the stimulation task which included habituation to the operant box.

The operant box featured three nose-poke ports each with an IR beam sensor. The center port contained a masking LED (470 nm), and the left and right ports contained lick spouts. A hole in the top of the box allowed entry of a rotary joint patch cable with 400 μm multimode fiber and 1.25 mm ferrules with heat-shrink tubing (ThorLabs RJPSL4). Water was delivered using a solenoid valve triggered by custom behavior software running on a Teensy 4.0 board.

Training was split into 3 phases: habituation, shaping, and stimulation. During habituation, water-restricted mice were exposed to the enclosure and received a water reward at either of the two lateral ports, with a 10 second inter-trial-interval and 60 second timeout per 'trial'. Once the mice got water rewards on ≥65% of the total trial count for 2 consecutive days, they were moved on to shaping, where rewards were available on the left and right ports for 10 seconds only after triggering the center port. Mice that achieved ≥65% success rate for 2 consecutive days were moved on to the stimulation detection task.

For the detection task, trials were initiated by poking the center port. On every trial, masking LEDs (470 nm) were active for the duration of every trial, and optical stimulation was delivered to the cranial window using a fiber-coupled LED directly touching the glass window (590 nm, Thorlabs M590F3) on GO trials. The response period extended 500 ms after the stimulation presentation was over, followed by different tones to indicate success or failure, followed by a variable inter-trial interval. Licking during a GO trial resulted in an immediate water reward, and the trial was classified as a hit. Failing to lick during a GO trial ('miss' trial) triggered a 4 second timeout. Licking during a catch trial ('false alarm' or FA) resulted in an airpuff to the face, whereas not licking during a catch trial ('correct reject' or CR) was a correct trial, but unrewarded.

Mice gradually acclimated to the main task, starting with 'autoreward' where water was paired with stimulation for free. Mice were kept on autoreward until licking for 50% of rewards, usually just one session. Mice were then advanced to a session with only go-trials, where they had to lick during the response period to receive a water reward. After achieving performance of 50%, mice were advanced to the main task until they achieved sessions above criterion (D'>1). Controls could advance to the main task by associating masking light with reward.

Example 8—Replacing Embryonic Mouse Neurons with Human Stem Cell Derived Neurons Two cohorts of mice were used: one cohort was daily IP injected with 35 mg/kg cyclosporine, 4-5 days before implantation and every day until euthanasia, to immunocompromise the mice, and the other cohort had naïve mice. Identical to mouse-mouse surgeries were performed, albeit done in a biological safety cabinet to maximize sterility. Plasmids used during surgery include: pCAG-H2B-mRuby3-P2A-GCaMP7s; PCAG-ChR2(H134R)-tdTomato; Cag-mRuby3; and pCAG-ChrimsonR-tdTomato. Human neurons were obtained using a modified version of the protocol described in Nehme et al., *Cell Rep,* 23(8):2509-2523, 2018. The stem cells that were used (iP11N from ALSTEM) have been genetically modified to harbor a doxycycline inducible NGN2 cassette at the AAVS1 locus for rapid neuralization of stem cells. Nehme et al. used a lentiviral approach to insert the NGN2 cassette into the cells. Due to these differences, puromycin was not used for selection. EdU, an anti-mitotic, was used instead. The cells were also passaged on Day 3 and Day 5 due to excessive progenitor proliferation. FIG. 10A-10G show stem cell to human neuron differentiation from Day 1 to Day 7.

Following surgery, mice were subjected to the same behavioral testing (where applicable) as the mouse-mouse pour overs. After time, the mice were transcardially perfused with formalin, and their brains excised and processed for immunohistochemistry. The results of neuron differentiation include a massive immune response by the infiltration and activation of astrocytes (gfap); and microglia (iba1) around implant site. The results demonstrate that immune-compromization is necessary for grafting human cells into/onto the mouse cortex.

Example 9—Cell-Tethering

Figure 11B:
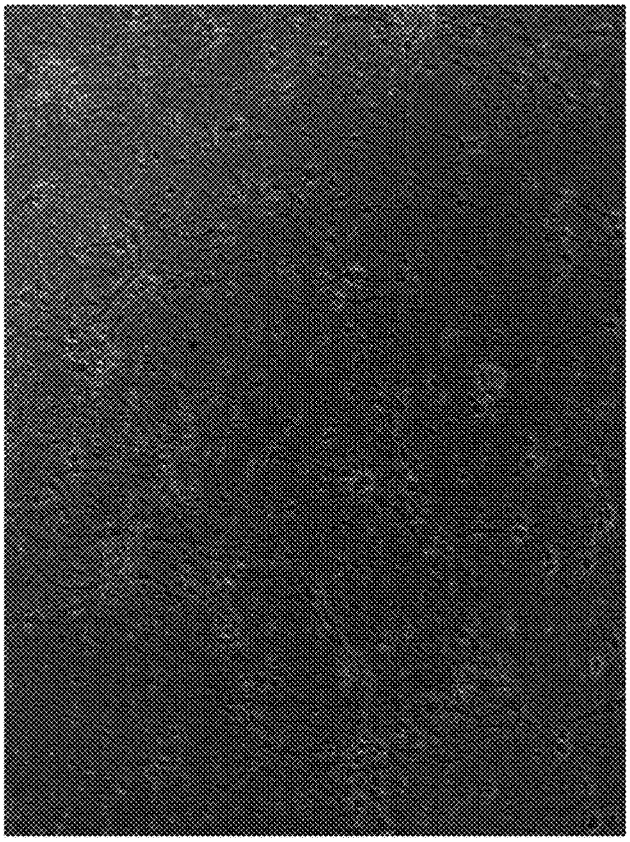
FIG. 11A-B show neuronal growth on an indium tin oxide (ITO) substrate in the presence of poly-D-lysine and laminin.
Figure 11A:
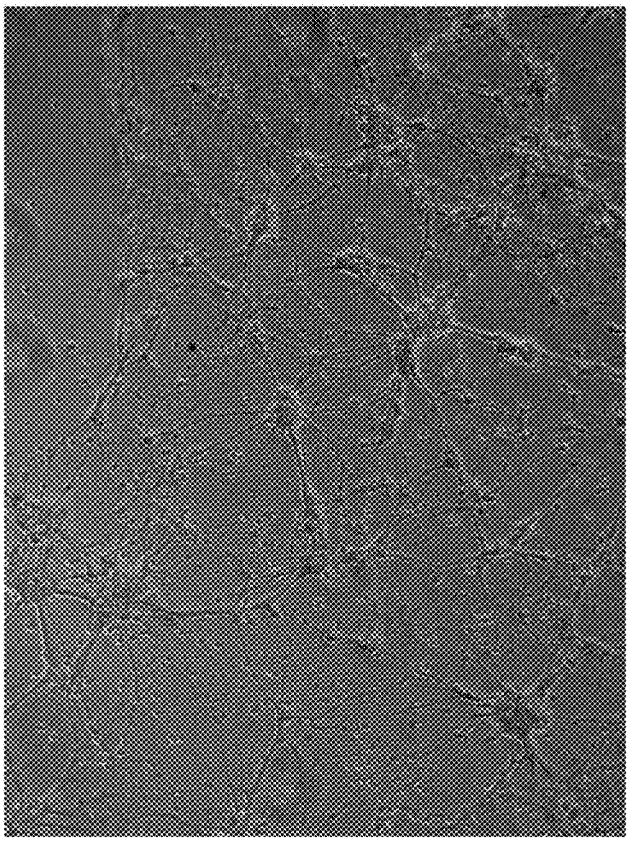

This example illustrates the development of an in vitro model to test the efficacy of standard coating on neural health. FIG. 11 shows neuronal growth on an indium tin oxide (ITO) substrate in the presence of poly-D-lysine and laminin. Neurospheres are cell aggregates (neural network) that consist of neural progenitor cells (NPCs) and are cultivated in the presence of growth factors. In the absence of growth factors and when seeded on 2D poly-D-lysin/laminin (PDL/LAM)-coated surfaces, NPC neurospheres migrate and differentiate into neurons, astrocytes, and oligodendrocytes, thereby generating complex networks. Hydrogel readily adheres to (PDL/LAM)-coated surfaces.

Modifications and variations of the present invention will be obvious to those skilled in the art from the foregoing detailed description and are intended to fall within the scope of the following claims. The teachings of all references cited herein are specifically incorporated by reference.

Informal Sequence Listing

SEQ ID NO: 1: pDNA:pCaGGs-H2B-mRuby3-P2A-G7s
Purpose: Delivers genes that express mRuby3 in the nucleus (transfected cell nuclei will emit 'red' fluorescence), and GCaMP (active neurons will emit 'green' fluorescence)
Sequence:

```
GACATTGATTATTGACTAGTTATTAATAGTAATCAATTACGGGGTCATTAGTTCATA
GCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGC
CAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACG
GTAAATGGCCCGCCTGGCATTATGCCCAGTACATGACCTTATGGGACTTTCCTACTT
GGCAGTACATCTACGTATTAGTCATCGCTATTACCATGGTCGAGGTGAGCCCCACGT
TCTGCTTCACTCTCCCCATCTCCCCCCCCTCCCCACCCCCAATTTTGTATTTATTTATT
TTTTAATTATTTTGTGCAGCGATGGGGGCGGGGGGGGGGGGGGGGCGCGCGCCAGG
CGGGGCGGGGCGGGGCGAGGGGCGGGGCGGGGCGAGGCGGAGAGGTGCGGCGGC
AGCCAATCAGAGCGGCGCGCTCCGAAAGTTTCCTTTTATGGCGAGGCGGCGGCGGC
GGCGGCCCTATAAAAAGCGAAGCGCGCGGCGGGCGGGAGTCGCTGCGCGCTGCCTT
CGCCCCGTGCCCCGCTCCGCCGCCGCCTCGCGCCGCCCGCCCCGGCTCTGACTGACC
GCGTTACTCCCACAGGTGAGCGGGCGGGACGGCCCTTCTCCTCCGGGCTGTAATTAG
CGCTTGGTTTAATGACGGCTTGTTTCTTTTCTGTGGCTGCGTGAAAGCCTTGAGGGGC
TCCGGGAGGGCCCTTTGTGCGGGGGGAGCGGCTCGGGGGGTGCGTGCGTGTGTGTG
TGCGTGGGGAGCGCCGCGTGCGGCTCCGCGCTGCCCGGCGGCTGTGAGCGCTGCGG
GCGCGGCGCGGGGCTTTGTGCGCTCCGCAGTGTGCGCGAGGGGAGCGCGGCCGGGG
GCGGTGCCCCGCGGTGCGGGGGGGGCTGCGAGGGGAACAAAGGCTGCGTGCGGGG
TGTGTGCGTGGGGGGGTGAGCAGGGGGTGTGGGCGCGTCGGTCGGGCTGCAACCCC
CCCTGCACCCCCCTCCCCGAGTTGCTGAGCACGGCCCGGCTTCGGGTGCGGGGCTCC
GTACGGGGCGTGGCGCGGGGCTCGCCGTGCCGGGCGGGGGGTGGCGGCAGGTGGG
GGTGCCGGGCGGGGCGGGGCCGCCTCGGGCCGGGGAGGGCTCGGGGGAGGGGCGC
GGCGGCCCCCGGAGCGCCGGCGGCTGTCGAGGCGCGGCGAGCCGCAGCCATTGCCT
TTTATGGTAATCGTGCGAGAGGGCGCAGGGACTTCCTTTGTCCCAAATCTGTGCGGA
GCCGAAATCTGGGAGGCGCCGCCGCACCCCCTCTAGCGGGCGCGGGGCGAAGCGGT
GCGGCGCCGGCAGGAAGGAAATGGGCGGGGAGGGCCTTCGTGCGTCGCCGCGCCGC
CGTCCCCTTCTCCCTCTCCAGCCTCGGGGCTGTCCGCGGGGGGACGGCTGCCTTCGG
GGGGGACGGGGCAGGGCGGGGTTCGGCTTCTGGCGTGTGACCGGCGGCTCTAGAGC
CTCTGCTAACCATGTTCATGCCTTCTTCTTTTTCCTACAGCTCCTGGGCAACGTGCTG
GTTATTGTGCTGTCTCATCATTTTGGCAAAGAATTCGGTACCGCGGGCCCGGGATCC
ACCGGTAGCGGCCGCGGCCGCTATGCCAGAGCCAGCGAAGTCTGCTCCCGCCCCGA
AAAAGGGCTCCAAGAAGGCGGTGACTAAGGCGCAGAAGAAAGGCGGCAAGAAGCG
CAAGCGCAGCCGCAAGGAGAGCTATTCCATCTATGTGTACAAGGTTCTGAAGCAGG
TCCACCCTGACACCGGCATTTCGTCCAAGGCCATGGGCATCATGAATTCGTTTGTGA
ACGACATTTTCGAGCGCATCGCAGGTGAGGCTTCCCGCCTGGCGCATTACAACAAGC
GCTCGACCATCACCTCCAGGGAGATCCAGACGGCCGTGCGCCTGCTGCTGCCTGGG
GAGTTGGCCAAGCACGCCGTGTCCGAGGGTACTAAGGCCATCACCAAGTACACCAG
CGCTAAGGCGGCCGCTATGGTGTCTAAGGGCGAAGAGCTGATCAAGGAAAATATGC
GTATGAAGGTGGTCATGGAAGGTTCGGTCAACGGCCACCAATTCAAATGCACAGGT
GAAGGAGAAGGCAGACCGTACGAGGGAGTGCAAACCATGAGGATCAAAGTCATCG
AGGGAGGACCCCTGCCATTTGCCTTTGACATTCTTGCCACGTCGTTCATGTATGGCA
GCCGTACCTTTATCAAGTACCCGGCCGACATCCCTGATTTCTTTAAACAGTCCTTTCC
TGAGGGTTTTACTTGGGAAAGAGTTACGAGATACGAAGATGGTGGAGTCGTCACCG
TCACGCAGGACACCAGCCTTGAGGATGGCGAGCTCGTCTACAACGTCAAGGTCAGA
GGGGTAAACTTTCCCTCCAATGGTCCCGTGATGCAGAAGAAGACCAAGGGTTGGGA
GCCTAATACAGAGATGATGTATCCAGCAGATGGTGGTCTGAGAGGATACACTGACA
TCGCACTGAAAGTTGATGGTGGTGGCCATCTGCACTGCAACTTCGTGACAACTTACA
GGTCAAAAAAGACCGTCGGGAACATCAAGATGCCCGGTGTCCATGCCGTTGATCAC
CGCCTGGAAAGGATCGAGGAGAGTGACAATGAAACCTACGTAGTGCAAAGAGAAG
TGGCAGTTGCCAAATACAGCAACCTTGGTGGTGGCATGGACGAGCTGTACAAGGGA
TCCGGAGCCACGAACTTCTCTCTGTTAAAGCAAGCAGGAGACGTCGAAGAAAACCC
CGGTCCTGCCACCATGGGTTCTCATCATCATCATCATCATGGTATGGCTAGCATGAC
TGGTGGACAGCAAATGGGTCGGGATCTGTACGACGATGACGATAAGGATCTCGCCA
CCATGGTCGACTCATCACGTCGTAAGTGGAATAAGACAGGTCACGCAGTCAGAGTG
ATAGGTCGGCTGAGCTCACTCGAGAACGTCTATATCAAGGCCGACAAGCAGAAGAA
CGGCATCAAGGCGAACTTCCACATCCGCCACAACATCGAGGACGGCGGCGTGCAGC
```

-continued

| Informal Sequence Listing |
| --- |

```
TCGCCTACCACTACCAGCAGAACACCCCCATCGGCGACGGCCCCGTGCTGCTGCCCG
ACAACCACTACCTGAGCGTGCAGTCCAAACTTTCGAAAGACCCCAACGAGAAGCGC
GATCACATGGTCCTGCTGGAGTTCGTGACCGCCGCCGGGATCACTCTCGGCATGGAC
GAGCTGTACAAGGGCGGTACCGGAGGGAGCATGGTGAGCAAGGGCGAGGAGCTGT
TCACCGGGGTGGTGCCCATCCTGGTCGAGCTGGACGGCGACGTAAACGGCCACAAG
TTCAGCGTGTCCGGCGAGGGTGAGGGCGATGCCACCTACGGCAAGCTGACCCTGAA
GTTCATCTGCACCACCGGCAAGCTGCCCGTGCCCTGGCCCACCCTCGTGACCACCCT
GACCTACGGCGTGCAGTGCTTCAGCCGCTACCCCGACCACATGAAGCAGCACGACT
TCTTCAAGTCCGCCATGCCCGAAGGCTACATCCAGGAGCGCACCATCTTCTTCAAGG
ACGACGGCAACTACAAGACCCGCGCCGAGGTGAAGTTCGAGGGCGACACCCTGGTG
AACCGCATCGAGCTTAAGGGCATCGACTTCAAGGAGGACGGCAACATCCTGGGGCA
CAAGCTGGAGTACAACCTTCCTGACCAACTGACTGAAGAGCAGATCGCAGAATTTA
AAGAGCTTTTCTCCCTATTTGACAAGGACGGGGATGGGACAATAACAACCAAGGAG
CTGGGGACGGTGATGCGGTCTCTGGGGCAGAACCCCACAGAAGCAGAGCTGCAGGA
CATGATCAATGAAGTAGATGCCGACGGTGACGGCACAATCGACTTCCCTGAGTTCCT
GACAATGATGGCAAGAAAAATGAAATACAGGGACACGGAAGAAGAAATTAGAGAA
GCGTTCGGTGTGTTTGATAAGGATGGCAATGGCTACATCAGTGCAGCAGAGCTTCGC
CACGTGATGACAAACCTTGGAGAGAAGTTAACAGATGAAGAGGTTGATGAAATGAT
CAGGGAAGCAGACATCGATGGGGATGGTCAGGTAAACTACGAAGAGTTTGTACAAA
TGATGACAGCGAAGTGAGTAAGTATCAAGGTTACAAGACAGGTTTAAGGAGACCAA
TAGAAACTGGGCTTGTCGAGACAGAGAAGACTCTTGCGTTTCTGATAGGCACCTATT
GGTCTTACTGACATCCACTTTGCCTTTCTCTCCACAGGTGTCGACAATCAACCTCTGG
ATTACAAAATTTGTGAAAGATTGACTGGTATTCTTAACTATGTTGCTCCTTTTACGCT
ATGTGGATACGCTGCTTTAATGCCTTTGTATCATGCTATTGCTTCCCGTATGGCTTTC
ATTTTCTCCTCCTTGTATAAATCCTGGTTGCTGTCTCTTTATGAGGAGTTGTGGCCCG
TTGTCAGGCAACGTGGCGTGGTGTGCACTGTGTTTGCTGACGCAACCCCCACTGGTT
GGGGCATTGCCACCACCTGTCAGCTCCTTTCCGGGACTTTCGCTTTCCCCCTCCCTAT
TGCCACGGCGGAACTCATCGCCGCCTGCCTTGCCCGCTGCTGGACAGGGGCTCGGCT
GTTGGGCACTGACAATTCCGTGGTGTTGTCGGGGAAGCTGACGTCCTTTCCATGGCT
GCTCGCCTGTGTTGCCACCTGGATTCTGCGCGGGACGTCCTTCTGCTACGTCCCTTCG
GCCCTCAATCCAGCGGACCTTCCTTCCCGCGGCCTGCTGCCGGCTCTGCGGCCTCTTC
CGCGTCTTCGCCTTCGCCCTCAGACGAGTCGGATCTCCCTTTGGGCCGCCTCCCCGCC
TGGAATTCGAGCTCGGTACGATCAGCCTCGACTGTGCCTTCTAGTTGCCAGCCATCT
GTTGTTTGCCCCTCCCCCGTGCCTTCCTTGACCCTGGAAGGTGCCACTCCCACTGTCC
TTTCCTAATAAAATGAGGAAATTGCATCGCATTGTCTGAGTAGGTGTCATTCTATTCT
GGGGGGTGGGGTGGGGCAGGACAGCAAGGGGGAGGATTGGGAAGACAATAGCCCA
GCTTTTGTTCCCTTTAGTGAGGGTTAATTGCGCGCTTGGCGTAATCATGGTCATAGCT
GTTTCCTGTGTGAAATTGTTATCCGCTAATTCACTCCTCAGGTGCAGGCTGCCTATCA
GAAGGTGGTGGCTGGTGTGGCCAATGCCCTGGCTCACAAATACCACTGAGATCTTTT
TCCCTCTGCCAAAAATTATGGGGACATCATGAAGCCCCTTGAGCATCTGACTTCTGG
CTAATAAAGGAAATTTATTTTCATTGCAATAGTGTGTTGGAATTTTTTGTGTCTCTCA
CTCGGAAGGACATATGGGAGGGCAAATCATTTAAAACATCAGAATGAGTATTTGGT
TTAGAGTTTGGCAACATATGCCCATATGCTGGCTGCCATGAACAAAGGTTGGCTATA
AAGAGGTCATCAGTATATGAAACAGCCCCCTGCTGTCCATTCCTTATTCCATAGAAA
AGCCTTGACTTGAGGTTAGATTTTTTTTATATTTTGTTTTGTGTTATTTTTTTCTTTAA
CATCCCTAAAATTTTCCTTACATGTTTTACTAGCCAGATTTTTCCTCCTCTCCTGACTA
CTCCCAGTCATAGCTGTCCCTCTTCTCTTATGGAGATCCCTCGACCTGCAGCCCAAGC
TTGGCGTAATCATGGTCATAGCTGTTTCCTGTGTGAAATTGTTATCCGCTCACAATTC
CACACAACATACGAGCCGGAAGCATAAAGTGTAAAGCCTGGGGTGCCTAATGAGTG
AGCTAACTCACATTAATTGCGTTGCGCTCACTGCCCGCTTTCCAGTCGGGAAACCTG
TCGTGCCAGCGGATCCGCATCTCAATTAGTCAGCAACCATAGTCCCGCCCCTAACTC
CGCCCATCCCGCCCCTAACTCCGCCCAGTTCCGCCCATTCTCCGCCCCATGGCTGACT
AATTTTTTTTATTTATGCAGAGGCCGAGGCCGCCTCGGCCTCTGAGCTATTCCAGAA
GTAGTGAGGAGGCTTTTTTGGAGGCCTAGGCTTTTGCAAAAAGCTAACTTGTTTATT
GCAGCTTATAATGGTTACAAATAAAGCAATAGCATCACAAATTTCACAAATAAAGC
ATTTTTTTCACTGCATTCTAGTTGTGGTTTGTCCAAACTCATCAATGTATCTTATCATG
TCTGGATCCGCTGCATTAATGAATCGGCCAACGCGCGGGGAGAGGCGGTTTGCGTAT
TGGGCGCTCTTCCGCTTCCTCGCTCACTGACTCGCTGCGCTCGGTCGTTCGGCTGCGG
CGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAA
AAGGCCGCGTTGCTGGCGTTTTTCCATAGGCTCCGCCCCCCTGACGAGCATCACAAA
AATCGACGCTCAAGTCAGAGGTGGCGAAACCCGACAGGACTATAAAGATACCAGGC
GTTTCCCCCTGGAAGCTCCCTCGTGCGCTCTCCTGTTCCGACCCTGCCGCTTACCGGA
TACCTGTCCGCCTTTCTCCCTTCGGGAAGCGTGGCGCTTTCTCATAGCTCACGCTGTA
GGTATCTCAGTTCGGTGTAGGTCGTTCGCTCCAAGCTGGGCTGTGTGCACGAACCCC
CCGTTCAGCCCGACCGCTGCGCCTTATCCGGTAACTATCGTCTTGAGTCCAACCCGG
TAAGACACGACTTATCGCCACTGGCAGCAGCCACTGGTAACAGGATTAGCAGAGCG
AGGTATGTAGGCGGTGCTACAGAGTTCTTGAAGTGGTGGCCTAACTACGGCTACACT
AGAAGAACAGTATTTGGTATCTGCGCTCTGCTGAAGCCAGTTACCTTCGGAAAAAGA
GTTGGTAGCTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTGATCTTT
TCTACGGGGTCTGACGCTCAGTGGAACGAAAACTCACGTTAAGGGATTTTGGTCATG
AGATTATCAAAAAGGATCTTCACCTAGATCCTTTTAAATTAAAAATGAAGTTTTAAA
TCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCCCCG
TCGTGTAGATAACTACGATACGGGAGGGCTTACCATCTGGCCCCAGTGCTGCAATGA
TACCGCGAGACCCACGCTCACCGGCTCCAGATTTATCAGCAATAAACCAGCCAGCC
```

-continued

| Informal Sequence Listing |
| --- |

GGAAGGGCCGAGCGCAGAAGTGGTCCTGCAACTTTATCCGCCTCCATCCAGTCTATT
AATTGTTGCCGGGAAGCTAGAGTAAGTAGTTCGCCAGTTAATAGTTTGCGCAACGTT
GTTGCCATTGCTACAGGCATCGTGGTGTCACGCTCGTCGTTTGGTATGGCTTCATTCA
GCTCCGGTTCCCAACGATCAAGGCGAGTTACATGATCCCCCATGTTGTGCAAAAAAG
CGGTTAGCTCCTTCGGTCCTCCGATCGTTGTCAGAAGTAAGTTGGCCGCAGTGTTAT
CACTCATGGTTATGGCAGCACTGCATAATTCTCTTACTGTCATGCCATCCGTAAGAT
GCTTTTCTGTGACTGGTGAGTACTCAACCAAGTCATTCTGAGAATAGTGTATGCGGC
GACCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGATC
TTACCGCTGTTGAGATCCAGTTCGATGTAACCCACTCGTGCACCCAACTGATCTTCA
GCATCTTTTACTTTCACCAGCGTTTCTGGGTGAGCAAAAACAGGAAGGCAAAATGCC
GCAAAAAAGGGAATAAGGGCGACACGGAAATGTTGAATACTCATACTCTTCCTTTTT
CAATATTATTGAAGCATTTATCAGGGTTATTGTCTCATGAGCGGATACATATTTGAA
TGTATTTAGAAAAATAAACAAATAGGGGTTCCGCGCACATTTCCCCGAAAAGTGCC
ACCTGGTC
SEQ ID NO: 2 pDNA: pCaGGs-ChR2(H134R)-tdTomato
Purpose: Delivers genes that express the opsin variant
'channelrhodopsin-H134R' (allowing cells to be optically
stimulated/activated with a specific wavelength), and
td-Tomato marker
(transfected neurons will emit a 'red' fluorescence)
Sequence:
GACATTGATTATTGACTAGTTATTAATAGTAATCAATTACGGGGTCATTAGTTCATA
GCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGC
CAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACG
GTAAATGGCCCGCCTGGCATTATGCCCAGTACATGACCTTATGGGACTTTCCTACTT
GGCAGTACATCTACGTATTAGTCATCGCTATTACCATGGTCGAGGTGAGCCCCACGT
TCTGCTTCACTCTCCCCATCTCCCCCCCCTCCCCACCCCCAATTTTGTATTTATTTATT
TTTTAATTATTTTGTGCAGCGATGGGGGCGGGGGGGGGGGGGGGGCGCGCGCCAGG
CGGGGCGGGGCGGGGCGAGGGGCGGGGCGGGGCGAGGCGGAGAGGTGCGGCGGC
AGCCAATCAGAGCGGCGCGCTCCGAAAGTTTCCTTTTATGGCGAGGCGGCGGCGGC
GGCGGCCCTATAAAAAGCGAAGCGCGCGGCGGGCGGGAGTCGCTGCGCGCTGCCTT
CGCCCCGTGCCCCGCTCCGCCGCCGCCTCGCGCCGCCCGCCCCGGCTCTGACTGACC
GCGTTACTCCCACAGGTGAGCGGGCGGGACGGCCCTTCTCCTCCGGGCTGTAATTAG
CGCTTGGTTTAATGACGGCTTGTTTCTTTTCTGTGGCTGCGTGAAAGCCTTGAGGGGC
TCCGGGAGGGCCCTTTGTGCGGGGGGAGCGGCTCGGGGGGTGCGTGCGTGTGTGTG
TGCGTGGGGAGCGCCGCGTGCGGCTCCGCGCTGCCCGGCGGCTGTGAGCGCTGCGG
GCGCGGCGCGGGGCTTTGTGCGCTCCGCAGTGTGCGCGAGGGGAGCGCGGCCGGGG
GCGGTGCCCCGCGGTGCGGGGGGGGCTGCGAGGGGAACAAAGGCTGCGTGCGGGG
TGTGTGCGTGGGGGGGTGAGCAGGGGGTGTGGGCGCGTCGGTCGGGCTGCAACCCC
CCCTGCACCCCCCTCCCCGAGTTGCTGAGCACGGCCCGGCTTCGGGTGCGGGGCTCC
GTACGGGGCGTGGCGCGGGGCTCGCCGTGCCGGGCGGGGGGTGGCGGCAGGTGGG
GGTGCCGGGCGGGGCGGGGCCGCCTCGGGCCGGGGAGGGCTCGGGGGAGGGGCGC
GGCGGCCCCCGGAGCGCCGGCGGCTGTCGAGGCGCGGCGAGCCGCAGCCATTGCCT
TTTATGGTAATCGTGCGAGAGGGCGCAGGGACTTCCTTTGTCCCAAATCTGTGCGGA
GCCGAAATCTGGGAGGCGCCGCCGCACCCCCTCTAGCGGGCGCGGGGCGAAGCGGT
GCGGCGCCGGCAGGAAGGAAATGGGCGGGGAGGGCCTTCGTGCGTCGCCGCGCCGC
CGTCCCCTTCTCCCTCTCCAGCCTCGGGGCTGTCCGCGGGGGGACGGCTGCCTTCGG
GGGGGACGGGGCAGGGCGGGGTTCGGCTTCTGGCGTGTGACCGGCGGCTCTAGAGC
CTCTGCTAACCATGTTCATGCCTTCTTCTTTTTCCTACAGCTCCTGGGCAACGTGCTG
GTTATTGTGCTGTCTCATCATTTTGGCAAAGAATTCGGTACCGCGGGCCCGGGATCC
ACCGGTAGCGGCCGCGGCCGCTgccaccatggactatggcggcgctttgtctgccgtcggacgcgaa
cttttgttcgttactaatcctgtggtggtgaacgggtccgtcctggtccctgaggatcaat
gttactgtgccggatggattgaatctcgcggcacgaacggcgctcagaccgcgtcaaa
tgtcctgcagtggcttgcagcaggattcagcattttgctgctgatgttctatgcctacc
aaacctggaaatctacatgcggctgggaggagatctatgtgtgcgccattgaaatggttaag
gtgattctcgagttctttttgagtttaagaatccctctatgctctaccttgccacaggacaccg
ggtgcagtggctgcgctatgcagagtggctgctcacttgtcctgtcatccttatccgcctga
gcaacctcaccggcctgagcaacgactacagcaggagaaccatgggactccttgtctcagaca
tcgggactatcgtgtgggggctaccagcgccatggcaaccggctatgttaaagtcatcttc
ttttgtcttggattgtgctatggcgcgaacacatttttcacgccgccaaagcatatatcga
gggttatcatactgtgccaaagggtcggtgccgccaggtcgtgaccggcatggcatggctg
tttttcgtgagctggggtatgttcccaattctcttcattttggggcccgaaggttttggcgtc
ctgagcgtctatggctccaccgtaggtcacacgattattgatctgatgagtaaaaattgtt
gggggttgttgggacactacctgcgcgtcctgatccacgagcacatattgattcacgga
gatatccgcaaaaccaccaaactgaacatcggcggaacggagatcgaggtcgagactctcgtc
gaagacgaagccgaggccggagccgtgccagccgcggccgtgagcaagggcgaggaggt
catcaaagagttcatgcgcttcaaggtgcgcatggagggctccatgaacggccacgagttcgag
atcgagggcgagggcgagggccgcccctacgagggcacccagaccgccaagctgaaggtga
ccaagggcggccccctgcccttcgcctgggacatcctgtccccccagttcatgtac
ggctccaaggcgtacgtgaagcaccccgccgacatccccgattacaagaagctgtccttcccc
gagggcttcaagtgggagcgcgtgatgaacttcgaggacggcggtctggtgaccgtgacccag
gactcctccctgcaggacggcacgctgatctacaaggtgaagatgcgcggcaccaa
cttcccccccgacggccccgtaatgcagaagaagaccatgggctgggaggcctcc
accgagcgcctgtaccccgcgacggcgtgctgaagggcgagatccaccaggccctgaag -continued

| Informal Sequence Listing |
| --- |
| ctgaaggacggcggccactacctggtggagttcaagaccatctacatggccaagaagcccg<br>tgcaactgcccggctactactacgtggacaccaagctggacatcacctcccacaacgaggact<br>acaccatcgtggaacagtacgagcgctccgagggccgccaccacctgttcctggggcat<br>ggcaccggcagcaccggcagcggcagctccggcaccgcctcctccgaggacaaca<br>acatggccgtcatcaaagagttcatgcgcttcaaggtgcgcatggagggctccatgaacgg<br>ccacgagttcgagatcgagggcgagggcgagggccgcccctacgagggcacccagac<br>cgccaagctgaaggtgaccaagggcggcccccctgcccttcgcctgggacatcctg<br>tccccccagttcatgtacggctccaaggcgtacgtgaagcaccccgccgacatcccc<br>gattacaagaagctgtccttccccgagggcttcaagtgggagcgcgtgatgaacttcga<br>ggacggcggtctggtgaccgtgacccaggactcctccctgcaggacggcacgctg<br>atctacaaggtgaagatgcgcggcaccaacttcccccccgacggccccgtaatg<br>cagaagaagaccatgggctgggaggcctccaccgagcgcctgtaccccgcga<br>cggcgtgctgaagggcgagatccaccaggccctgaagctgaaggacggcggc<br>cactacctggtggagttcaagaccatctacatggccaagaagcccgtgcaactgc<br>ccggctactactacgtggacaccaagctggacatcacctcccacaacgaggact<br>acaccatcgtggaacagtacgagcgctccgagggccgccaccacctgttc<br>ctgtacggcatggacgagctgtacaagtaaGTAAGTATCAAGGTTACAAG<br>ACAGGTTTAAGGAGACCAATAGAAACTGGGCTTGTCGAGACAGAGAAGACTCTTGC<br>GTTTCTGATAGGCACCTATTGGTCTTACTGACATCCACTTTGCCTTTCTCTCCACAGG<br>TGTCGACAATCAACCTCTGGATTACAAAATTTGTGAAAGATTGACTGGTATTCTTAA<br>CTATGTTGCTCCTTTTACGCTATGTGGATACGCTGCTTTAATGCCTTTGTATCATGCT<br>ATTGCTTCCCGTATGGCTTTCATTTTCTCCTCCTTGTATAAATCCTGGTTGCTGTCTCT<br>TTATGAGGAGTTGTGGCCCGTTGTCAGGCAACGTGGCGTGGTGTGCACTGTGTTTGC<br>TGACGCAACCCCCACTGGTTGGGGCATTGCCACCACCTGTCAGCTCCTTTCCGGGAC<br>TTTCGCTTTCCCCCTCCCTATTGCCACGGCGGAACTCATCGCCGCCTGCCTTGCCCGC<br>TGCTGGACAGGGGCTCGGCTGTTGGGCACTGACAATTCCGTGGTGTTGTCGGGGAAG<br>CTGACGTCCTTTCCATGGCTGCTCGCCTGTGTTGCCACCTGGATTCTGCGCGGGACGT<br>CCTTCTGCTACGTCCCTTCGGCCCTCAATCCAGCGGACCTTCCTTCCCGCGGCCTGCT<br>GCCGGCTCTGCGGCCTCTTCCGCGTCTTCGCCTTCGCCCTCAGACGAGTCGGATCTCC<br>CTTTGGGCCGCCTCCCCGCCTGGAATTCGAGCTCGGTACGATCAGCCTCGACTGTGC<br>CTTCTAGTTGCCAGCCATCTGTTGTTTGCCCCTCCCCCGTGCCTTCCTTGACCCTGGA<br>AGGTGCCACTCCCACTGTCCTTTCCTAATAAAATGAGGAAATTGCATCGCATTGTCT<br>GAGTAGGTGTCATTCTATTCTGGGGGGTGGGGTGGGGCAGGACAGCAAGGGGGAGG<br>ATTGGGAAGACAATAGCCCAGCTTTTGTTCCCTTTAGTGAGGGTTAATTGCGCGCTT<br>GGCGTAATCATGGTCATAGCTGTTTCCTGTGTGAAATTGTTATCCGCTAATTCACTCC<br>TCAGGTGCAGGCTGCCTATCAGAAGGTGGTGGCTGGTGTGGCCAATGCCCTGGCTCA<br>CAAATACCACTGAGATCTTTTTCCCTCTGCCAAAAATTATGGGGACATCATGAAGCC<br>CCTTGAGCATCTGACTTCTGGCTAATAAAGGAAATTTATTTTCATTGCAATAGTGTGT<br>TGGAATTTTTTGTGTCTCTCACTCGGAAGGACATATGGGAGGGCAAATCATTTAAAA<br>CATCAGAATGAGTATTTGGTTTAGAGTTTGGCAACATATGCCCATATGCTGGCTGCC<br>ATGAACAAAGGTTGGCTATAAAGAGGTCATCAGTATATGAAACAGCCCCCTGCTGT<br>CCATTCCTTATTCCATAGAAAAGCCTTGACTTGAGGTTAGATTTTTTTTATATTTTGTT<br>TTGTGTTATTTTTTTCTTTAACATCCCTAAAATTTTCCTTACATGTTTTACTAGCCAGA<br>TTTTTCCTCCTCTCCTGACTACTCCCAGTCATAGCTGTCCCTCTTCTCTTATGGAGATC<br>CCTCGACCTGCAGCCCAAGCTTGGCGTAATCATGGTCATAGCTGTTTCCTGTGTGAA<br>ATTGTTATCCGCTCACAATTCCACACAACATACGAGCCGGAAGCATAAAGTGTAAA<br>GCCTGGGGTGCCTAATGAGTGAGCTAACTCACATTAATTGCGTTGCGCTCACTGCCC<br>GCTTTCCAGTCGGGAAACCTGTCGTGCCAGCGGATCCGCATCTCAATTAGTCAGCAA<br>CCATAGTCCCGCCCCTAACTCCGCCCATCCCGCCCCTAACTCCGCCCAGTTCCGCCC<br>ATTCTCCGCCCCATGGCTGACTAATTTTTTTTATTTATGCAGAGGCCGAGGCCGCCTC<br>GGCCTCTGAGCTATTCCAGAAGTAGTGAGGAGGCTTTTTTGGAGGCCTAGGCTTTTG<br>CAAAAAGCTAACTTGTTTATTGCAGCTTATAATGGTTACAAATAAAGCAATAGCATC<br>ACAAATTTCACAAATAAAGCATTTTTTTCACTGCATTCTAGTTGTGGTTTGTCCAAAC<br>TCATCAATGTATCTTATCATGTCTGGATCCGCTGCATTAATGAATCGGCCAACGCGC<br>GGGGAGAGGCGGTTTGCGTATTGGGCGCTCTTCCGCTTCCTCGCTCACTGACTCGCT<br>GCGCTCGGTCGTTCGGCTGCGGCGAGCGGTATCAGCTCACTCAAAGGCGGTAATAC<br>GGTTATCCACAGAATCAGGGGATAACGCAGGAAAGAACATGTGAGCAAAAGGCCA<br>GCAAAAGGCCAGGAACCGTAAAAAGGCCGCGTTGCTGGCGTTTTTCCATAGGCTCC<br>GCCCCCCTGACGAGCATCACAAAAATCGACGCTCAAGTCAGAGGTGGCGAAACCCG<br>ACAGGACTATAAAGATACCAGGCGTTTCCCCCTGGAAGCTCCCTCGTGCGCTCTCCT<br>GTTCCGACCCTGCCGCTTACCGGATACCTGTCCGCCTTTCTCCCTTCGGGAAGCGTG<br>GCGCTTTCTCATAGCTCACGCTGTAGGTATCTCAGTTCGGTGTAGGTCGTTCGCTCCA<br>AGCTGGGCTGTGTGCACGAACCCCCCGTTCAGCCCGACCGCTGCGCCTTATCCGGTA<br>ACTATCGTCTTGAGTCCAACCCGGTAAGACACGACTTATCGCCACTGGCAGCAGCCA<br>CTGGTAACAGGATTAGCAGAGCGAGGTATGTAGGCGGTGCTACAGAGTTCTTGAAG<br>TGGTGGCCTAACTACGGCTACACTAGAAGAACAGTATTTGGTATCTGCGCTCTGCTG<br>AAGCCAGTTACCTTCGGAAAAAGAGTTGGTAGCTCTTGATCCGGCAAACAAACCAC<br>CGCTGGTAGCGGTGGTTTTTTTGTTTGCAAGCAGCAGATTACGCGCAGAAAAAAAGG<br>ATCTCAAGAAGATCCTTTGATCTTTTCTACGGGGTCTGACGCTCAGTGGAACGAAAA<br>CTCACGTTAAGGGATTTTGGTCATGAGATTATCAAAAAGGATCTTCACCTAGATCCT<br>TTTAAATTAAAAATGAAGTTTTAAATCAATCTAAAGTATATATGAGTAAACTTGGTC<br>TGACAGTTACCAATGCTTAATCAGTGAGGCACCTATCTCAGCGATCTGTCTATTTCGT<br>TCATCCATAGTTGCCTGACTCCCCGTCGTGTAGATAACTACGATACGGGAGGGCTTA<br>CCATCTGGCCCCAGTGCTGCAATGATACCGCGAGACCCACGCTCACCGGCTCCAGAT<br>TTATCAGCAATAAACCAGCCAGCCGGAAGGGCCGAGCGCAGAAGTGGTCCTGCAAC<br>TTTATCCGCCTCCATCCAGTCTATTAATTGTTGCCGGGAAGCTAGAGTAAGTAGTTC<br>GCCAGTTAATAGTTTGCGCAACGTTGTTGCCATTGCTACAGGCATCGTGGTGTCACG |

-continued

Informal Sequence Listing

CTCGTCGTTTGGTATGGCTTCATTCAGCTCCGGTTCCCAACGATCAAGGCGAGTTAC
ATGATCCCCCATGTTGTGCAAAAAAGCGGTTAGCTCCTTCGGTCCTCCGATCGTTGT
CAGAAGTAAGTTGGCCGCAGTGTTATCACTCATGGTTATGGCAGCACTGCATAATTC
TCTTACTGTCATGCCATCCGTAAGATGCTTTTCTGTGACTGGTGAGTACTCAACCAAG
TCATTCTGAGAATAGTGTATGCGGCGACCGAGTTGCTCTTGCCCGGCGTCAATACGG
GATAATACCGCGCCACATAGCAGAACTTTAAAAGTGCTCATCATTGGAAAACGTTCT
TCGGGGCGAAAACTCTCAAGGATCTTACCGCTGTTGAGATCCAGTTCGATGTAACCC
ACTCGTGCACCCAACTGATCTTCAGCATCTTTTACTTTCACCAGCGTTTCTGGGTGAG
CAAAAACAGGAAGGCAAAATGCCGCAAAAAAGGGAATAAGGGCGACACGGAAATG
TTGAATACTCATACTCTTCCTTTTTCAATATTATTGAAGCATTTATCAGGGTTATTGT
CTCATGAGCGGATACATATTTGAATGTATTTAGAAAAATAAACAAATAGGGGTTCCG
CGCACATTTCCCCGAAAAGTGCCACCTGGTC

SEQ ID NO: 3 pDNA: pCAG-ChRimson-tdTomato
Purpose: Delivers genes that express the opsin variant
'ChrimsonR" (allowing cells to be optically stimulated/activated
with a specific wavelength), and td-Tomato marker (transfected
neurons will emit a 'red' fluorescence)
Sequence:
Atggggacctggatgctgacgaaggctcgcgaggctgtgagcagccacagtgccct
gctcagaagccccaagctcgtcagtcaagccggttctccgtttgcactcaggag
cacgggcaggcgagtggcccctagttctgggggcagcgggggatccgccaccatggct
gagctgatcagcagcgccaccagatctctgtttgccgccggaggcatcaaccctt
ggcctaacccctaccaccacgaggacatgggctgtggaggaatgacacctacaggcgagtg
cttcagcaccgagtggtggtgtgacccttcttacggactgagcgacgccggatacgg
atattgcttcgtggaggccacaggcggctacctggtcgtgggagtggagaagaagcaggcttg
gctgcacagcagaggcacaccaggagaaaagatcggcgcccaggtctgccagtggattgctttca
gcatcgccatcgccctgctgacattctacggcttcagcgcctggaaggccacttgcgg
ttgggaggaggtctacgtctgttgcgtcgaggtgctgttcgtgaccctggagatcttca
aggagttcagcagccccgccacagtgtacctgtctaccggcaaccacgcctattgc
ctgcgctacttcgagtggctgctgtcttgccccgtgatcctgatcagactgagcaacct
gagcggcctgaagaacgactacagcaagcggaccatgggcctgatcgtgtcttgcg
tgggaatgatcgtgttcggcatggccgcaggactggctaccgattggctcaagtggc
tgctgtatatcgtgtcttgcatctacggcggctacatgtacttccaggccgccaagtgct
acgtggaagccaaccacagcgtgcctaaaggccattgccgcatggtcgtgaagctgatggc
ctacgcttacttcgcctcttggggcagctacccaatcctctgggcagtgggaccagaaggact
gctgaagctgagcccttacgccaacagcatcggccacagcatctgcgacatca
tcgccaaggagttttggaccttcctggcccaccacctgaggatcaagatccacgagca
catcctgatccacggcgacatccggaagaccaccaagatggagatcggaggcgagga
ggtggaagtggaagagttcgtggaggaggaggacgaggacacagtggcggc
accggtagtagcagtgagtaagggcgaggaagtgatcaaagagttcatgcggtttaagg
tgagaatggaaggaagcatgaacggccacgagttcgaaattgagggagaaggagagg
gacggccctacgagggcacccagacagccaagctgaaagtgacaaagggcgggcc
tctgccattcgcttgggacatcctgagcccacagtttatgtacggctccaaggcctatgtga
aacatccagctgacattcccgattataagaaactgagcttccccgaggggtttaa
gtgggaaagagtgatgaacttcgaggacggaggcctggtgactgtgacccaggacag
ctccctgcaggatgggaccctgatctacaaggtgaaaatgagagggacaaattttcccc
tgatggacctgtgatgcagaagaaaactatgggatgggaggcctccaccgaaag
gctgtatccacgcgacggggtgctgaaaggagaaatccaccaggctctgaagctgaaagat
gggggacattacctggtggagttcaagacaatctacatggccaagaaacctgtgcagctgccag
gctactattacgtggacacaaaactggatatcacttcacacaacgaggactacacta
ttgtggagcagtatgaacggagcgagggagacaccatctgttcctgggccatgggactggaag
taccggctcagggtctagtggaaccgcctcaagcgaggataacaatatggctgtgatcaaa
gagttcatgaggtttaaggtgcgcatggagggcagcatgaatgggcacgaatttga
gattgaaggagagggcgaagggaggccttacgagggcacacagactgccaagctgaaagtga
ccaagggaggaccactgcctttcgcttgggatatcctgtctcctcagtttatgtacggaagta
aggcctatgtcaagcatcccgctgacattcctgattacaagaaactgtctttccc
agagggctttaagtgggagagagtgatgaattttgaagatggaggcctggtgaccgtgaca
caggactcctctctgcaggatggcactctgatctacaaagtcaaaatgcgcggcacc
aattttccacccgatgggcccgtgatgcagaagaaaacaatggggtgggag
gccagcactgaacggctgtatcctagagacggagtgctgaagggcgaaatccaccaggccctg
aagctgaaagacggcggccactacctggtggagttcaaaaccatctacatggccaagaa
accagtgcagctgcccggctattactatgtggacaccaagctggatatcacatcccacaatgaagac
tacaccattgtggaacagtatgagaggtctgaaggacgccaccatctgtttctgtacggcatgga
tgagctgtataagtaa SEQ ID NO: 4 pDNA: pCAG-mRuby3
Purpose: Delivers genes that express the mRuby3 marker
(transfected neurons will emit a 'red' fluorescence)
Sequence:
GACATTGATTATTGACTAGTTATTAATAGTAATCAATTACGGGGTCATTAGTTCATA
GCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGC
CAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACG
GTAAATGGCCCGCCTGGCATTATGCCCAGTACATGACCTTATGGGACTTTCCTACTT
GGCAGTACATCTACGTATTAGTCATCGCTATTACCATGGTCGAGGTGAGCCCCACGT -continued

| Informal Sequence Listing |
| --- |
| TCTGCTTCACTCTCCCCATCTCCCCCCCCTCCCCACCCCCAATTTTGTATTTATTTATT<br>TTTTAATTATTTTGTGCAGCGATGGGGGCGGGGGGGGGGGGGGGGCGCGCGCCAGG<br>CGGGGCGGGGCGGGGCGAGGGGCGGGGCGGGGCGAGGCGGAGAGGTGCGGCGGC<br>AGCCAATCAGAGCGGCGCGCTCCGAAAGTTTCCTTTTATGGCGAGGCGGCGGCGGC<br>GGCGGCCCTATAAAAAGCGAAGCGCGCGGCGGGCGGGAGTCGCTGCGCGCTGCCTT<br>CGCCCCGTGCCCCGCTCCGCCGCCGCCTCGCGCCGCCCGCCCCGGCTCTGACTGACC<br>GCGTTACTCCCACAGGTGAGCGGGCGGGACGGCCCTTCTCCTCCGGGCTGTAATTAG<br>CGCTTGGTTTAATGACGGCTTGTTTCTTTTCTGTGGCTGCGTGAAAGCCTTGAGGGGC<br>TCCGGGAGGGCCCTTTGTGCGGGGGGAGCGGCTCGGGGGGTGCGTGCGTGTGTGTG<br>TGCGTGGGGAGCGCCGCGTGCGGCTCCGCGCTGCCCGGCGGCTGTGAGCGCTGCGG<br>GCGCGGCGCGGGGCTTTGTGCGCTCCGCAGTGTGCGCGAGGGGAGCGCGGCCGGGG<br>GCGGTGCCCCGCGGTGCGGGGGGGGCTGCGAGGGGAACAAAGGCTGCGTGCGGGG<br>TGTGTGCGTGGGGGGGTGAGCAGGGGGTGTGGGCGCGTCGGTCGGGCTGCAACCCC<br>CCCTGCACCCCCCTCCCCGAGTTGCTGAGCACGGCCCGGCTTCGGGTGCGGGGCTCC<br>GTACGGGGCGTGGCGCGGGGCTCGCCGTGCCGGGCGGGGGGTGGCGGCAGGTGGG<br>GGTGCCGGGCGGGGCGGGGCCGCCTCGGGCCGGGGAGGGCTCGGGGGAGGGGCGC<br>GGCGGCCCCCGGAGCGCCGGCGGCTGTCGAGGCGCGGCGAGCCGCAGCCATTGCCT<br>TTTATGGTAATCGTGCGAGAGGGCGCAGGGACTTCCTTTGTCCCAAATCTGTGCGGA<br>GCCGAAATCTGGGAGGCGCCGCCGCACCCCCTCTAGCGGGCGCGGGGCGAAGCGGT<br>GCGGCGCCGGCAGGAAGGAAATGGGCGGGGAGGGCCTTCGTGCGTCGCCGCGCCGC<br>CGTCCCCTTCTCCCTCTCCAGCCTCGGGGCTGTCCGCGGGGGGACGGCTGCCTTCGG<br>GGGGGACGGGGCAGGGCGGGGTTCGGCTTCTGGCGTGTGACCGGCGGCTCTAGAGC<br>CTCTGCTAACCATGTTCATGCCTTCTTCTTTTTCCTACAGCTCCTGGGCAACGTGCTG<br>GTTATTGTGCTGTCTCATCATTTTGGCAAAGAATTCGGTACCGCGGGCCCGGGATCC<br>ACCGGTAGCGGCCGCGGCCGCTATGGTGTCTAAGGGCGAAGAGCTGATCAAGGAAA<br>ATATGCGTATGAAGGTGGTCATGGAAGGTTCGGTCAACGGCCACCAATTCAAATGC<br>ACAGGTGAAGGAGAAGGCAGACCGTACGAGGGAGTGCAAACCATGAGGATCAAAG<br>TCATCGAGGGAGGACCCCTGCCATTTGCCTTTGACATTCTTGCCACGTCGTTCATGTA<br>TGGCAGCCGTACCTTTATCAAGTACCCGGCCGACATCCCTGATTTCTTTAAACAGTC<br>CTTTCCTGAGGGTTTTACTTGGGAAAGAGTTACGAGATACGAAGATGGTGGAGTCGT<br>CACCGTCACGCAGGACACCAGCCTTGAGGATGGCGAGCTCGTCTACAACGTCAAGG<br>TCAGAGGGGTAAACTTTCCCTCCAATGGTCCCGTGATGCAGAAGAAGACCAAGGGT<br>TGGGAGCCTAATACAGAGATGATGTATCCAGCAGATGGTGGTCTGAGAGGATACAC<br>TGACATCGCACTGAAAGTTGATGGTGGTGGCCATCTGCACTGCAACTTCGTGACAAC<br>TTACAGGTCAAAAAAGACCGTCGGGAACATCAAGATGCCCGGTGTCCATGCCGTTG<br>ATCACCGCCTGGAAAGGATCGAGGAGAGTGACAATGAAACCTACGTAGTGCAAAGA<br>GAAGTGGCAGTTGCCAAATACAGCAACCTTGGTGGTGGCATGGACGAGCTGTACAA<br>GTGAGTAAGTATCAAGGTTACAAGACAGGTTTAAGGAGACCAATAGAAACTGGGCT<br>TGTCGAGACAGAGAAGACTCTTGCGTTTCTGATAGGCACCTATTGGTCTTACTGACA<br>TCCACTTTGCCTTTCTCTCCACAGGTGTCGACAATCAACCTCTGGATTACAAAATTTG<br>TGAAAGATTGACTGGTATTCTTAACTATGTTGCTCCTTTTACGCTATGTGGATACGCT<br>GCTTTAATGCCTTTGTATCATGCTATTGCTTCCCGTATGGCTTTCATTTTCTCCTCCTT<br>GTATAAATCCTGGTTGCTGTCTCTTTATGAGGAGTTGTGGCCCGTTGTCAGGCAACG<br>TGGCGTGGTGTGCACTGTGTTTGCTGACGCAACCCCCACTGGTTGGGGCATTGCCAC<br>CACCTGTCAGCTCCTTTCCGGGACTTTCGCTTTCCCCCTCCCTATTGCCACGGCGGAA<br>CTCATCGCCGCCTGCCTTGCCCGCTGCTGGACAGGGGCTCGGCTGTTGGGCACTGAC<br>AATTCCGTGGTGTTGTCGGGGAAGCTGACGTCCTTTCCATGGCTGCTCGCCTGTGTTG<br>CCACCTGGATTCTGCGCGGGACGTCCTTCTGCTACGTCCCTTCGGCCCTCAATCCAG<br>CGGACCTTCCTTCCCGCGGCCTGCTGCCGGCTCTGCGGCCTCTTCCGCGTCTTCGCCT<br>TCGCCCTCAGACGAGTCGGATCTCCCTTTGGGCCGCCTCCCCGCCTGGAATTCGAGC<br>TCGGTACGATCAGCCTCGACTGTGCCTTCTAGTTGCCAGCCATCTGTTGTTTGCCCCT<br>CCCCCGTGCCTTCCTTGACCCTGGAAGGTGCCACTCCCACTGTCCTTTCCTAATAAAA<br>TGAGGAAATTGCATCGCATTGTCTGAGTAGGTGTCATTCTATTCTGGGGGGTGGGGT<br>GGGGCAGGACAGCAAGGGGGAGGATTGGGAAGACAATAGCCCAGCTTTTGTTCCCT<br>TTAGTGAGGGTTAATTGCGCGCTTGGCGTAATCATGGTCATAGCTGTTTCCTGTGTG<br>AAATTGTTATCCGCTAATTCACTCCTCAGGTGCAGGCTGCCTATCAGAAGGTGGTGG<br>CTGGTGTGGCCAATGCCCTGGCTCACAAATACCACTGAGATCTTTTTCCCTCTGCCA<br>AAAATTATGGGGACATCATGAAGCCCCTTGAGCATCTGACTTCTGGCTAATAAAGGA<br>AATTTATTTTCATTGCAATAGTGTGTTGGAATTTTTTGTGTCTCTCACTCGGAAGGAC<br>ATATGGGAGGGCAAATCATTTAAAACATCAGAATGAGTATTTGGTTTAGAGTTTGGC<br>AACATATGCCCATATGCTGGCTGCCATGAACAAAGGTTGGCTATAAAGAGGTCATC<br>AGTATATGAAACAGCCCCCTGCTGTCCATTCCTTATTCCATAGAAAAGCCTTGACTT<br>GAGGTTAGATTTTTTTTATATTTTGTTTTGTGTTATTTTTTTCTTTAACATCCCTAAAA<br>TTTTCCTTACATGTTTTACTAGCCAGATTTTTCCTCCTCTCCTGACTACTCCCAGTCAT<br>AGCTGTCCCTCTTCTCTTATGGAGATCCCTCGACCTGCAGCCCAAGCTTGGCGTAAT<br>CATGGTCATAGCTGTTTCCTGTGTGAAATTGTTATCCGCTCACAATTCCACACAACAT<br>ACGAGCCGGAAGCATAAAGTGTAAAGCCTGGGGTGCCTAATGAGTGAGCTAACTCA<br>CATTAATTGCGTTGCGCTCACTGCCCGCTTTCCAGTCGGGAAACCTGTCGTGCCAGC<br>GGATCCGCATCTCAATTAGTCAGCAACCATAGTCCCGCCCCTAACTCCGCCCATCCC<br>GCCCCTAACTCCGCCCAGTTCCGCCCATTCTCCGCCCCATGGCTGACTAATTTTTTT<br>ATTTATGCAGAGGCCGAGGCCGCCTCGGCCTCTGAGCTATTCCAGAAGTAGTGAGG<br>AGGCTTTTTTGGAGGCCTAGGCTTTTGCAAAAAGCTAACTTGTTTATTGCAGCTTATA<br>ATGGTTACAAATAAAGCAATAGCATCACAAATTTCACAAATAAAGCATTTTTTTCAC<br>TGCATTCTAGTTGTGGTTTGTCCAAACTCATCAATGTATCTTATCATGTCTGGATCCG<br>CTGCATTAATGAATCGGCCAACGCGCGGGGAGAGGCGGTTTGCGTATTGGGCGCTCT<br>TCCGCTTCCTCGCTCACTGACTCGCTGCGCTCGGTCGTTCGGCTGCGGCGAGCGGTA<br>TCAGCTCACTCAAAGGCGGTAATACGGTTATCCACAGAATCAGGGGATAACGCAGG |

-continued

| Informal Sequence Listing |
|---|
| AAAGAACATGTGAGCAAAAGGCCAGCAAAAGGCCAGGAACCGTAAAAAGGCCGCG |
| TTGCTGGCGTTTTTCCATAGGCTCCGCCCCCCTGACGAGCATCACAAAAATCGACGC |
| TCAAGTCAGAGGTGGCGAAACCCGACAGGACTATAAAGATACCAGGCGTTTCCCCC |
| TGGAAGCTCCCTCGTGCGCTCTCCTGTTCCGACCCTGCCGCTTACCGGATACCTGTCC |
| GCCTTTCTCCCTTCGGGAAGCGTGGCGCTTTCTCATAGCTCACGCTGTAGGTATCTCA |
| GTTCGGTGTAGGTCGTTCGCTCCAAGCTGGGCTGTGTGCACGAACCCCCCGTTCAGC |
| CCGACCGCTGCGCCTTATCCGGTAACTATCGTCTTGAGTCCAACCCGGTAAGACACG |
| ACTTATCGCCACTGGCAGCAGCCACTGGTAACAGGATTAGCAGAGCGAGGTATGTA |
| GGCGGTGCTACAGAGTTCTTGAAGTGGTGGCCTAACTACGGCTACACTAGAAGAAC |
| AGTATTTGGTATCTGCGCTCTGCTGAAGCCAGTTACCTTCGGAAAAAGAGTTGGTAG |
| CTCTTGATCCGGCAAACAAACCACCGCTGGTAGCGGTGGTTTTTTTGTTTGCAAGCA |
| GCAGATTACGCGCAGAAAAAAAGGATCTCAAGAAGATCCTTTGATCTTTTCTACGGG |
| GTCTGACGCTCAGTGGAACGAAAACTCACGTTAAGGGATTTTGGTCATGAGATTATC |
| AAAAAGGATCTTCACCTAGATCCTTTTAAATTAAAAATGAAGTTTTAAATCAATCTA |
| AAGTATATATGAGTAAACTTGGTCTGACAGTTACCAATGCTTAATCAGTGAGGCACC |
| TATCTCAGCGATCTGTCTATTTCGTTCATCCATAGTTGCCTGACTCCCCGTCGTGTAG |
| ATAACTACGATACGGGAGGGCTTACCATCTGGCCCCAGTGCTGCAATGATACCGCG |
| AGACCCACGCTCACCGGCTCCAGATTTATCAGCAATAAACCAGCCAGCCGGAAGGG |
| CCGAGCGCAGAAGTGGTCCTGCAACTTTATCCGCCTCCATCCAGTCTATTAATTGTT |
| GCCGGGAAGCTAGAGTAAGTAGTTCGCCAGTTAATAGTTTGCGCAACGTTGTTGCCA |
| TTGCTACAGGCATCGTGGTGTCACGCTCGTCGTTTGGTATGGCTTCATTCAGCTCCGG |
| TTCCCAACGATCAAGGCGAGTTACATGATCCCCCATGTTGTGCAAAAAAGCGGTTAG |
| CTCCTTCGGTCCTCCGATCGTTGTCAGAAGTAAGTTGGCCGCAGTGTTATCACTCATG |
| GTTATGGCAGCACTGCATAATTCTCTTACTGTCATGCCATCCGTAAGATGCTTTTCTG |
| TGACTGGTGAGTACTCAACCAAGTCATTCTGAGAATAGTGTATGCGGCGACCGAGTT |
| GCTCTTGCCCGGCGTCAATACGGGATAATACCGCGCCACATAGCAGAACTTTAAAA |
| GTGCTCATCATTGGAAAACGTTCTTCGGGGCGAAAACTCTCAAGGATCTTACCGCTG |
| TTGAGATCCAGTTCGATGTAACCCACTCGTGCACCCAACTGATCTTCAGCATCTTTTA |
| CTTTCACCAGCGTTTCTGGGTGAGCAAAAACAGGAAGGCAAAATGCCGCAAAAAAG |
| GGAATAAGGGCGACACGGAAATGTTGAATACTCATACTCTTCCTTTTTCAATATTAT |
| TGAAGCATTTATCAGGGTTATTGTCTCATGAGCGGATACATATTTGAATGTATTTAG |
| AAAAATAAACAAATAGGGGTTCCGCGCACATTTCCCCGAAAAGTGCCACCTGGTC |

What is claimed is:

1. A brain-computer interface (BCI) configured to be engrafted on a brain of a mammal, the BCI comprising:
   - a cortical graft layer comprising a plurality of exogenous neuronal cells configured to be transplanted on the brain's cerebral cortex, the plurality of exogenous neuronal cells being configured to engraft on the brain;
   - processing circuitry configured to send and receive information to and from the brain of the mammal via the cortical graft layer;
   - a camera configured to capture image data of the cortical graft layer and connect to the processing circuitry to obtain information from the cortical graft layer; and
   - a light source configured to illuminate the cortical graft layer based on signals from the processing circuitry to transmit information to the cortical graft layer,
   - wherein the exogenous neuronal cells are configured to, at an outermost cortical layer, penetrate the brain by processes growing from the exogenous neuronal cells.

2. The brain-computer interface of claim 1, wherein the exogenous neuronal cells are transfected.

3. The brain-computer interface of claim 2, wherein transfection is ex vivo with a plasmid by electroporation.

4. The brain-computer interface of claim 2, wherein transfection is via virus-mediated transfection.

5. The brain-computer interface of claim 1, wherein the exogenous neuronal cells are tissue cultured mammalian stem cells.

6. The brain-computer interface of claim 5, wherein the exogenous neuronal cells are chemically tethered to an electrode.

7. The brain-computer interface of claim 3, wherein the plasmid contains a GCaMP nucleic acid sequence.

8. The brain-computer interface of claim 1, wherein the cortical graft layer is configured to extend axons and dendrites into the cerebral cortex or striatum.

9. The brain-computer interface of claim 1, wherein the cortical graft layer is configured to form synaptic connections to enable bidirectional communication.

10. The brain-computer interface of claim 1, wherein the cortical graft layer is configured to be engrafted over a lobe of the cerebral cortex selected from the group consisting of the frontal lobe, the parietal lobe, the temporal lobe, the occipital lobe and a combination thereof.

11. The brain-computer interface of claim 1, wherein the cortical graft layer is about 50 microns to about 1 mm in thickness.

12. The brain-computer interface of claim 1, wherein the light source has a wavelength of about 300 nm to about 1.5 microns.

13. The brain-computer interface of claim 1, wherein the mammal is a human.

14. The brain-computer interface of claim 13, wherein the human has an impairment selected from the group consisting of a motor skill, a sight function, an auditory function, a taste function and an olfactory function.

15. A brain-computer interface (BCI) configured to be engrafted on a brain of a mammal, the BCI comprising:
   - a cortical graft layer comprising a plurality of exogenous neuronal cells configured to be transplanted on the brain's cerebral cortex, the plurality of exogenous neuronal cells being configured to engraft on the brain; and
   - a signal detector configured to detect a detectable signal,
   - wherein the exogenous neuronal cells are configured to, at an outermost cortical layer, penetrate the brain by processes growing from the exogenous neuronal cells, and
   - wherein the exogenous neuronal cells are tethered to electrodes connected to the signal detector.

16. A brain-computer interface (BCI) configured to be engrafted on a brain of a mammal, the BCI comprising:

a cortical graft layer comprising a plurality of exogenous neuronal cells configured to be transplanted on the brain's cerebral cortex, the plurality of exogenous neuronal cells being configured to engraft on the brain; and processing circuitry configured to send information to the brain of the mammal via the cortical graft layer, wherein the exogenous neuronal cells are configured to, at an outermost cortical layer, penetrate the brain by processes growing from the exogenous neuronal cells, and wherein the exogenous neuronal cells are tethered to electrodes connected to the processing circuitry.

17. A brain-computer interface (BCI) configured to be engrafted on a brain of a mammal, the BCI comprising:

a cortical graft layer comprising a plurality of exogenous neuronal cells configured to be transplanted on the brain's cerebral cortex, the plurality of exogenous neuronal cells being configured to engraft on the brain;

processing circuitry configured to send information to the brain of the mammal via the cortical graft layer; and a light source configured to illuminate the cortical graft layer based on signals from the processing circuitry to transmit information to the cortical graft layer, wherein the exogenous neuronal cells are configured to, at an outermost cortical layer, penetrate the brain by processes growing from the exogenous neuronal cells.

18. A brain-computer interface (BCI) configured to be engrafted on a brain of a mammal, the BCI comprising:

a cortical graft layer comprising a plurality of exogenous neuronal cells configured to be transplanted on the brain's cerebral cortex, the plurality of exogenous neuronal cells being configured to engraft on the brain;

processing circuitry configured to receive information from the brain of the mammal via the cortical graft layer; and a camera configured to capture image data of the cortical graft layer and connect to the processing circuitry to obtain information from the cortical graft layer, wherein the exogenous neuronal cells are configured to, at an outermost cortical layer, penetrate the brain by processes growing from the exogenous neuronal cells.

* * * * *